(12) United States Patent
Kenyon et al.

(10) Patent No.: US 12,029,850 B2
(45) Date of Patent: Jul. 9, 2024

(54) RESPIRATORY PRESSURE THERAPY SYSTEM

(71) Applicant: ResMed Pty Ltd, Bella Vista (AU)

(72) Inventors: Barton John Kenyon, Sydney (AU); Emily Claire Shrubb, Sydney (AU); Liam Holley, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 284 days.

(21) Appl. No.: 17/485,868

(22) Filed: Sep. 27, 2021

(65) Prior Publication Data

US 2022/0016375 A1    Jan. 20, 2022

Related U.S. Application Data

(63) Continuation of application No. 16/320,565, filed as application No. PCT/AU2017/050761 on Jul. 25, 2017, now Pat. No. 11,167,102.

(Continued)

(30) Foreign Application Priority Data

Jul. 25, 2016  (AU) ............................... 2016902914
Oct. 11, 2016  (AU) ............................... 2016904093

(51) Int. Cl.
*A61M 16/00* (2006.01)
*A61M 16/06* (2006.01)
(Continued)

(52) U.S. Cl.
CPC ........ *A61M 16/0069* (2014.02); *A61M 16/00* (2013.01); *A61M 16/024* (2017.08);
(Continued)

(58) Field of Classification Search
CPC .......... A61M 16/0066; A61M 16/0069; A61M 16/024; A61M 16/0616; A61M 16/0666;
(Continued)

(56) References Cited

U.S. PATENT DOCUMENTS 4,782,832 A    11/1988  Trimble et al.
4,944,310 A     7/1990  Sullivan
(Continued)

FOREIGN PATENT DOCUMENTS

CN       1688358 A    10/2005
CN     102596299 A     7/2012
(Continued)

OTHER PUBLICATIONS

Office Action dated Nov. 14, 2022 issued in Japanese Application No. 2021-208172 with English translation (6 pages).
(Continued)

*Primary Examiner* — Joseph D. Boecker
(74) *Attorney, Agent, or Firm* — Nixon & Vanderhye P.C.

(57) ABSTRACT

The present technology is directed to a respiratory pressure therapy system, that includes a plenum chamber pressurisable to a therapeutic pressure above ambient air pressure, a seal-forming structure to form a seal with an entrance to the patient's airways to maintain said therapeutic pressure in the plenum chamber throughout the patient's respiratory cycle in use, a positioning and stabilising structure constructed and arranged to provide an elastic force to hold the seal-forming structure in a therapeutically effective position on the patient's head, a blower configured to generate the flow of air and pressurise the plenum chamber to the therapeutic pressure, the blower having a motor, the blower being connected to the plenum chamber such that the blower is suspended from the patient's head and the axis of rotation of the motor is perpendicular to the patient's sagittal plane, and (Continued)

a power supply configured to provide electrical power to the blower.

42 Claims, 65 Drawing Sheets

Related U.S. Application Data

(60) Provisional application No. 62/512,445, filed on May 30, 2017, provisional application No. 62/458,862, filed on Feb. 14, 2017.

(51) Int. Cl.
| | |
|---|---|
| *A61M 16/10* | (2006.01) |
| *A61M 16/20* | (2006.01) |
| *F04D 13/06* | (2006.01) |
| *F04D 15/00* | (2006.01) |
| *F04D 17/16* | (2006.01) |
| *F04D 29/28* | (2006.01) |
| *F04D 29/30* | (2006.01) |
| *F04D 29/42* | (2006.01) |
| *F04D 29/44* | (2006.01) |

(52) U.S. Cl.
CPC .... *A61M 16/0616* (2014.02); *A61M 16/0666* (2013.01); *A61M 16/0683* (2013.01); *A61M 16/1045* (2013.01); *A61M 16/208* (2013.01); *F04D 13/068* (2013.01); *F04D 15/00* (2013.01); *F04D 17/162* (2013.01); *F04D 17/164* (2013.01); *F04D 29/281* (2013.01); *F04D 29/30* (2013.01); *F04D 29/424* (2013.01); *F04D 29/444* (2013.01); *A61M 2016/0027* (2013.01); *A61M 2016/0033* (2013.01); *A61M 2205/3341* (2013.01); *A61M 2205/8206* (2013.01); *A61M 2209/088* (2013.01); *A61M 2210/06* (2013.01); *F05D 2240/303* (2013.01); *F05D 2240/304* (2013.01)

(58) Field of Classification Search
CPC .......... A61M 16/0683; F04D 17/105; F04D 17/162; F04D 29/424; F04D 29/624; F04D 29/626
See application file for complete search history.

(56) References Cited

U.S. PATENT DOCUMENTS

| | | | |
|---|---|---|---|
| 5,687,715 A | 11/1997 | Landis | |
| 5,888,053 A * | 3/1999 | Kobayashi | ............ F04D 29/445 417/244 |
| 6,532,959 B1 | 3/2003 | Berthon-Jones | |
| 6,581,594 B1 | 6/2003 | Drew et al. | |
| 6,910,483 B2 | 6/2005 | Daly et al. | |
| 7,302,950 B2 | 12/2007 | Berthon-Jones et al. | |
| D589,136 S | 3/2009 | Kenyon et al. | |
| 7,866,944 B2 | 1/2011 | Kenyon et al. | |
| 7,913,692 B2 | 3/2011 | Kwok | |
| 8,272,837 B2 | 9/2012 | Kenyon et al. | |
| 8,636,479 B2 | 1/2014 | Kenyon et al. | |
| 8,638,014 B2 | 1/2014 | Sears et al. | |
| 8,667,962 B2 | 3/2014 | Kenyon et al. | |
| 8,733,349 B2 | 5/2014 | Bath et al. | |
| 8,973,576 B2 | 3/2015 | Kenyon et al. | |
| 9,132,252 B2 | 9/2015 | Barlow et al. | |
| 9,144,654 B2 | 9/2015 | Kwok | |
| 9,155,857 B2 | 10/2015 | Lalonde | |
| 9,259,547 B2 | 2/2016 | Meynink et al. | |
| 9,586,016 B2 | 3/2017 | Kwok | |
| 9,616,190 B2 | 4/2017 | Rummery et al. | |
| 9,677,563 B2 | 6/2017 | Kenyon et al. | |
| 9,861,774 B2 | 1/2018 | Fu et al. | |
| 9,993,605 B2 | 6/2018 | Barlow et al. | |
| 10,092,716 B2 | 10/2018 | Velzy et al. | |
| 10,124,135 B2 | 11/2018 | Kenyon et al. | |
| 2003/0084900 A1 | 5/2003 | Leclerc et al. | |
| 2003/0168064 A1 | 9/2003 | Daly et al. | |
| 2003/0172930 A1 | 9/2003 | Kullik et al. | |
| 2004/0040562 A1 | 3/2004 | Brunell | |
| 2004/0255948 A1 | 12/2004 | Smith et al. | |
| 2007/0000493 A1 | 1/2007 | Cox | |
| 2007/0277827 A1 | 12/2007 | Bordewick | |
| 2009/0044808 A1 | 2/2009 | Guney et al. | |
| 2009/0050156 A1 | 2/2009 | Ng et al. | |
| 2009/0194101 A1 | 8/2009 | Kenyon | |
| 2009/0246013 A1 * | 10/2009 | Kenyon | ............ A61M 16/0066 415/208.2 |
| 2010/0000534 A1 | 1/2010 | Kooij et al. | |
| 2010/0101575 A1 | 4/2010 | Ludwik et al. | |
| 2012/0024289 A1 * | 2/2012 | Johnstone | ............ A62B 18/045 128/205.12 |
| 2012/0152255 A1 | 6/2012 | Barlow | |
| 2012/0157794 A1 | 6/2012 | Goodwin et al. | |
| 2012/0167879 A1 | 7/2012 | Bowman | |
| 2012/0266873 A1 | 10/2012 | Lalonde | |
| 2013/0087151 A1 | 4/2013 | Klockseth | |
| 2013/0104883 A1 | 5/2013 | Lalonde | |
| 2013/0118484 A1 | 5/2013 | Ishikita | |
| 2013/0152918 A1 | 6/2013 | Rummery | |
| 2013/0276789 A1 | 10/2013 | Garde et al. | |
| 2013/0306072 A1 | 11/2013 | Moir et al. | |
| 2014/0060542 A1 | 3/2014 | Volmer et al. | |
| 2014/0137870 A1 | 5/2014 | Barlow | |
| 2014/0158131 A1 * | 6/2014 | Kenyon | ............ A61M 16/0069 128/204.18 |
| 2015/0128948 A1 | 5/2015 | Rapoport | |
| 2015/0157818 A1 | 6/2015 | Darby | |
| 2015/0320958 A1 | 11/2015 | Metysek | |
| 2017/0002830 A1 * | 1/2017 | Bothma | ................ F04D 29/667 |
| 2017/0113014 A1 | 4/2017 | Nitta | |
| 2017/0361133 A1 | 12/2017 | Yu et al. | |
| 2019/0160240 A1 * | 5/2019 | Bothma | ................ A61M 16/109 |
| 2019/0269871 A1 | 9/2019 | Kenyon et al. | |
| 2022/0088330 A1 | 3/2022 | Kenyon et al. | |

FOREIGN PATENT DOCUMENTS

| | | |
|---|---|---|
| CN | 102686888 A | 9/2012 |
| CN | 103352866 A | 10/2013 |
| CN | 103442760 A | 12/2013 |
| CN | 104189979 A | 12/2014 |
| CN | 104271189 A | 1/2015 |
| DE | 10 2012 017176 A1 | 3/2014 |
| EP | 2 027 880 A1 | 2/2009 |
| GB | 2478027 A | 8/2011 |
| JP | 2007-506482 A | 3/2007 |
| JP | 2009-537735 A | 10/2009 |
| JP | 2010-512198 A | 4/2010 |
| JP | 2013-501541 | 1/2013 |
| JP | 2014-524268 | 9/2014 |
| JP | 2015-181894 | 10/2015 |
| NZ | 585826 A | 11/2011 |
| WO | 98/004310 A1 | 2/1998 |
| WO | 98/034665 A1 | 8/1998 |
| WO | 2000/078381 A1 | 12/2000 |
| WO | 2004/073778 A1 | 9/2004 |
| WO | 2005/028009 A1 | 3/2005 |
| WO | 2005/063328 A1 | 7/2005 |
| WO | 2006/074513 A1 | 7/2006 |
| WO | 2006/130903 A1 | 12/2006 |
| WO | 2007/134405 A1 | 11/2007 |
| WO | 2008/028247 A1 | 3/2008 |
| WO | 2009/052560 A1 | 4/2009 |
| WO | 2009/088545 A2 | 7/2009 |
| WO | 2010/135785 A1 | 12/2010 |
| WO | 2011/022779 A1 | 3/2011 |
| WO | 2012/171072 A1 | 12/2012 |
| WO | 2013/020167 A1 | 2/2013 |
| WO | 2013/067592 A1 | 5/2013 |
| WO | 2014/007655 A2 | 1/2014 |

(56) References Cited

FOREIGN PATENT DOCUMENTS

| WO | 2014/140600 | A1 | 9/2014 |
|----|-------------|----|--------|
| WO | 2015/097632 | A1 | 7/2015 |
| WO | 2016/086273 | A1 | 6/2016 |
| WO | 2018/148789 | A1 | 8/2018 |

OTHER PUBLICATIONS

Notice of Allowance dated Nov. 22, 2021 issued in Japanese Application No. 2019-526345 (3 pages).
Extended European Search Report dated Dec. 16, 2021 issued in European Application No. 21192659.7 (8 pages).
Office Action dated Jun. 5, 2023 issued in Japanese Application No. 2021-208172 with English translation (7 pages).
Office Action dated Apr. 12, 2021 issued in Japanese Application No. 2019-526345 with English translation (14 pages).
Office Action dated Mar. 2, 2021 issued in Chinese Application No. 201780058850.9 with English translation (20 pages).
Extended European Search Report dated Sep. 12, 2019 issued in European Application No. 17833089.0 (5 pages).
"*Respiratory Physiology*", by John B. West, Lippincott Williams & Wilkins, 9$^{th}$ edition published 2012 (8 pages).
PCT International Search Report from Application No. PCT/AU2017/050761, dated Nov. 10, 2017 (13 pages).
PCT Written Opinion of the International Searching Authority from Application No. PCT/AU2017/050761, dated Nov. 10, 2017 (14 pages).
Second PCT Written Opinion of the International Preliminary Examining Authority from Application No. PCT/AU2017/050761, dated Jul. 18, 2018 (13 pages).
PCT IPRP from Application No. PCT/AU2017/050761, dated Nov. 19, 2018 (43 pages).
Decision to Grant dated Jan. 24, 2024 issued in Chinese Application No. 202111356917.1 (6 pages).
Examination Report dated Feb. 12, 2024 issued in New Zealand Application No. 790377 (3 pages).
Examination Report dated Feb. 12, 2024 issued in New Zealand Application No. 750095 (2 pages).
Examination report dated Feb. 12, 2024 issued in New Zealand Application No. 790340 (2 pages).
Examination Report dated Feb. 12, 2024 issued in New Zealand Application No. 790375 (3 pages).
Examiantion Report dated Feb. 13, 2024 issued in New Zealand Application No. 790378 (4 pages).
Examination Report dated Feb. 12, 2024 issued in New Zealand Application No. 790376 (2 pages).

\* cited by examiner

RESPIRATORY PRESSURE THERAPY SYSTEM

1 CROSS-REFERENCE TO RELATED APPLICATIONS

This application is a continuation of U.S. application Ser. No. 16/320,565, filed Jan. 25, 2019, now U.S. Pat. No. 11,167,102, is the U.S. national phase of International Application No. PCT/AU2017/050761 filed Jul. 25, 2017, which designated the U.S. and claims priority to Australian Provisional Application No. 2016902914, filed Jul. 25, 2016, Australian Provisional Application No. 2016904093, filed Oct. 11, 2016, and claims the benefit of U.S. Provisional Application No. 62/458,862, filed Feb. 14, 2017, and U.S. Provisional Application No. 62/512,445 filed by May 30, 2017, each of which is incorporated herein by reference in its entirety.

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

2 BACKGROUND OF THE TECHNOLOGY

2.1 Field of the Technology

The present technology relates to one or more of the detection, diagnosis, treatment, prevention and amelioration of respiratory-related disorders. The present technology also relates to medical devices or apparatus, and their use.

2.2 Description of the Related Art 2.2.1 Human Respiratory System and its Disorders The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the inhaled air into the venous blood and carbon dioxide to move in the opposite direction. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "*Respiratory Physiology*", by John B. West, Lippincott Williams & Wilkins, 9th edition published 2012.

A range of respiratory disorders exist. Certain disorders may be characterised by particular events, e.g. apneas, hypopneas, and hyperpneas.

Examples of respiratory disorders include Obstructive Sleep Apnea (OSA), Cheyne-Stokes Respiration (CSR), respiratory insufficiency, Obesity Hyperventilation Syndrome (OHS), Chronic Obstructive Pulmonary Disease (COPD), Neuromuscular Disease (NMD) and Chest wall disorders.

2.2.2 Therapy

Various therapies, such as Continuous Positive Airway Pressure (CPAP) therapy, Non-invasive ventilation (NIV) and Invasive ventilation (IV) have been used to treat one or more of the above respiratory disorders.

2.2.3 Treatment Systems

These therapies may be provided by a treatment system or device. Such systems and devices may also be used to diagnose a condition without treating it.

A treatment system may comprise a Respiratory Pressure Therapy Device (RPT device), an air circuit, a humidifier, a patient interface, and data management.

Another form of treatment system is a mandibular repositioning device.

2.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 $cmH_2O$ relative to ambient pressure. For other forms of therapy, such as the delivery of oxygen, the patient interface may not include a seal sufficient to facilitate delivery to the airways of a supply of gas at a positive pressure of about 10 $cmH_2O$.

2.2.3.2 Respiratory Pressure Therapy (RPT) Device

A respiratory pressure therapy (RPT) device may be used to deliver one or more of a number of therapies described above, such as by generating a flow of air for delivery to an entrance to the airways. The flow of air may be pressurised. Examples of RPT devices include a CPAP device and a ventilator.

Air pressure generators are known in a range of applications, e.g. industrial-scale ventilation systems. However, air pressure generators for medical applications have particular requirements not fulfilled by more generalised air pressure generators, such as the reliability, size and weight requirements of medical devices. In addition, even devices designed for medical treatment may suffer from shortcomings, pertaining to one or more of: comfort, noise, ease of use, efficacy, size, weight, manufacturability, cost, and reliability.

An example of the special requirements of certain RPT devices is acoustic noise.

Table of noise output levels of prior RPT devices (one specimen only, measured using test method specified in ISO 3744 in CPAP mode at 10 $cmH_2O$).

| RPT Device name | A-weighted sound pressure level dB (A) | Year (approx.) |
| --- | --- | --- |
| C-Series Tango ™ | 31.9 | 2007 |
| C-Series Tango ™ with Humidifier | 33.1 | 2007 |
| S8 Escape ™ II | 30.5 | 2005 |
| S8 Escape ™ II with H4i ™ Humidifier | 31.1 | 2005 |
| S9 AutoSet ™ | 26.5 | 2010 |
| S9 AutoSet ™ with H5i Humidifier | 28.6 | 2010 |

One known RPT device used for treating sleep disordered breathing is the S9 Sleep Therapy System, manufactured by ResMed Limited. Another example of an RPT device is a ventilator. Ventilators such as the ResMed Stellar™ Series of Adult and Paediatric Ventilators may provide support for invasive and non-invasive non-dependent ventilation for a range of patients for treating a number of conditions such as but not limited to NMD, OHS and COPD.

The ResMed Elisée™ 150 ventilator and ResMed VS III™ ventilator may provide support for invasive and non-invasive dependent ventilation suitable for adult or paediatric patients for treating a number of conditions. These ventilators provide volumetric and barometric ventilation modes with a single or double limb circuit. RPT devices typically comprise a pressure generator, such as a motor-driven blower or a compressed gas reservoir, and are configured to supply a flow of air to the airway of a patient. In some cases, the flow of air may be supplied to the airway of the patient at positive pressure. The outlet of the RPT device is connected via an air circuit to a patient interface such as those described above.

The designer of a device may be presented with an infinite number of choices to make. Design criteria often conflict, meaning that certain design choices are far from routine or inevitable. Furthermore, the comfort and efficacy of certain aspects may be highly sensitive to small, subtle changes in one or more parameters.

2.2.3.3 Humidifier

Delivery of a flow of air without humidification may cause drying of airways. The use of a humidifier with an RPT device and the patient interface produces humidified gas that minimizes drying of the nasal mucosa and increases patient airway comfort. In addition in cooler climates, warm air applied generally to the face area in and about the patient interface is more comfortable than cold air.

2.2.3.4 Data Management

There may be clinical reasons to obtain data to determine whether the patient prescribed with respiratory therapy has been "compliant", e.g. that the patient has used their RPT device according to certain a "compliance rule". One example of a compliance rule for CPAP therapy is that a patient, in order to be deemed compliant, is required to use the RPT device for at least four hours a night for at least 21 of 30 consecutive days. In order to determine a patient's compliance, a provider of the RPT device, such as a health care provider, may manually obtain data describing the patient's therapy using the RPT device, calculate the usage over a predetermined time period, and compare with the compliance rule. Once the health care provider has determined that the patient has used their RPT device according to the compliance rule, the health care provider may notify a third party that the patient is compliant.

There may be other aspects of a patient's therapy that would benefit from communication of therapy data to a third party or external system.

Existing processes to communicate and manage such data can be one or more of costly, time-consuming, and error-prone.

2.2.3.5 Vent Technologies

Some forms of treatment systems may include a vent to allow the washout of exhaled carbon dioxide. The vent may allow a flow of gas from an interior space of a patient interface, e.g., the plenum chamber, to an exterior of the patient interface, e.g., to ambient.

3 BRIEF SUMMARY OF THE TECHNOLOGY

The present technology is directed towards providing medical devices used in the diagnosis, amelioration, treatment, or prevention of respiratory disorders having one or more of improved comfort, cost, efficacy, ease of use and manufacturability.

A first aspect of the present technology relates to an apparatus used in the diagnosis, amelioration, treatment or prevention of a respiratory disorder.

Another aspect of the present technology relates to methods used in the diagnosis, amelioration, treatment or prevention of a respiratory disorder.

An aspect of certain forms of the present technology is to provide methods and/or apparatus that improve the compliance of patients with respiratory therapy.

An aspect of certain forms of the present technology is a medical device that is easy to use, e.g. by a person who does not have medical training, by a person who has limited dexterity, vision or by a person with limited experience in using this type of medical device.

An aspect of one form of the present technology is a portable RPT device that may be carried by a person, e.g., around the home of the person.

An aspect of one form of the present technology is a patient interface that may be washed in a home of a patient, e.g., in soapy water, without requiring specialised cleaning equipment. An aspect of one form of the present technology is a humidifier tank that may be washed in a home of a patient, e.g., in soapy water, without requiring specialised cleaning equipment.

The methods, systems, devices and apparatus described herein can provide improved functioning in a processor, such as of a processor of a specific purpose computer, respiratory monitor and/or a respiratory therapy apparatus. Moreover, the described methods, systems, devices and apparatus can provide improvements in the technological field of automated management, monitoring and/or treatment of respiratory conditions, including, for example, sleep disordered breathing.

Another aspect of the present technology is directed to a respiratory pressure therapy (RPT) system that includes a patient interface and a pressure generator, wherein the pressure generator is supported on the patient's head in use by the patient interface.

Another aspect of the present technology is directed to a pressure generator having a single motor and a single shaft, each end of the shaft positioned at a corresponding end of the motor. The pressure generator may further comprise at least one compression stage associated with each end of the shaft, each compression stage including an impeller and a stator.

Another aspect of the present technology is directed to a blower that includes an blower inlet at each lateral and at least one blower outlet positioned between the blower inlets, the blower outlet extending annularly around at least a portion of the circumference of the blower.

Another aspect of the present technology is directed to a respiratory pressure therapy (RPT) system. The RPT system comprises: a plenum chamber pressurisable to a therapeutic pressure of at least 6 cmH$_2$O above ambient air pressure; a seal-forming structure constructed and arranged to form a seal with a region of the patient's face at or surrounding an entrance to the patient's airways such that a flow of gas at said therapeutic pressure is delivered to at least the entrance to the patient's nares, the seal-forming structure constructed and arranged to maintain said therapeutic pressure in the plenum chamber throughout the patient's respiratory cycle in use; a positioning and stabilising structure constructed and arranged to provide an elastic force to hold the seal-forming structure in a therapeutically effective position on the patient's head, the positioning and stabilising structure comprising a tie, a lateral portion of the tie being constructed and arranged to overlie a region of the patient's head superior to the otobasion superior in use, and a superior portion of the tie being constructed and arranged to overlie a region of the patient's head in a region of the parietal bone in use, wherein the positioning and stabilising structure has a non-rigid decoupling portion; a blower configured to generate the flow of gas and pressurise the plenum chamber to the therapeutic pressure, the blower having a motor, the blower being connected to the plenum chamber such that in use the blower is suspended from the patient's head and an axis of rotation of the motor is generally perpendicular to the patient's sagittal plane; and a power supply configured to provide electrical power to the blower.

In examples, (a) the seal-forming structure may be constructed such that no part thereof enters the patient's mouth in use, (b) the seal-forming structure may not extend internally of the patient's airways, (c) the plenum chamber may not cover the eyes in use, (d) the blower may be contained at least partially within the plenum chamber, (e) the plenum chamber may comprise at least one housing portion, (e) the plenum chamber may comprise at least two housing portions that are at least partially separable to allow the blower to be removed from the plenum chamber, (f) the at least two housing portions may be joined at one side in a clamshell arrangement to allow the plenum chamber to be opened and closed, (g) the RPT system may comprise a sealing structure between the at least two housing portions, (h) the plenum chamber may include at least one attachment structure to attach the positioning and stabilising structure to secure the RPT system to the patient's head in use, (i) the plenum chamber may comprise a plenum chamber outlet through which the flow of gas passes from the blower to at least the entrance to the patient's nares in use, (j) the seal-forming structure may be connected to the plenum chamber at the plenum chamber outlet, (k) the plenum chamber may comprise a port that is configured to be connected to at least one of a pressure transducer and a supplemental gas source, (l) the seal-forming structure may comprise: a pair of nasal puffs, or nasal pillows, each nasal puff or nasal pillow being constructed and arranged to form a seal with a respective naris of the nose of the patient; a seal-forming structure that forms a seal in use on a nose bridge region or on a nose-ridge region of the patient's face and that forms a seal in use on an upper lip region of the patient's face; or a seal-forming structure that forms a seal in use on a nose bridge region or on a nose-ridge region of the patient's face and that forms a seal in use on a chin-region of the patient's face, (m) the RPT system may comprise a heat and moisture exchanger (HME) within the plenum chamber that is positioned in the flow of gas and downstream of the blower, (n) the RPT system may not include a vent such that in use the patient exhales through the blower in opposition to the flow of gas and the patient's exhalate exits the RPT system through an inlet of the blower, (o) the power supply may comprise a battery, the battery may comprise at least one electrochemical cell, (p) the battery may be supported by the positioning and stabilising structure on a region of the patient's head adjacent to the parietal bone, (q) the battery may be contained within the positioning and stabilising structure, (r) the RPT system may comprise at least one wire supported by the positioning and stabilising structure, the at least one wire providing electrical communication between the blower and the battery, (s) the at least one wire may be contained within the lateral portion of the positioning and stabilising structure, (t) the RPT system may comprise at least one tube in fluid communication with the plenum chamber at a first end and a pressure transducer at a second end, the at least one tube contained within the lateral portion of the positioning and stabilising structure, (u) the seal-forming structure may comprise an elastically deformable material that is less rigid than the plenum chamber, and a portion of the seal-forming structure may substantially enclose the plenum chamber and the blower while allowing at least an inlet of the blower to remain exposed, (v) the seal-forming structure may be shaped and dimensioned and the elastically deformable material of the seal-forming structure may be selected to at least partially isolate the patient's head from vibration and dampen sound generated by the blower in use, (w) the RPT system may comprise a cover comprising an elastically deformable material that is less rigid than the plenum chamber that substantially encloses the plenum chamber and the blower while allowing at least an inlet of the blower to remain exposed, (x) the cover may be shaped and dimensioned and the elastically deformable material of the cover may be selected to at least partially isolate the patient's head from vibration and dampen sound generated by the blower in use, (y) the RPT system may comprise a control system to control the blower in use, (z) the control system may comprise a flexible printed circuit board assembly (PCBA), the PCBA comprising a microprocessor, (aa) the microprocessor may be programmed to perform at least one of closed-loop pressure control based on sensed pressure data, flow rate estimation, and automatically adjusting expiration pressure relief, and/or (bb) the control system may comprise a drive circuit to control the power supply separately from the blower.

Another aspect of the present technology is directed to a blower for a respiratory pressure therapy (RPT) system, the blower being configured to generate a flow of gas at a therapeutic pressure of at least 6 cmH$_2$O above ambient air pressure. The blower may comprise: a motor having a first end and a second end; a shaft having a first shaft end extending from the first end of the motor and a second shaft end extending from the second end of the motor; a first impeller and a second impeller arranged in series on each of the first shaft end and the second shaft end such that both first impellers and both second impellers are driven simultaneously by the motor; a first stator corresponding to each of the first end of the motor and the second end of the motor, the first stator positioned downstream of the first impeller and upstream of the second impeller along the flow of gas generated by the blower in use; a second stator corresponding to each of the first end of the motor and the second end of the motor, the second stator positioned downstream of the second impeller along the flow of gas generated by the blower in use; an end cap shaped and dimensioned to at least partially enclose each first impeller and at least partially define a blower inlet; a blower outlet positioned downstream of each second stator; and a flow path for the flow of gas passing from each blower inlet, past each first impeller, through each first stator, past each second impeller, through each second stator, and out each blower outlet.

In examples, (a) each first stator may comprise a plurality of first stator vanes to direct the flow of gas from the first impeller to the first stator opening in a radial direction, reduce the velocity of the flow of gas from the first impeller, and increase the pressure of the flow of gas from the first impeller, (b) the plurality of first stator vanes may comprise extended first stator vanes and short first stator vanes, the extended first stator vanes may extend further radially inward than the short first stator vanes, and the extended first stator vanes and the short first stator vanes may alternate circumferentially around the first stator, (c) the extended first stator vanes and the short first stator vanes each may comprise a curved portion that is swept backwards relative to the direction of rotation of the corresponding first impeller, and the extended first stator vanes and the short first stator vanes each may comprise a straight portion that extends radially inward from the curved portion, the straight portion of each of the extended first stator vanes may extend radially inward further than the straight portion of each of the short first stator vanes, (d) each first stator may comprise a first stator opening downstream of the plurality of first stator vanes to direct the flow of gas to the second impeller, (e) each first stator may comprise a first stator upper shroud to direct the flow of gas from the first impeller to the first stator opening in an axial direction, the corresponding first impeller positioned adjacent to the first stator upper shroud, (f) each first stator may comprise a first stator housing, and each second impeller and each second stator may be at least partially contained within the corresponding first stator housing such that the flow of gas travelling along the flow path past the second impeller and through the second stator also passes through the first stator housing, (g) each first stator housing may at least partially define the corresponding blower outlet, (h) each first stator housing may comprise a mounting structure to connect the blower to the RPT system, (i) each mounting structure may comprise a pair of mounting rails extending around the outer circumference of each first stator housing, (j) each end cap may be constructed to dampen sound and vibration, (k) each end cap may comprise a rigid material to provide structural integrity and a less rigid, elastically deformable material overmolded to the rigid material to dampen sound and vibration, (l) each first impeller and each second impeller may comprise an impeller hub, impeller vanes extending radially from the impeller hub, and an impeller shroud, (m) each of the impeller vanes may comprise a first impeller vane portion that extends only in a radial direction and a second impeller vane portion that extends in a radial and axial direction, (n) the first impeller vane portion of each of the impeller vanes of each first impeller and each second impeller may have a constant cross-section and may be radially inward relative to the second impeller vane portion, the second impeller vane portion may have a variable cross-section and may be radially outward relative to the first impeller vane portion, and the constant cross-section of the first impeller vane portion may be thinner than the variable cross-section of the second impeller vane portion, (o) each impeller shroud may comprise a first impeller shroud portion that extends only in a radial direction and a second impeller shroud portion that extends in a radial and axial direction, (p) the impeller vanes of each first impeller and each second impeller may be swept forward relative to the direction of rotation during operation, (q) each second stator may comprise a top ring, a base ring, and a plurality of second stator vanes that join the top ring and the base ring, and the plurality of second stator vanes may direct the flow of gas from the second impeller to the blower outlet in a radial and axial direction, reduce the velocity of the flow of gas from the second impeller, and increase the pressure of the flow of gas from the second impeller, (r) each of the plurality of second stator vanes may have a constant depth in a radial direction and an increasing width in a circumferential direction from the top ring to the base ring, and/or (s) each top ring may include a top ring recess and each base ring may include a base ring recess, the top ring recess and the base ring recess may allow a flexible printed circuit board assembly (PCBA) to pass therethrough.

Another aspect of the present technology is directed to a blower for a respiratory pressure therapy (RPT) system, the blower being configured to generate a flow of air at a therapeutic pressure of at least 6 cmH$_2$O above ambient air pressure. The blower may comprise: a motor having a first end and a second end; a shaft having a first shaft end extending from the first end of the motor and a second shaft end extending from the second end of the motor; an impeller arranged on each of the first shaft end and the second shaft end such that both impellers are driven simultaneously by the motor; a stator corresponding to each of the first end of the motor and the second end of the motor, the stator positioned downstream of the impeller along the flow of air generated by the blower in use; a blower outlet positioned downstream of each stator; a housing corresponding to each of the first end of the motor and the second end of the motor, each housing being shaped and dimensioned to at least partially enclose each impeller and each stator and at least partially define a blower inlet, and each housing at least partially defining the corresponding blower outlet such that the blower outlets are adjacent to one another; and a flow path for the flow of air passing from each blower inlet, past each impeller, through each stator, and out each blower outlet.

In examples, (a) each impeller and each second may be at least partially contained within the corresponding housing such that the flow of air travelling along the flow path past the impeller and through the stator also passes through the housing, (b) each housing may at least partially define the corresponding blower outlet, (c) each housing may comprise a mounting structure to connect the blower to the RPT system, (d) each mounting structure may comprise a pair of mounting rails extending around the outer circumference of each housing, (e) each housing may be constructed to dampen sound and vibration, (f) each housing may comprise a rigid material to provide structural integrity and a less rigid, elastically deformable material overmolded to the rigid material to dampen sound and vibration, (g) each impeller may comprise an impeller hub, impeller vanes extending radially from the impeller hub, and an impeller shroud, (h) each of the impeller vanes may comprise a first impeller vane portion that extends only in a radial direction and a second impeller vane portion that extends in a radial and axial direction, (i) the first impeller vane portion of each of the impeller vanes of each first impeller and each second impeller may have a constant cross-section and may be radially inward relative to the second impeller vane portion, (j) the second impeller vane portion may have a variable cross-section and may be radially outward relative to the first impeller vane portion, (k) the constant cross-section of the first impeller vane portion may be thinner than the variable cross-section of the second impeller vane portion, (l) each impeller shroud may comprise a first impeller shroud portion that extends only in a radial direction and a second impeller shroud portion that extends in a radial and axial direction, (m) the impeller vanes of each impeller may be swept forward relative to the direction of rotation during operation, (n) each stator may comprise a top ring, a base ring, and a plurality of stator vanes that join the top ring and the base ring, (o) the plurality of stator vanes may direct the flow of air from the impeller to the blower outlet in a radial and axial direction, reduce the velocity of the flow of air from the impeller, and increase the pressure of the flow of air from the impeller, (p) each of the plurality of stator vanes may have a constant depth in a radial direction and an increasing width in a circumferential direction from the top ring to the base ring, and/or (q) each top ring may include a top ring recess and each base ring may include a base ring recess, the top ring recess and the base ring recess allowing a flexible printed circuit board assembly (PCBA) to pass therethrough.

Another aspect of the present technology is directed to a vent assembly for discharging gas from a plenum chamber to atmosphere. The vent assembly includes: a base; at least one vent hole extension extending from the base and at least partially defining a passage; at least one vent hole passing through the at least one vent hole extension from the passage to atmosphere; and at least one flexible membrane attached to the at least one vent hole extension, the at least one flexible membrane being configured to cover the at least one vent hole in a closed position to prevent gas from being discharged from the passage to atmosphere, and the at least one flexible membrane being configured not to cover the at least one vent hole in an open position to allow gas to be discharged to atmosphere from the passage.

In examples, (a) the at least one vent hole extension may include an interior vent hole surface, each at least one vent hole passing through the interior vent hole surface to the passage, (b) the at least one flexible membrane may be attached to the at least one vent hole extension at the interior vent hole surface, (c) the at least one vent hole extension may include an exterior vent hole surface, each at least one vent hole passing through the exterior vent hole surface to atmosphere, (d) the at least one vent hole extension may comprise an internal surface, and the vent hole extension may have a generally triangular cross-section formed by the interior vent hole surface, the exterior vent hole surface, and the internal surface, (e) the interior vent hole surface may slope downwardly into the interior of the vent assembly relative to a flow of pressurized gas passing through the passage, (f) the at least one vent hole extension may comprises two diametrically opposed vent hole extensions, the at least one flexible membrane may comprise two flexible membranes, each of the two flexible membranes attached to a corresponding one of the two diametrically opposed vent hole extensions, and the vent assembly may comprise a divider positioned between the two diametrically opposed vent hole extensions to form a first passage and a second passage, (g) the two flexible membranes may not contact the divider in the open position, (h) the at least one flexible membrane may be constructed of an elastically deformable material, and/or (i) the at least one flexible membrane may be cantilevered to the at least one vent hole extension.

Another aspect of the present technology is directed to a respiratory pressure therapy (RPT) system comprising: at least one housing portion at least partially defining a plenum chamber pressurisable to a therapeutic pressure of at least 6 cmH$_2$O above ambient air pressure; a seal-forming structure constructed and arranged to form a seal with a region of the patient's face at or surrounding an entrance to the patient's airways such that a flow of air at said therapeutic pressure is delivered to at least the entrance to the patient's nares, the seal-forming structure constructed and arranged to maintain said therapeutic pressure in the plenum chamber throughout the patient's respiratory cycle in use; a positioning and stabilising structure constructed and arranged to provide an elastic force to hold the seal-forming structure in a therapeutically effective position on the patient's head, the positioning and stabilising structure comprising a tie, a lateral portion of the tie being constructed and arranged to overlie a region of the patient's head superior to the otobasion superior in use, and a superior portion of the tie being constructed and arranged to overlie a region of the patient's head in a region of the parietal bone in use, wherein the positioning and stabilising structure has a non-rigid decoupling portion; a blower configured to generate the flow of air and pressurise the plenum chamber to the therapeutic pressure, the blower having a motor, the blower being connected to the plenum chamber such that in use the blower is suspended from the patient's head and an axis of rotation of the motor is generally perpendicular to the patient's sagittal plane; and a power supply configured to provide electrical power to the blower, wherein the at least one housing portion comprises the vent assembly of described in the examples of the two preceding paragraphs.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

4 BRIEF DESCRIPTION OF THE DRAWINGS

The present technology is illustrated by way of example, and not by way of limitation, in the figures of the accompanying drawings, in which like reference numerals refer to similar elements including:

4.1 Treatment Systems

FIG. 1 shows a system including a patient 1000 wearing a patient interface 3000, in the form of nasal pillows, receiving a supply of air at positive pressure from an RPT device 4000. Air from the RPT device 4000 is humidified in a humidifier 5000, and passes along an air circuit 4170 to the patient 1000. A bed partner 1100 is also shown. The patient is sleeping in a supine sleeping position.

4.2 Respiratory System and Facial Anatomy

FIG. 2 shows an overview of a human respiratory system including the nasal and oral cavities, the larynx, vocal folds, oesophagus, trachea, bronchus, lung, alveolar sacs, heart and diaphragm.

4.3 Patient Interface

FIG. 3 shows a patient interface in the form of a nasal mask in accordance with one form of the present technology.

4.4 RPT Device

4.5 Breathing Waveforms

Figure 5:
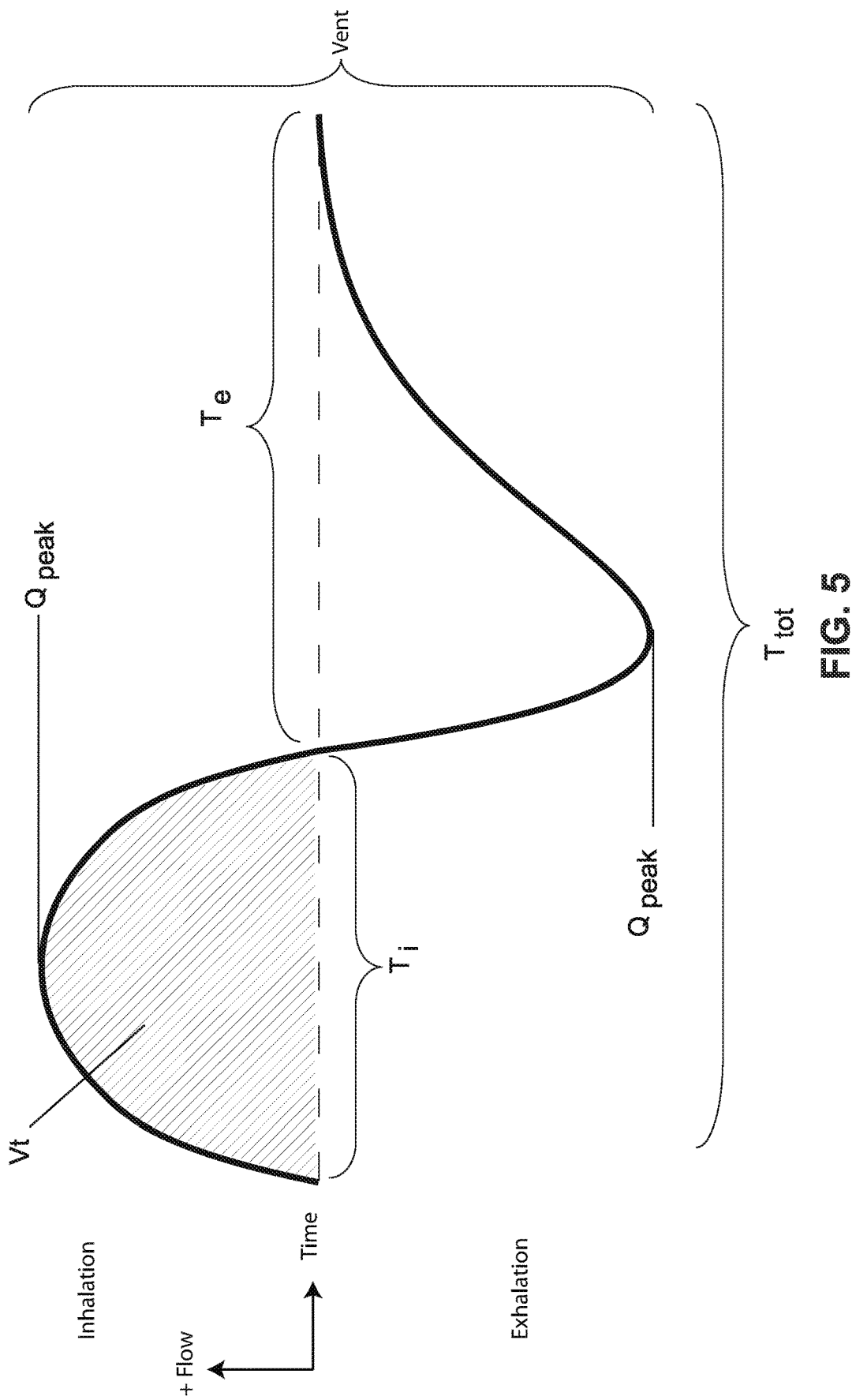

FIG. 5 shows a model typical breath waveform of a person while sleeping.

4.6 Respiratory Pressure Therapy (RPT) System

Figure 6A:
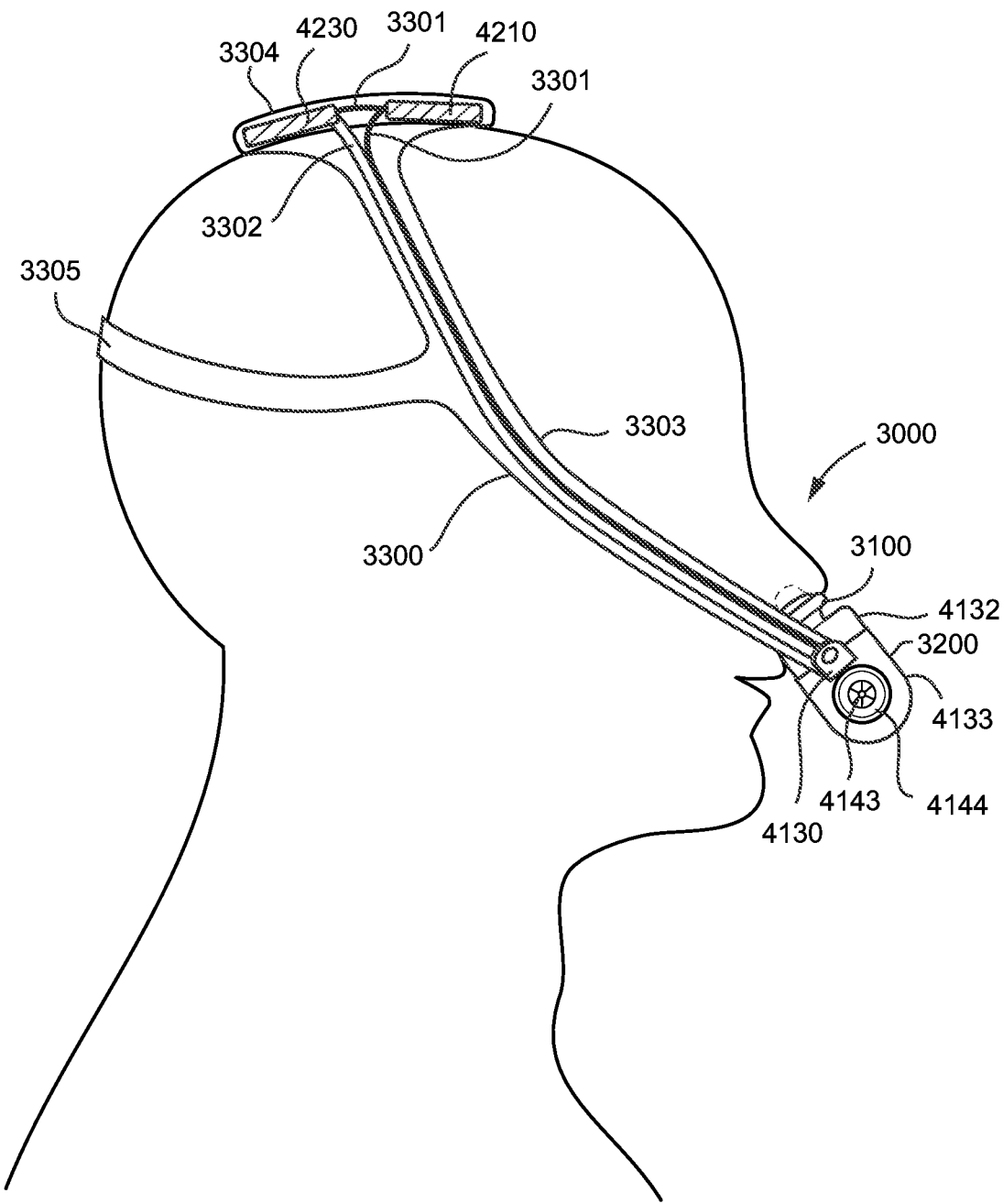

FIG. 6A depicts a side schematic view of a patient wearing an RPT system according to an example of the present technology.

Figure 6B:
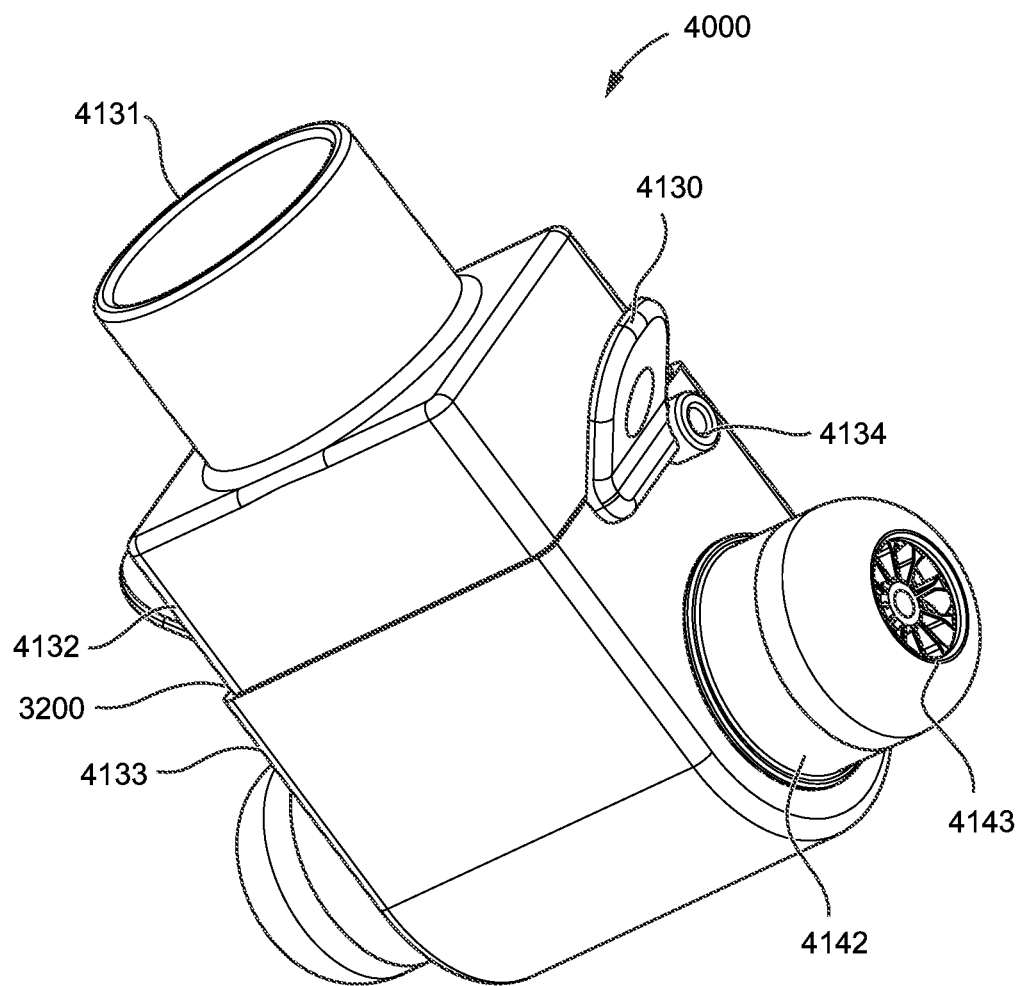

FIG. 6B depicts a perspective view of the pressure generating features of an RPT system according to an example of the present technology.

Figure 6C:
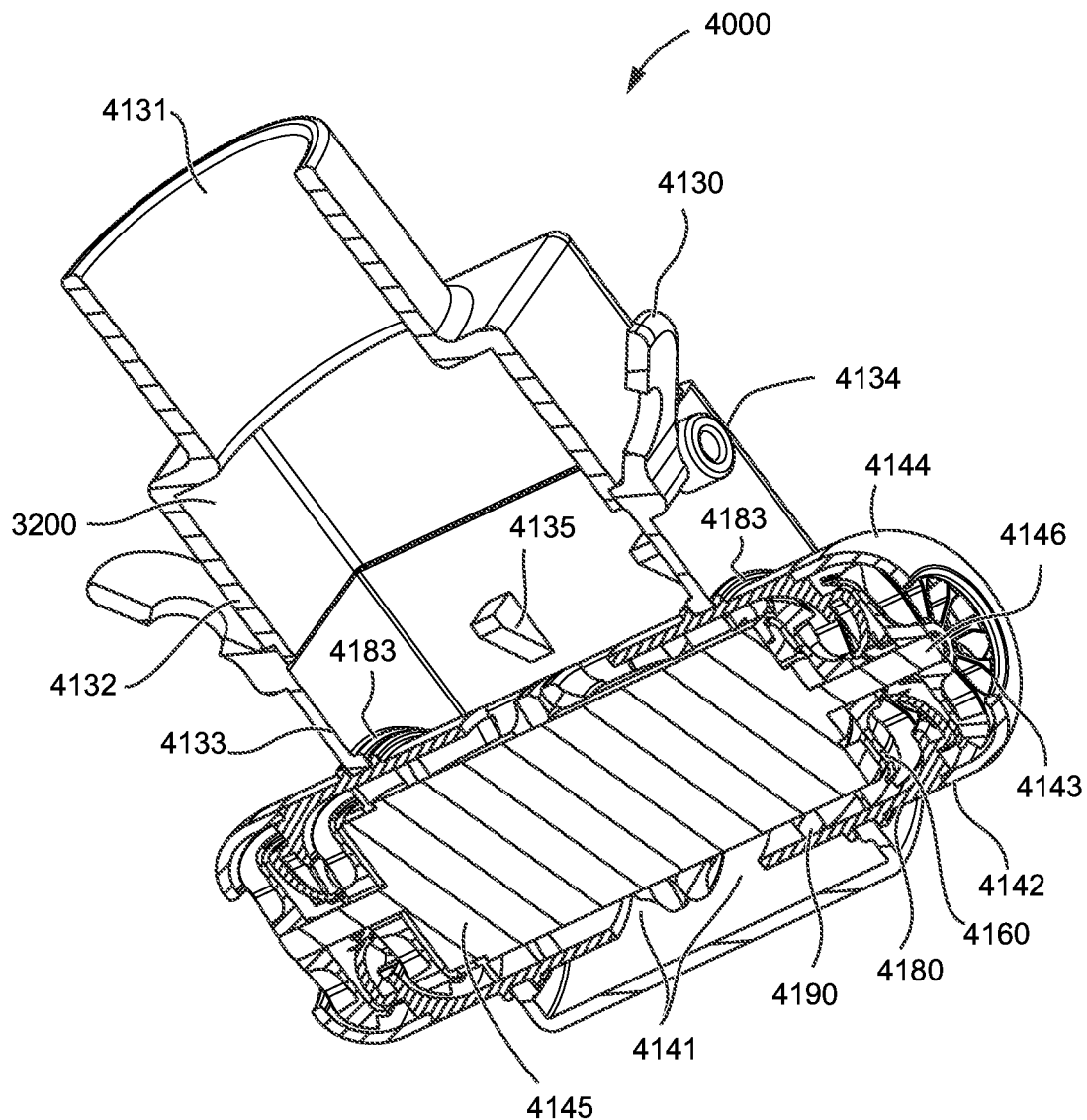

FIG. 6C depicts a cross-sectional view of the pressure generating features of an RPT system according to an example of the present technology.

Figure 6D:
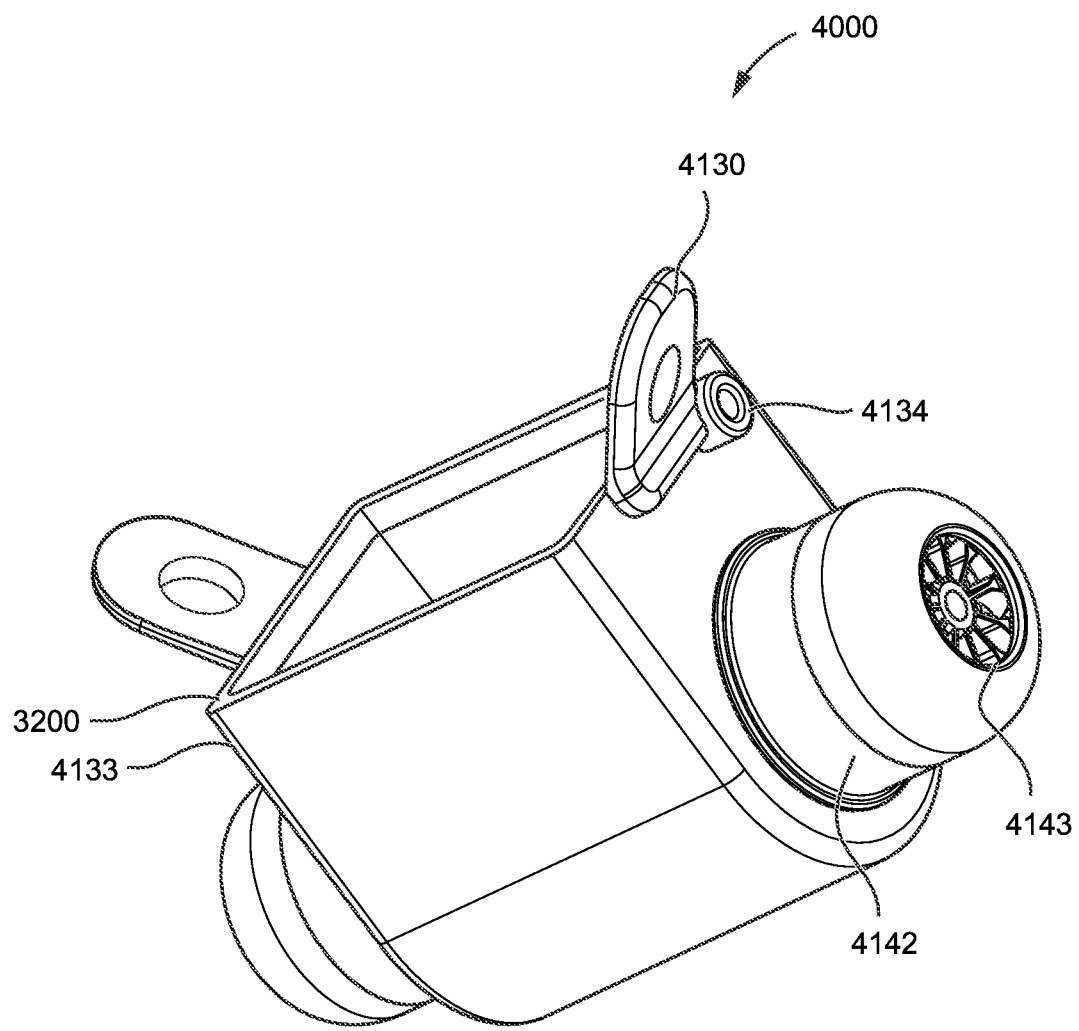

FIG. 6D depicts a perspective view of the pressure generating features of an RPT system according to another example of the present technology.

Figure 6E:
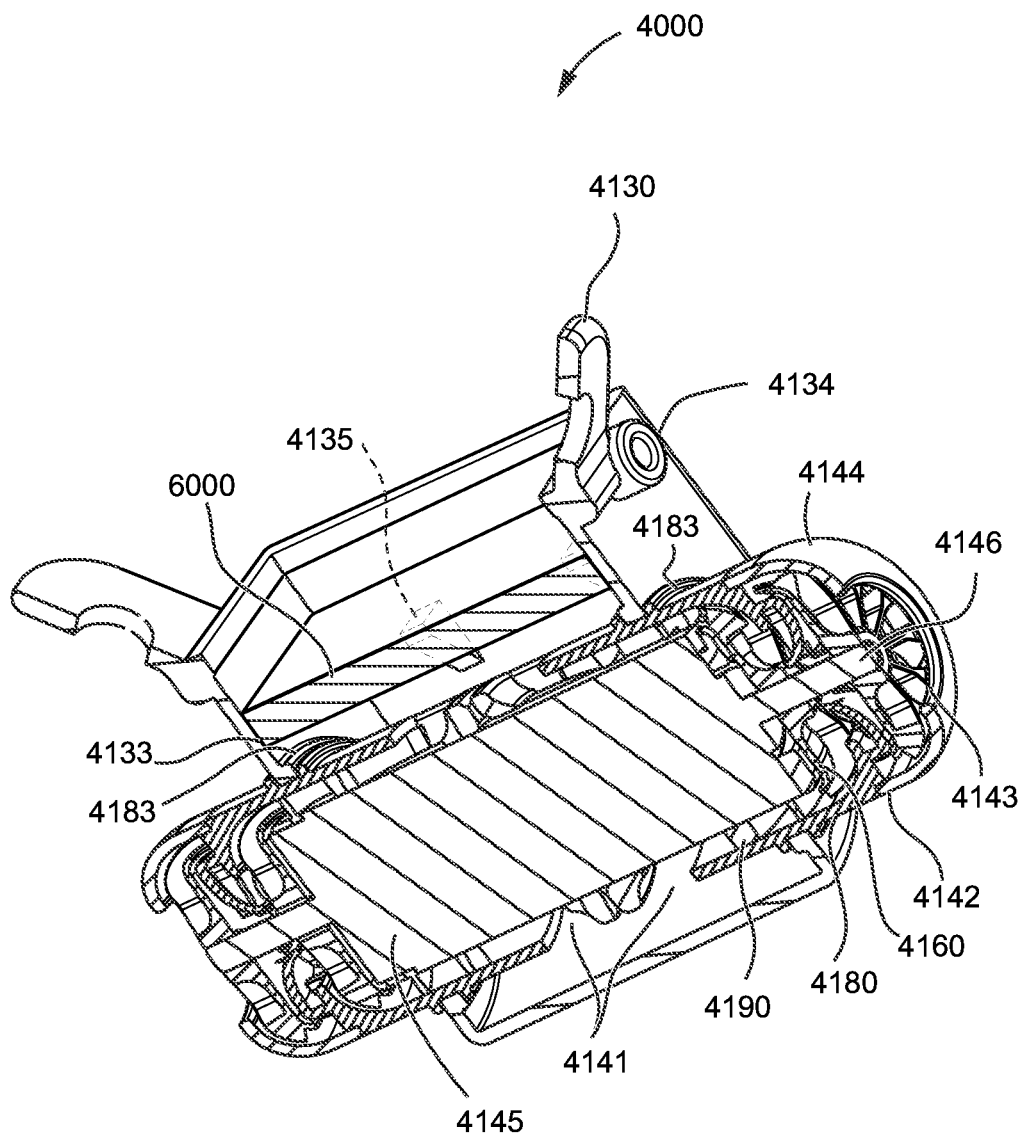

FIG. 6E depicts a cross-sectional view of the pressure generating features of an RPT system according to another example of the present technology.

Figure 7A:
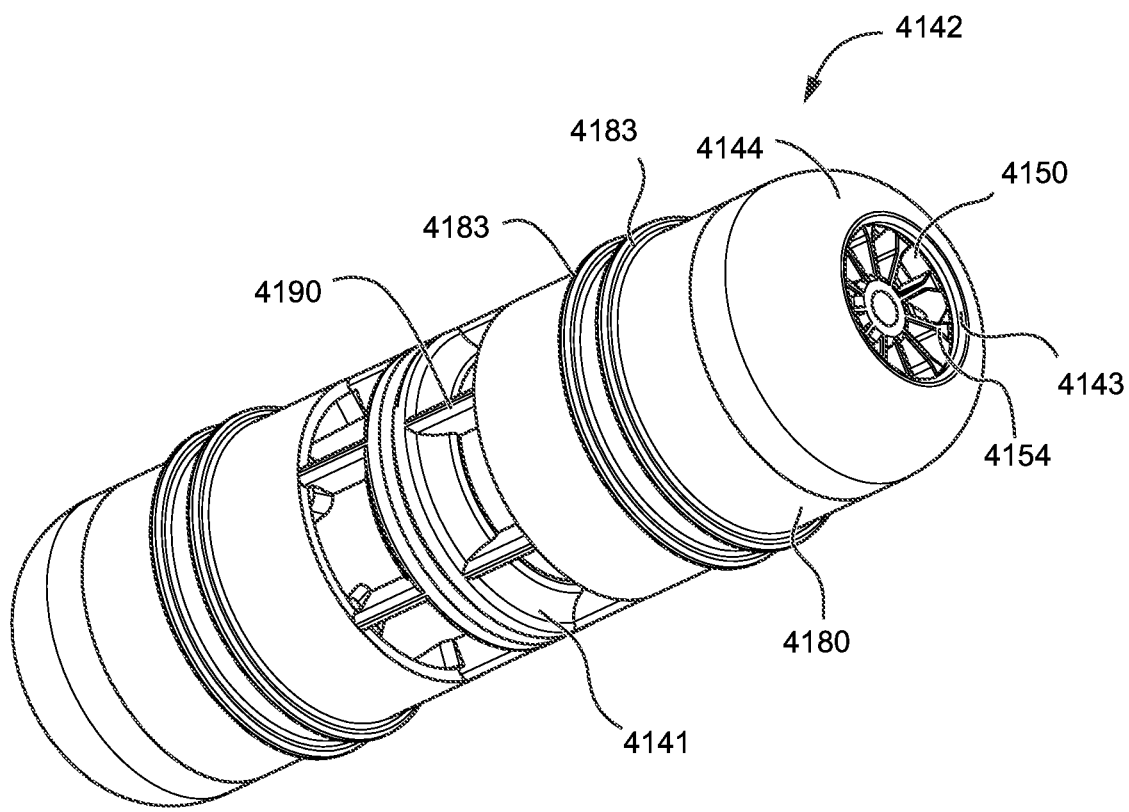

FIG. 7A depicts a perspective view of a blower of an RPT system according to an example of the present technology.

Figure 7B:
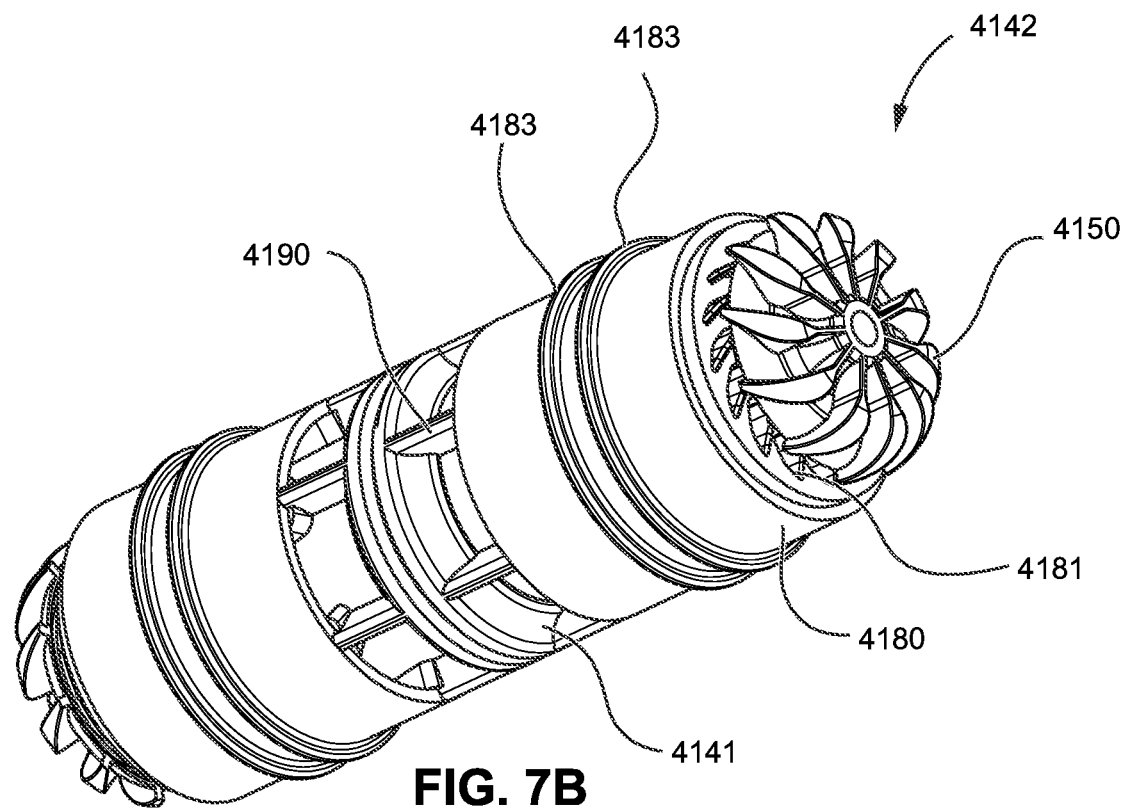

FIG. 7B depicts a perspective view of a partially disassembled blower of an RPT system according to an example of the present technology.

Figure 7C:
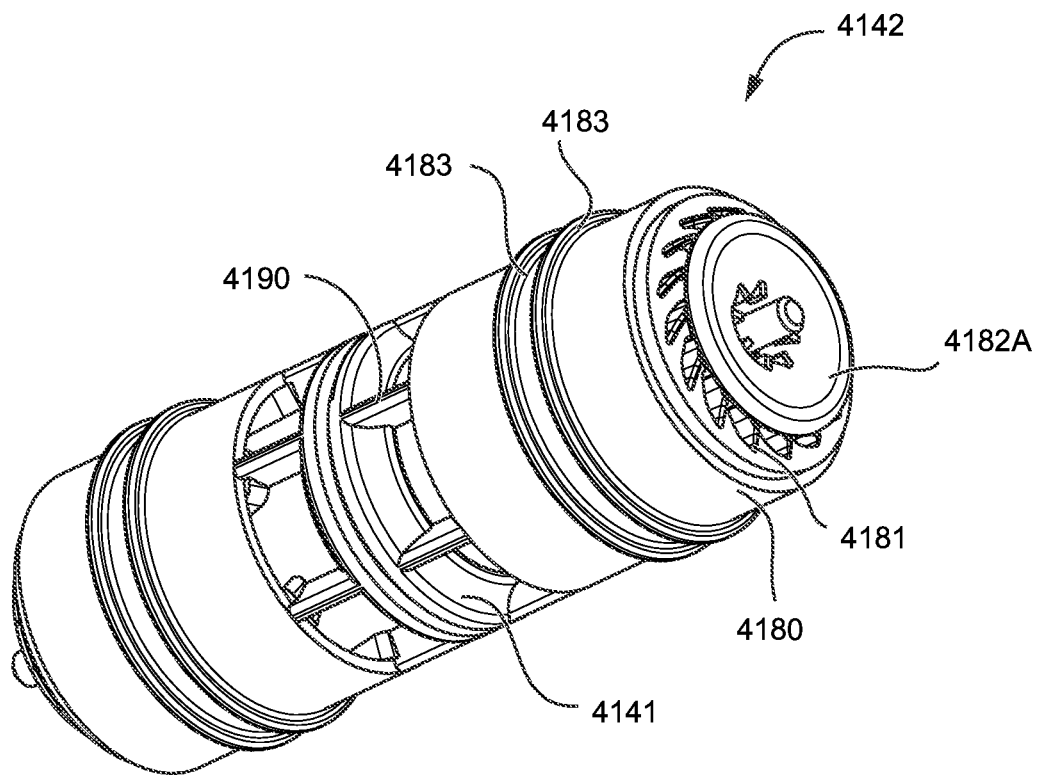

FIG. 7C depicts another perspective view of a partially disassembled blower of an RPT system according to an example of the present technology.

Figure 7D:
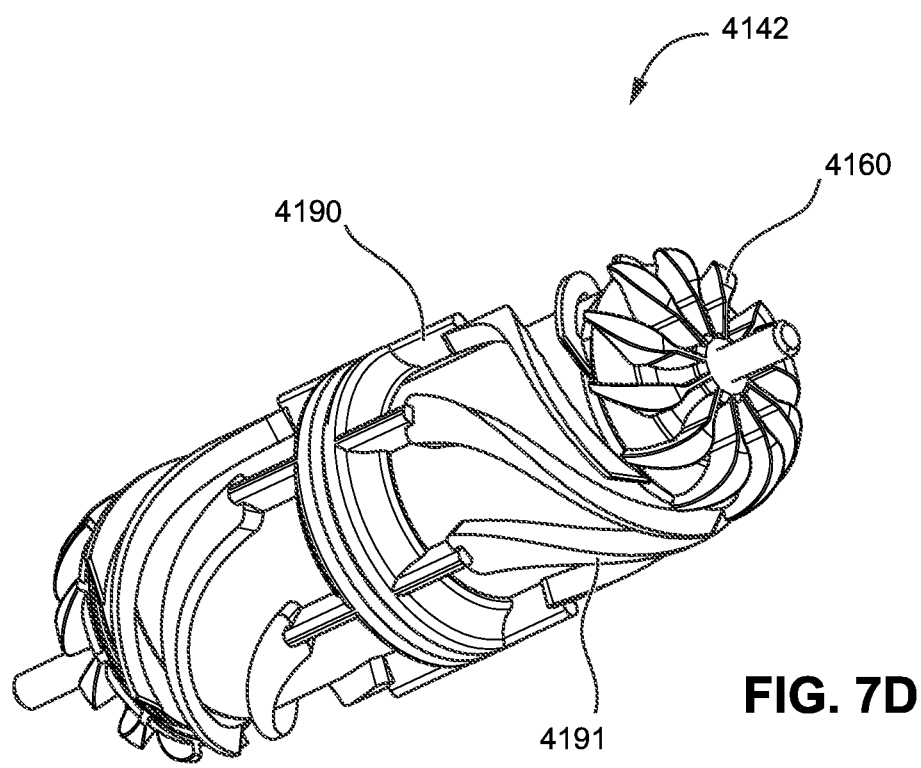

FIG. 7D depicts another perspective view of a partially disassembled blower of an RPT system according to an example of the present technology.

Figure 7E:
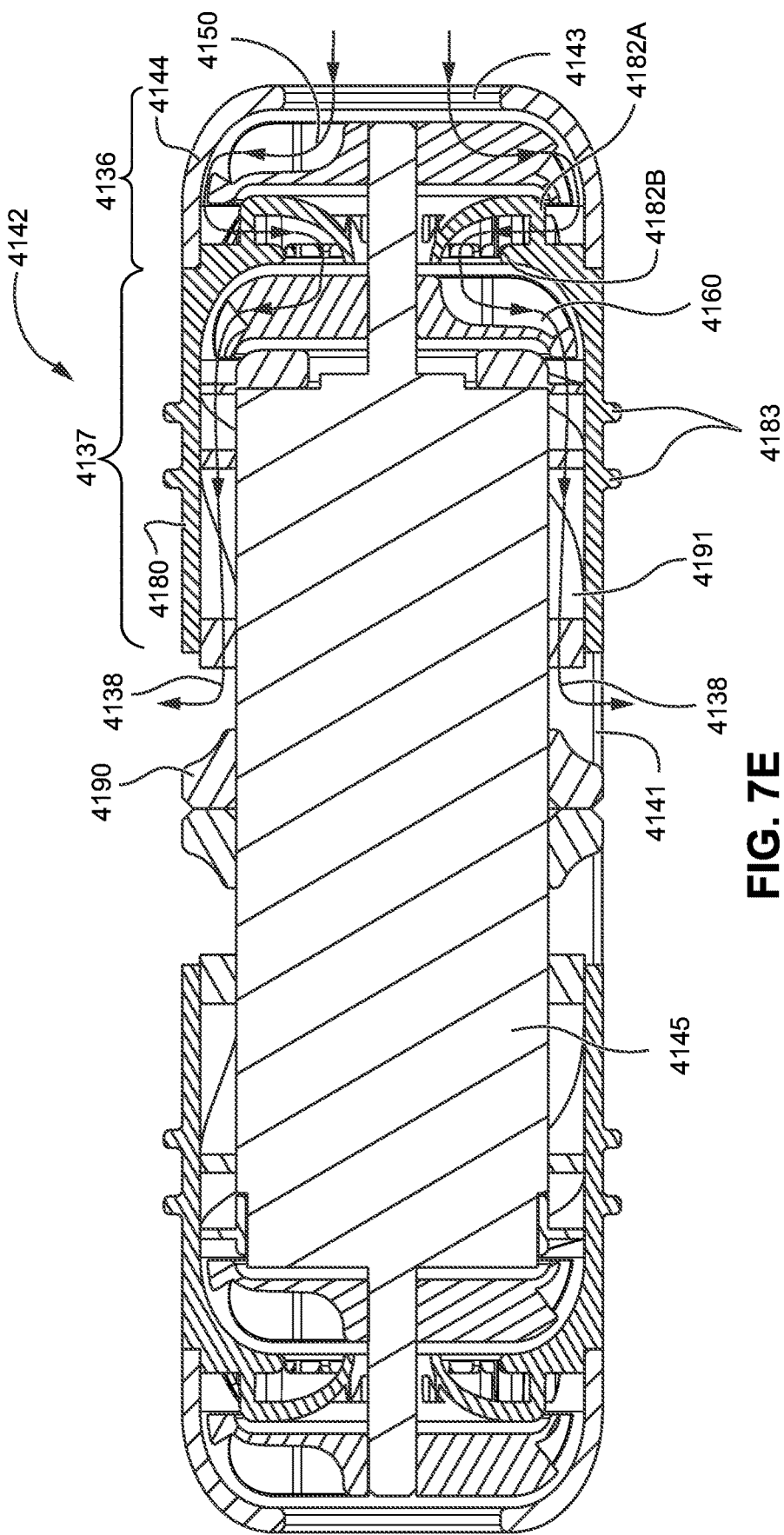

FIG. 7E depicts a cross-sectional view of a blower of an RPT system according to an example of the present technology.

Figure 7F:
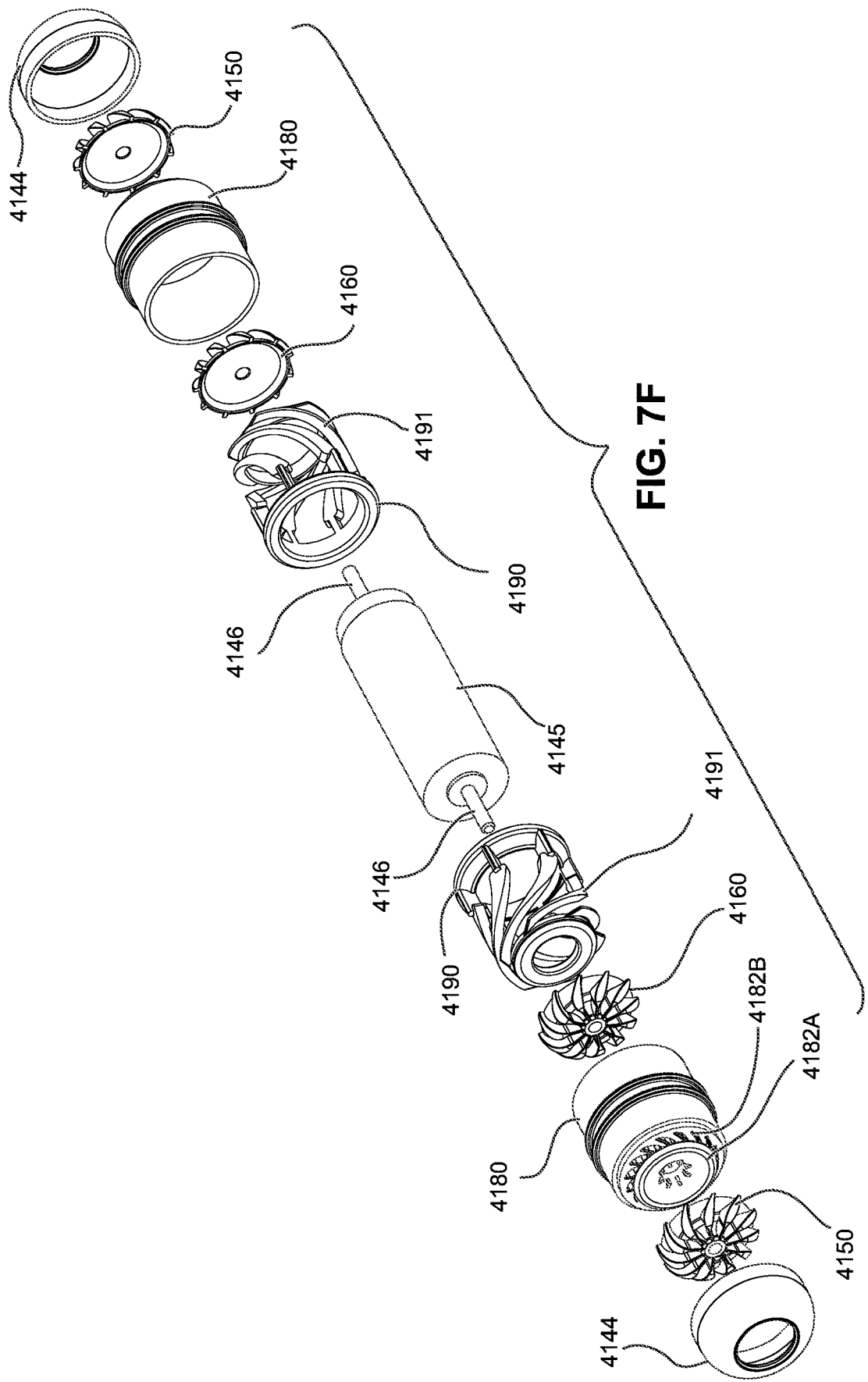

FIG. 7F depicts an exploded view of a blower of an RPT system according to an example of the present technology.

Figure 8A:
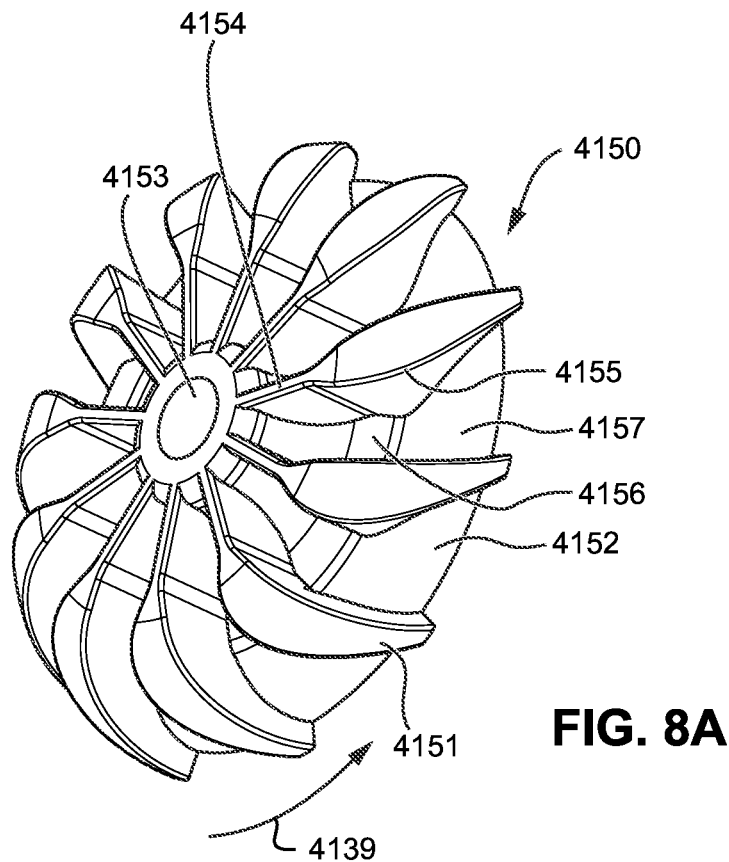

FIG. 8A depicts a perspective view of an impeller of a blower of an RPT system according to an example of the present technology.

Figure 8B:
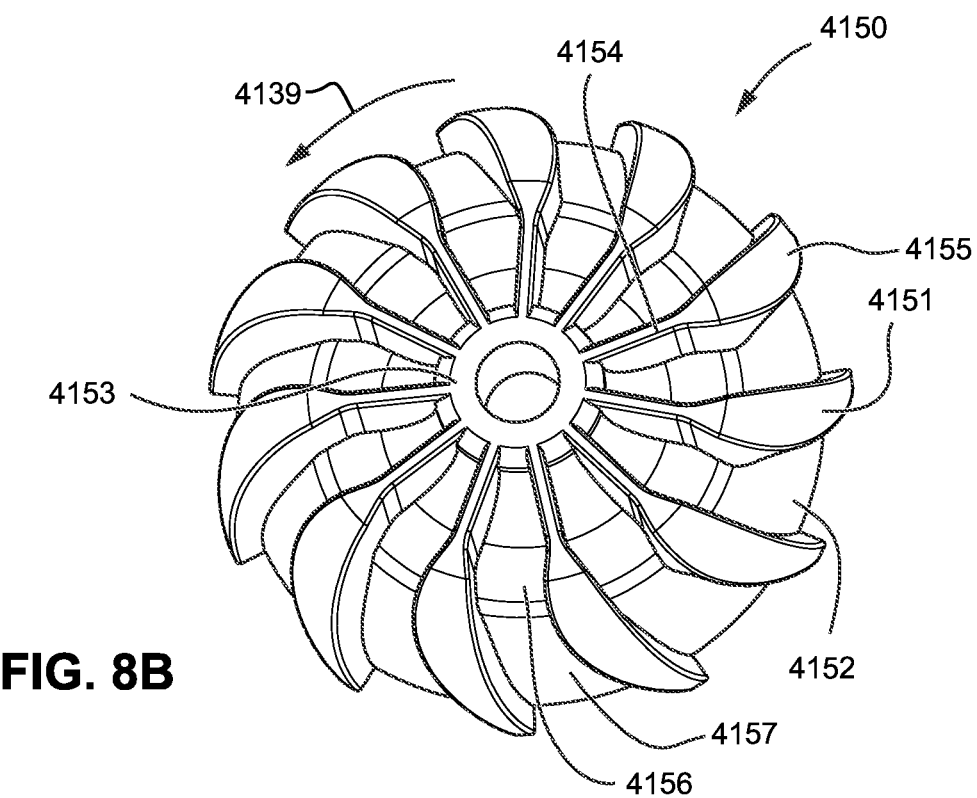

FIG. 8B depicts another perspective view of an impeller of a blower of an RPT system according to an example of the present technology.

Figure 8C:
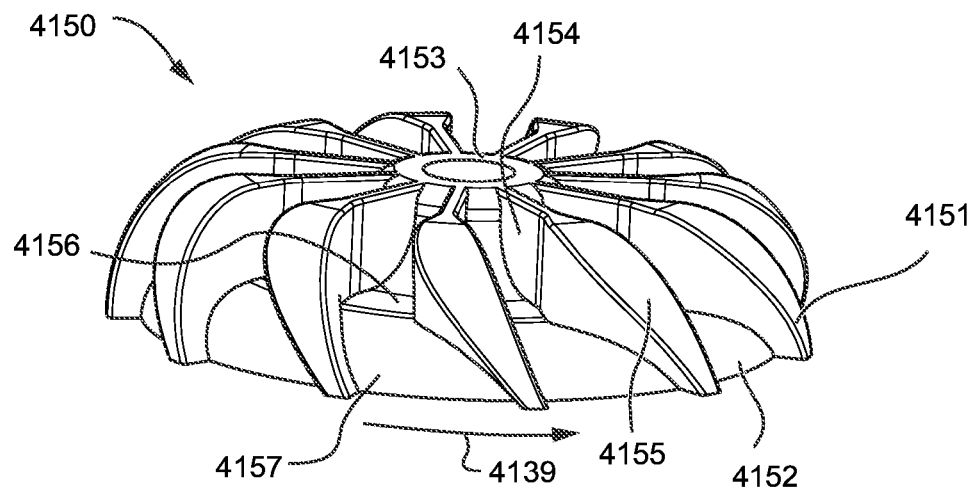

FIG. 8C depicts another perspective view of an impeller of a blower of an RPT system according to an example of the present technology.

Figure 8D:
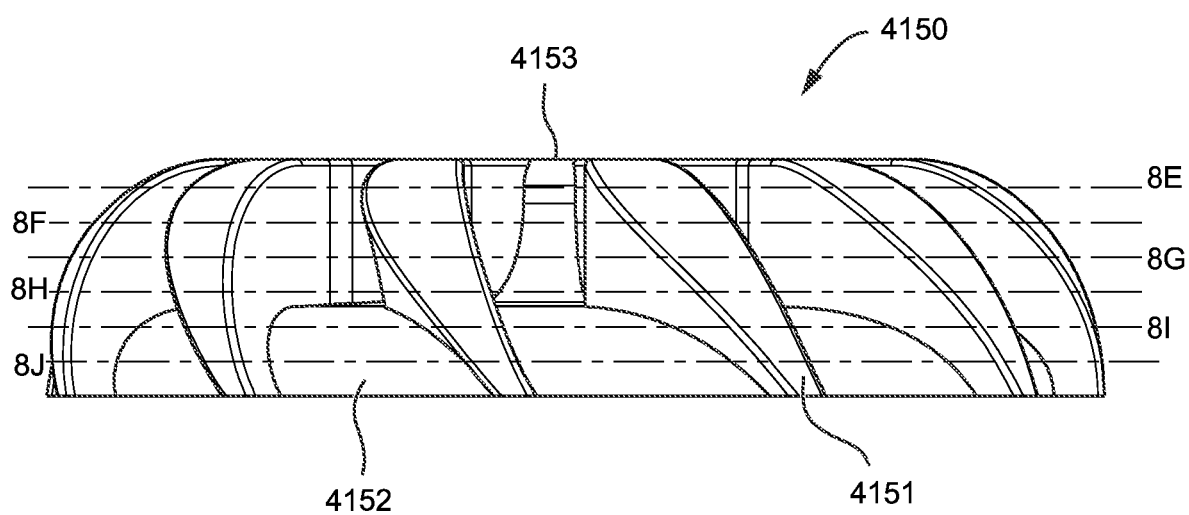

FIG. 8D depicts a side elevation view of an impeller of a blower of an RPT system according to an example of the present technology.

Figure 8E:
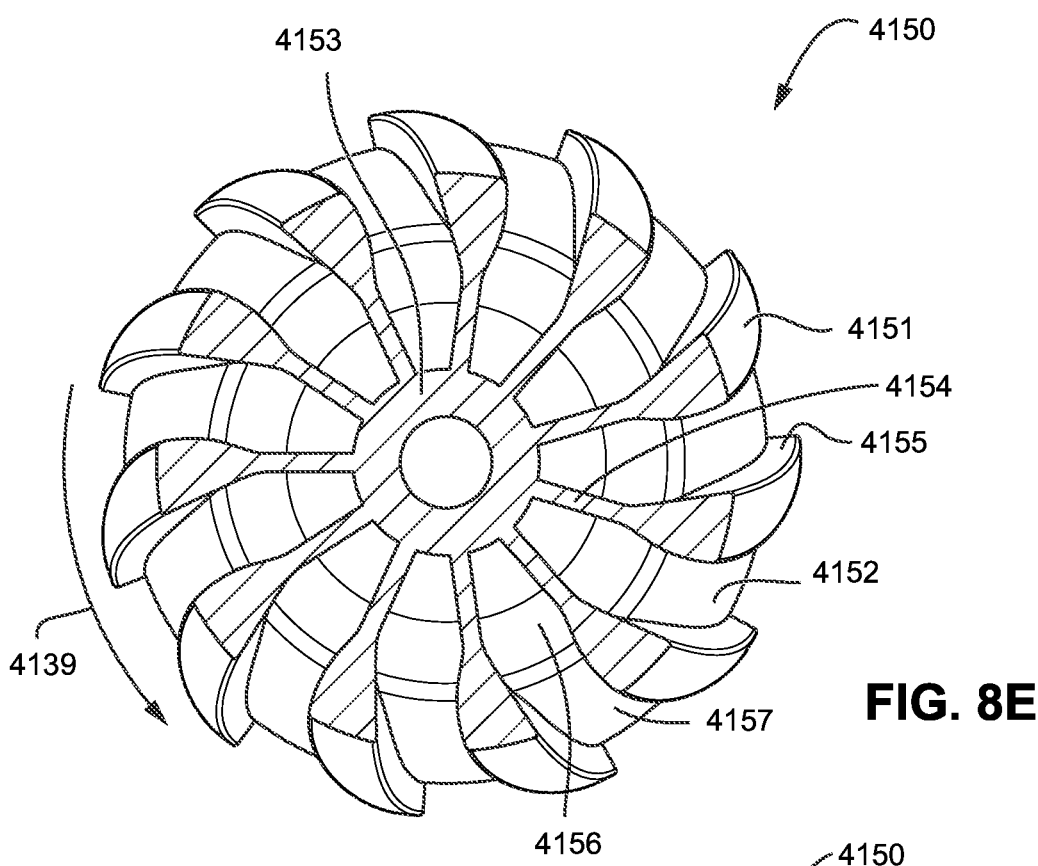

FIG. 8E depicts a cross-sectional view of an impeller of a blower of an RPT system taken through line 8E of FIG. 8D according to an example of the present technology.

Figure 8F:
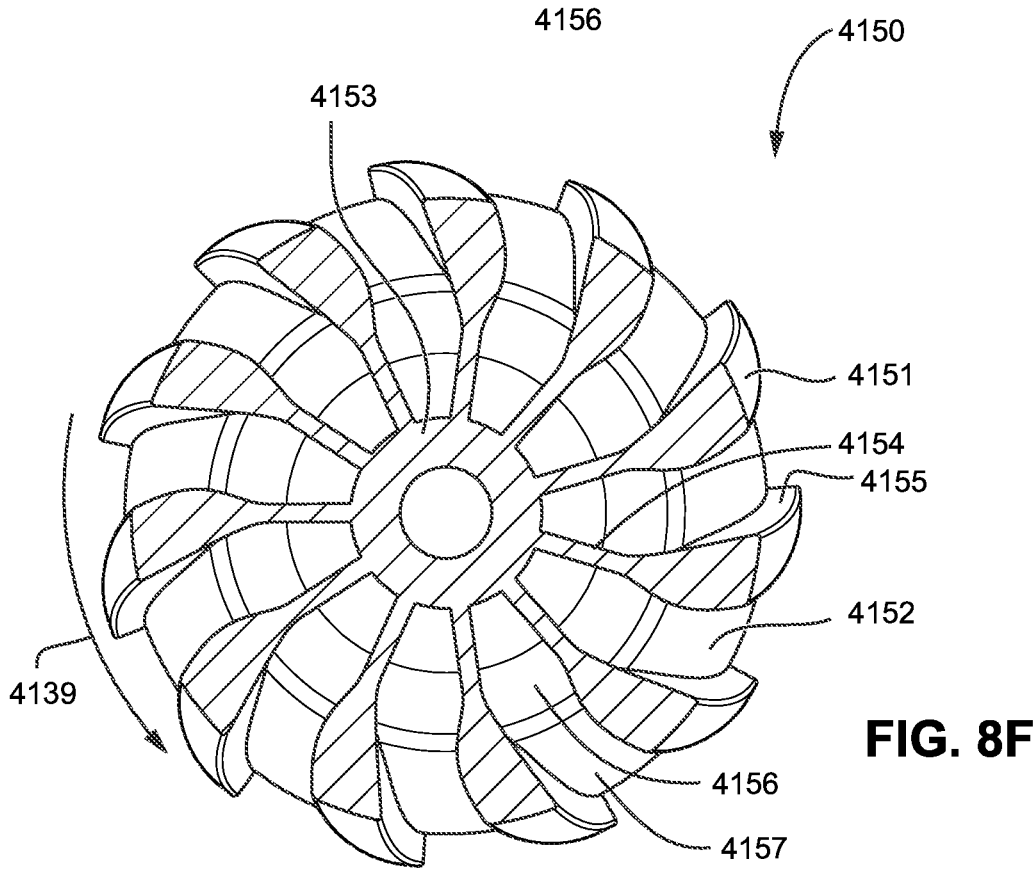

FIG. 8F depicts a cross-sectional view of an impeller of a blower of an RPT system taken through line 8F of FIG. 8D according to an example of the present technology.

Figure 8G:
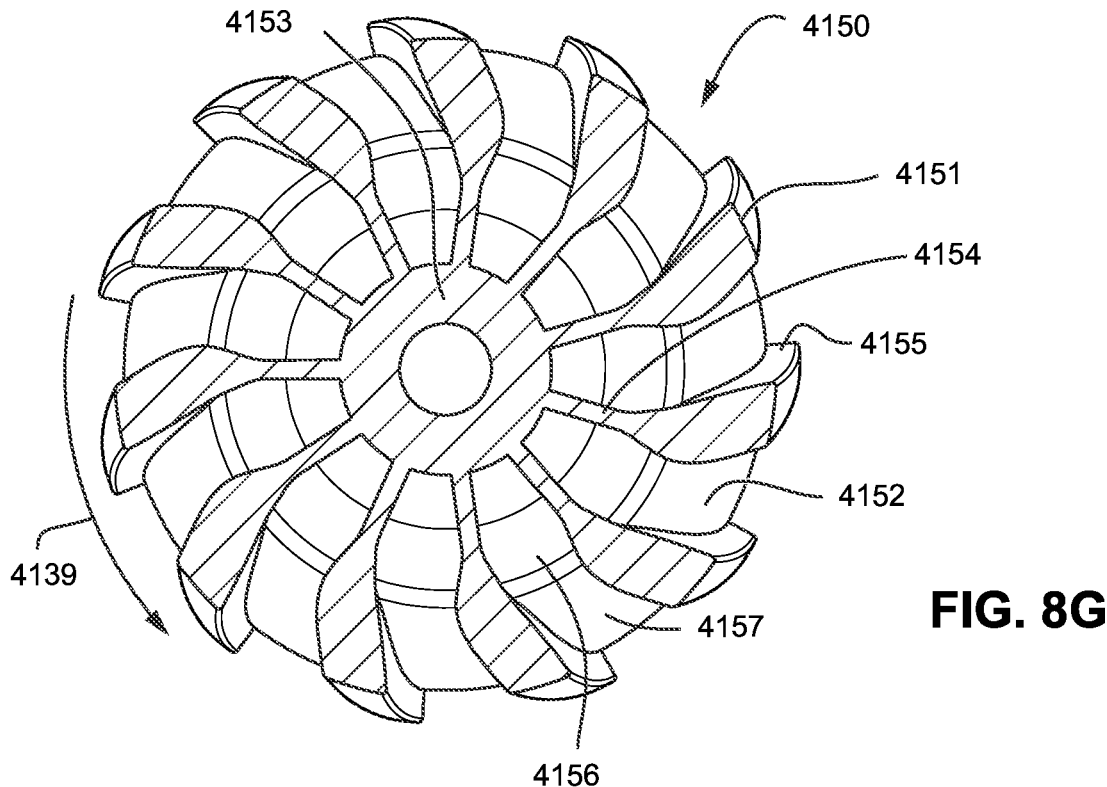

FIG. 8G depicts a cross-sectional view of an impeller of a blower of an RPT system taken through line 8G of FIG. 8D according to an example of the present technology.

Figure 8H:
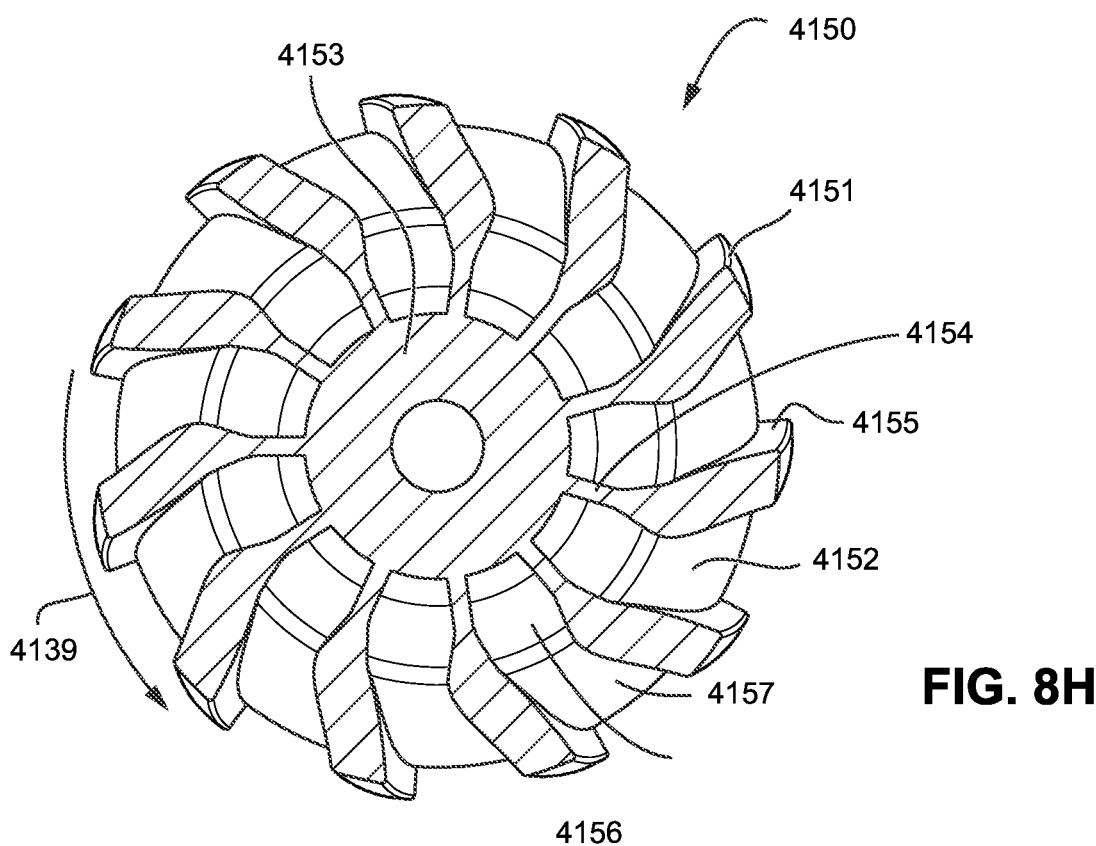

FIG. 8H depicts a cross-sectional view of an impeller of a blower of an RPT system taken through line 8H of FIG. 8D according to an example of the present technology.

Figure 8I:
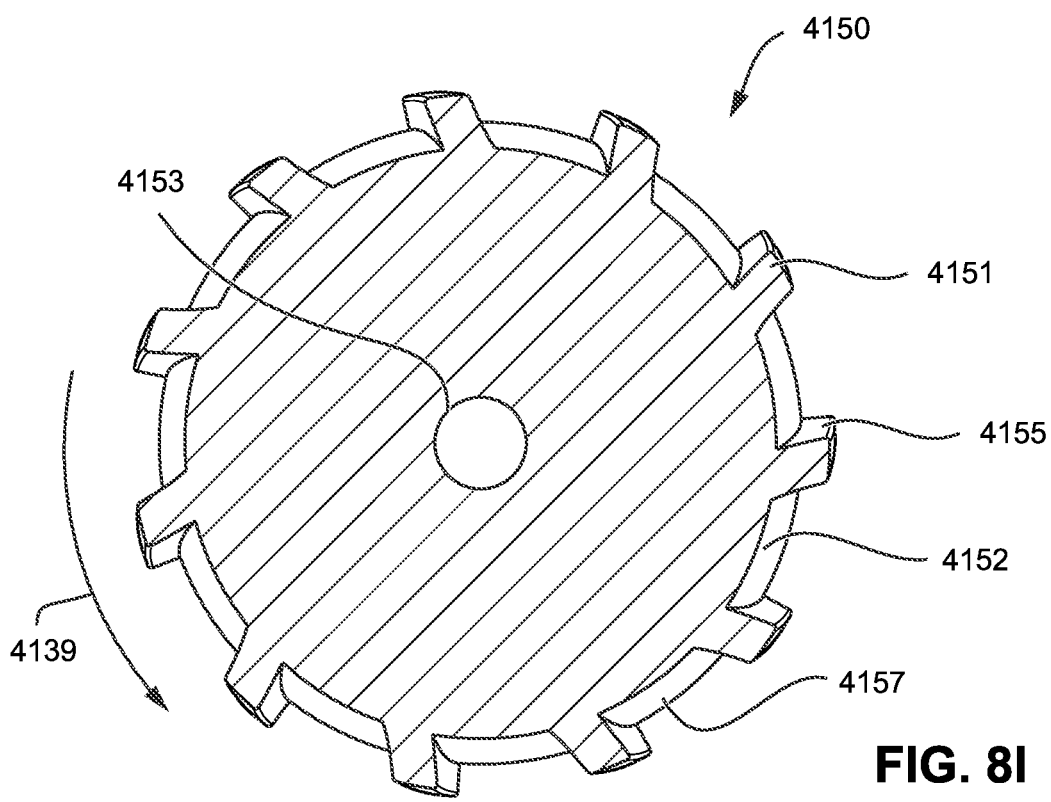

FIG. 8I depicts a cross-sectional view of an impeller of a blower of an RPT system taken through line 8I of FIG. 8D according to an example of the present technology.

Figure 8J:
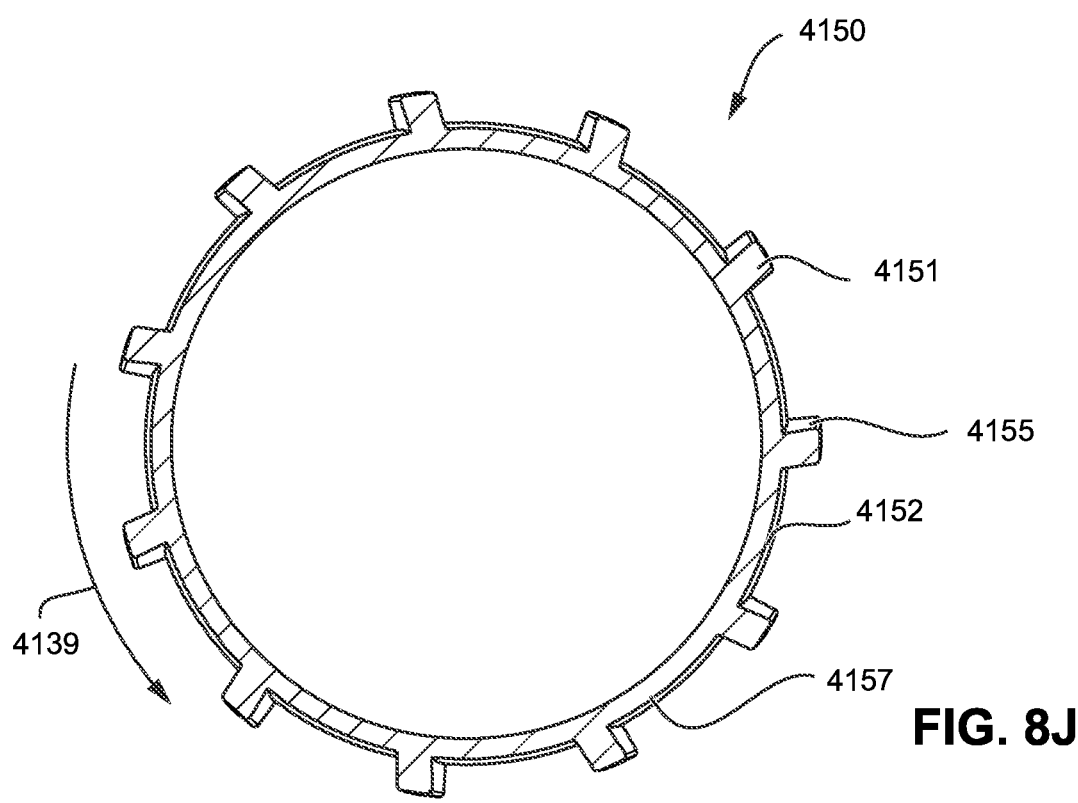

FIG. 8J depicts a cross-sectional view of an impeller of a blower of an RPT system taken through line 8J of FIG. 8D according to an example of the present technology.

Figure 8K:
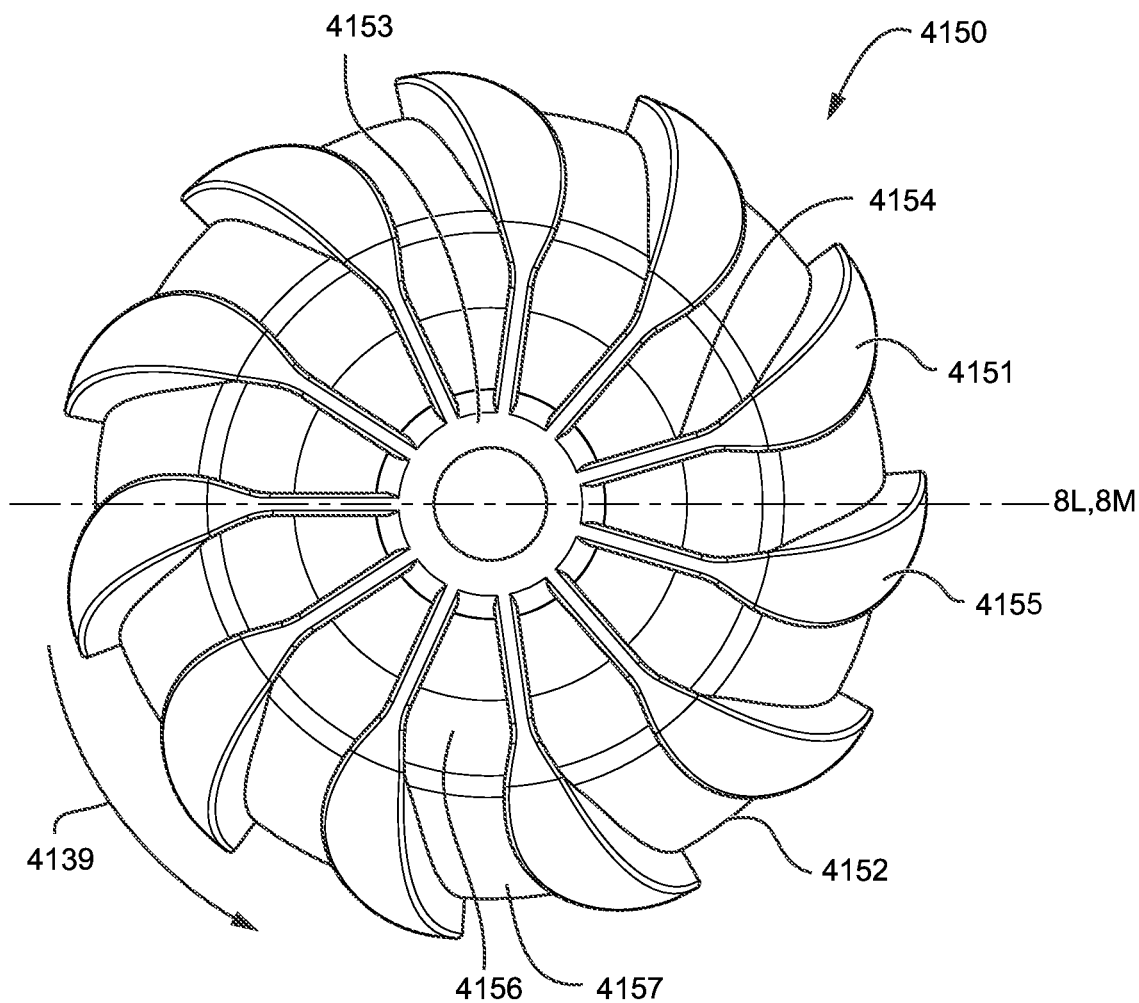

FIG. 8K depicts a plan view of an impeller of a blower of an RPT system according to an example of the present technology.

Figure 8L:
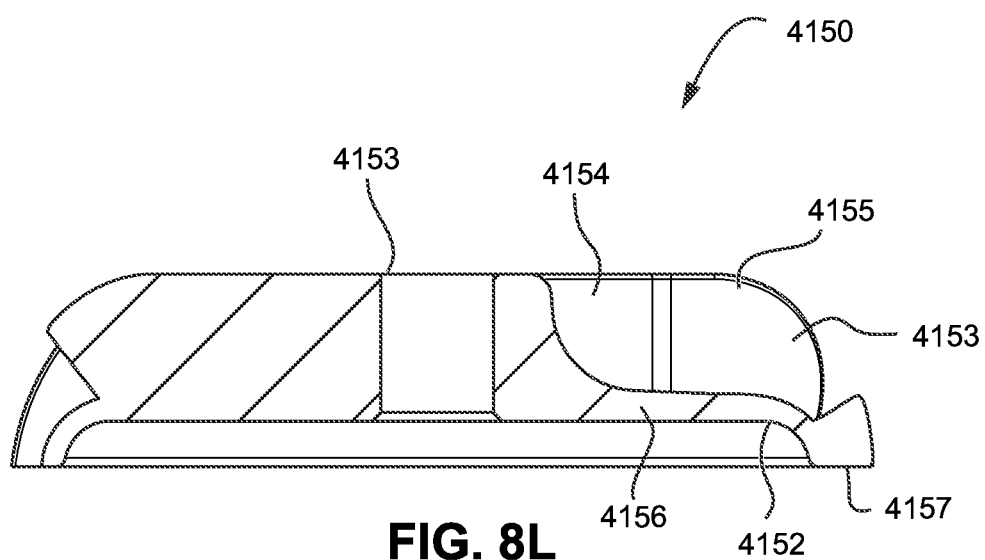

FIG. 8L depicts a cross-sectional view of an impeller of a blower of an RPT system taken through line 8L of FIG. 8K according to an example of the present technology.

Figure 8M:
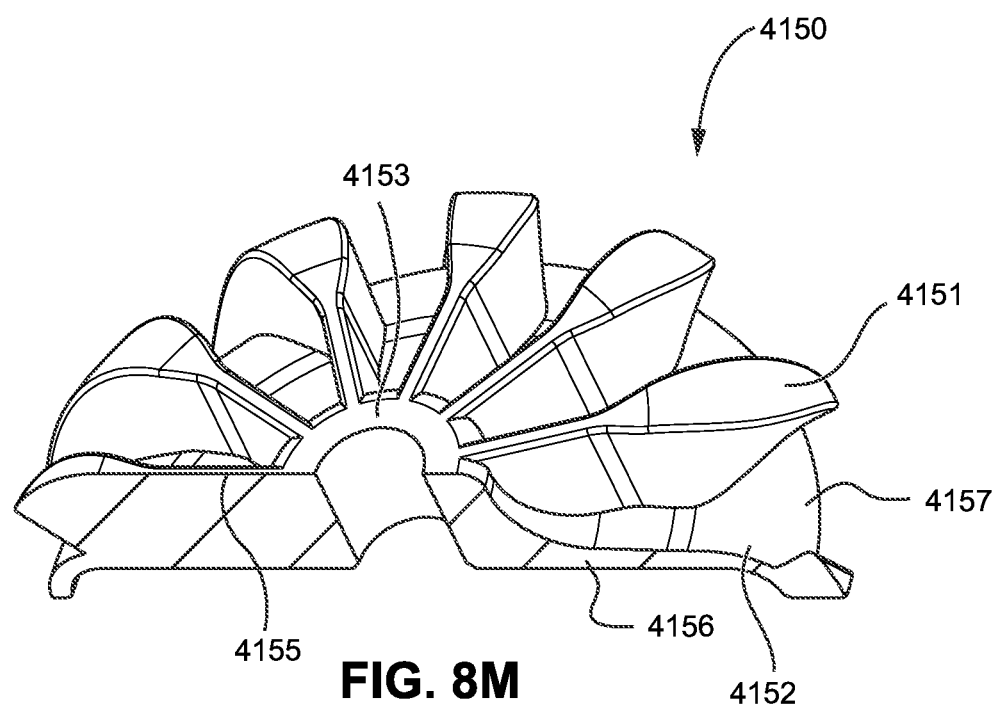

FIG. 8M depicts a cross-sectional view of an impeller of a blower of an RPT system taken through line 8M of FIG. 8K according to an example of the present technology.

Figure 9A:
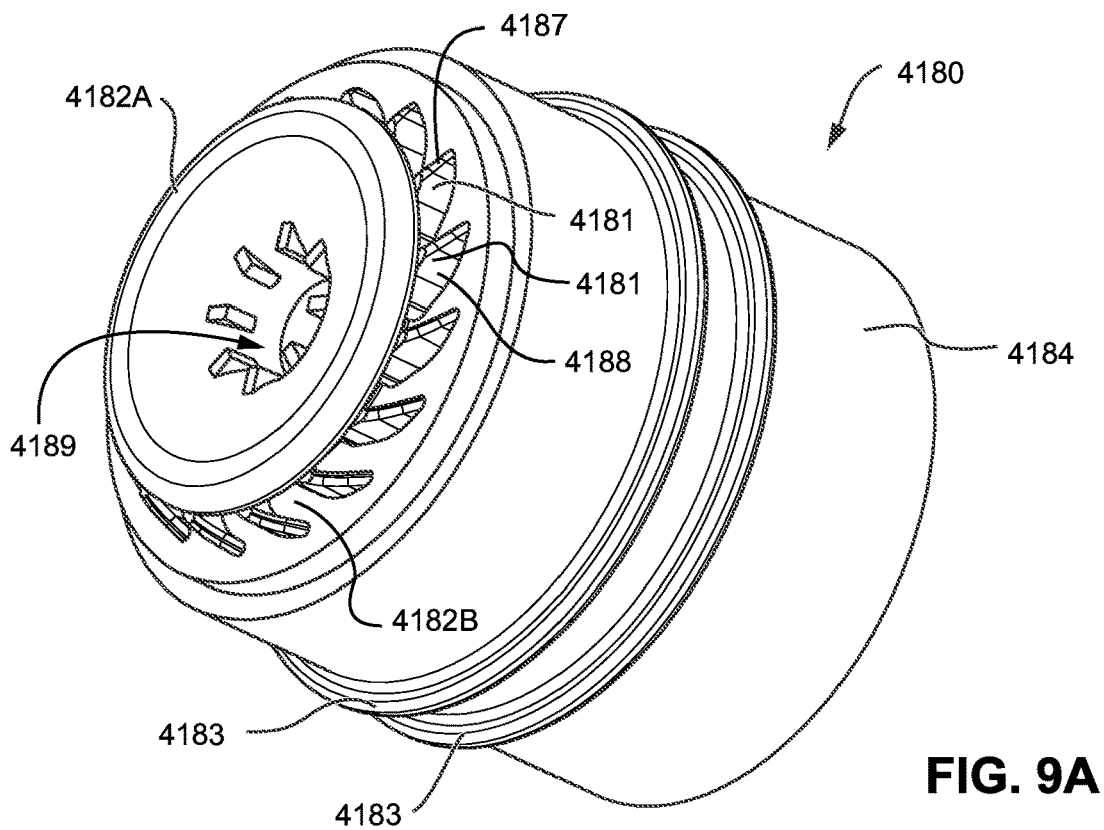

FIG. 9A depicts a perspective view of a first stator of a blower of an RPT system according to an example of the present technology.

Figure 9B:
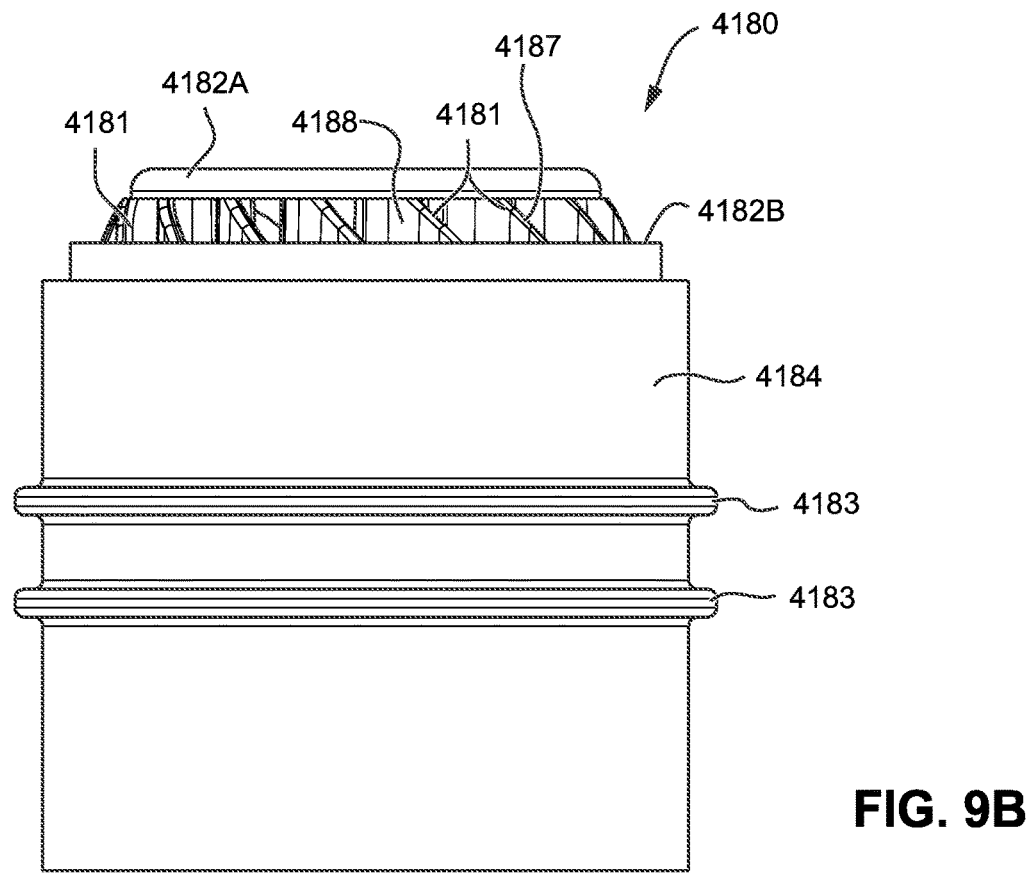

FIG. 9B depicts a side elevation view of a first stator of a blower of an RPT system according to an example of the present technology.

Figure 9C:
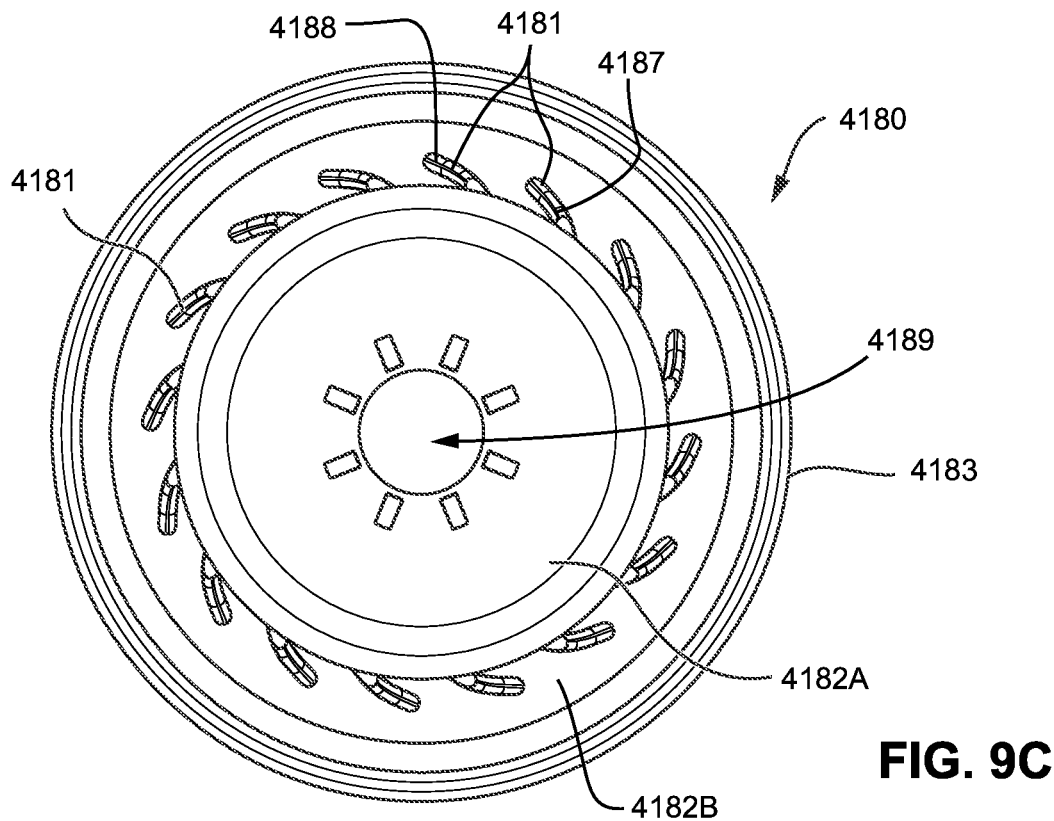

FIG. 9C depicts a plan view of a first stator of a blower of an RPT system according to an example of the present technology.

Figure 9D:
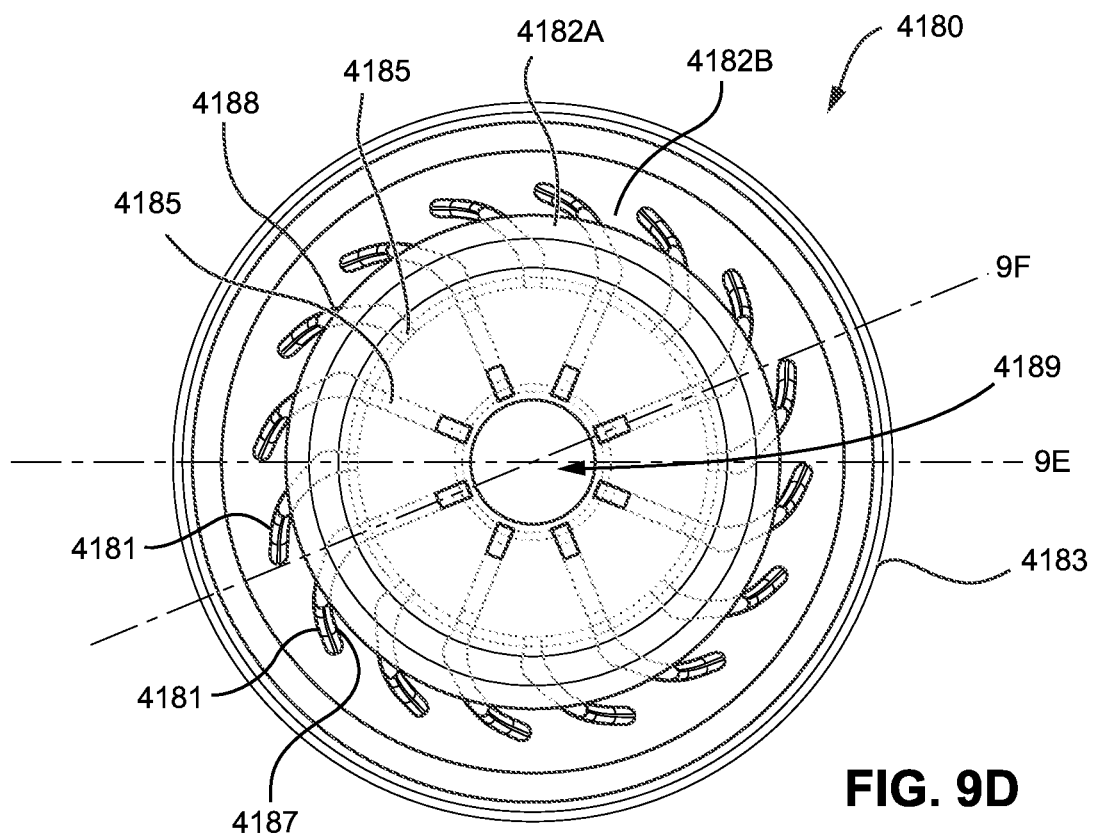

FIG. 9D depicts a plan view of a first stator of a blower of an RPT system with the stator upper shroud shown in phantom according to an example of the present technology.

Figure 9E:
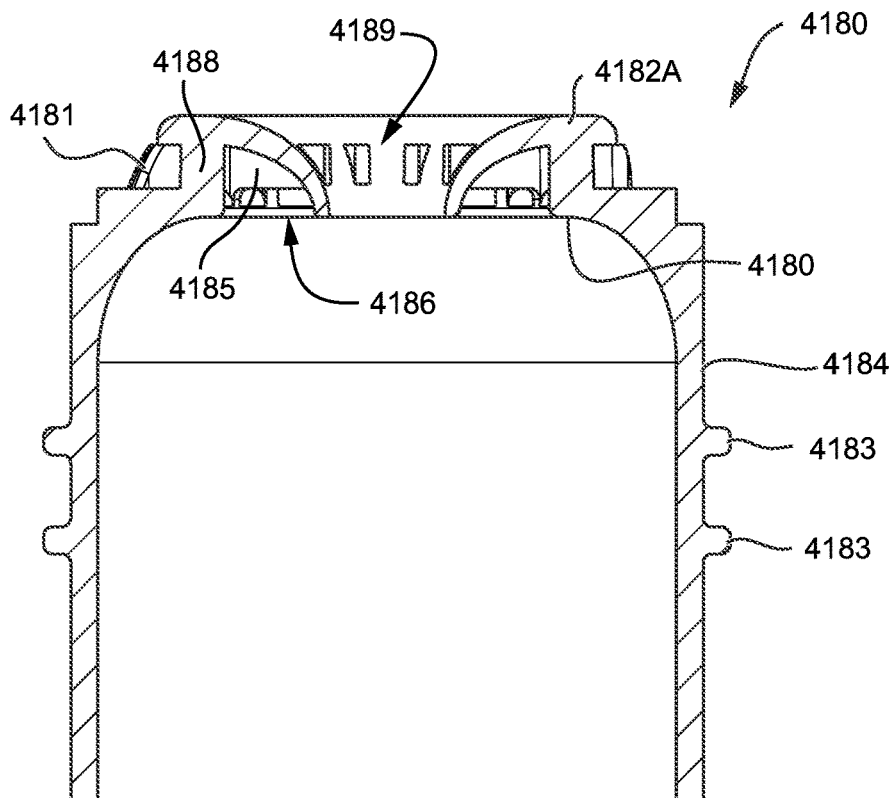

FIG. 9E depicts a cross-sectional view of a first stator of a blower of an RPT system taken through line 9E-9E of FIG. 9D according to an example of the present technology.

Figure 9F:
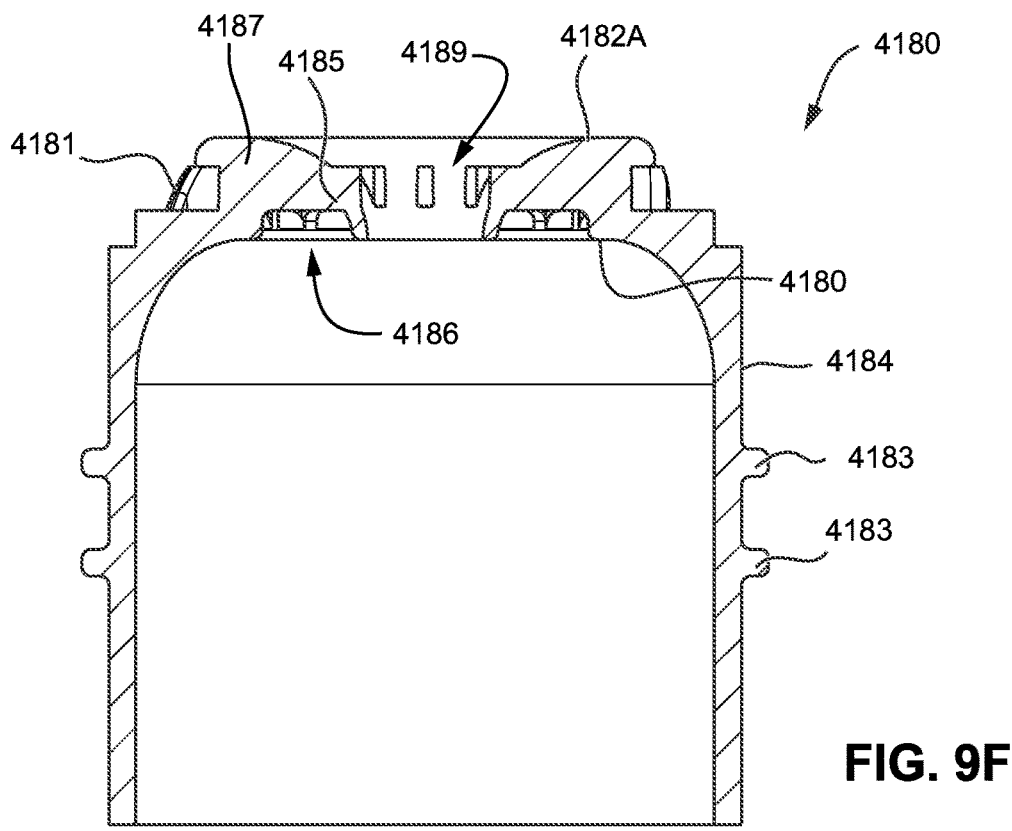

FIG. 9F depicts a cross-sectional view of a first stator of a blower of an RPT system taken through line 9F-9F of FIG. 9D according to an example of the present technology.

Figure 10A:
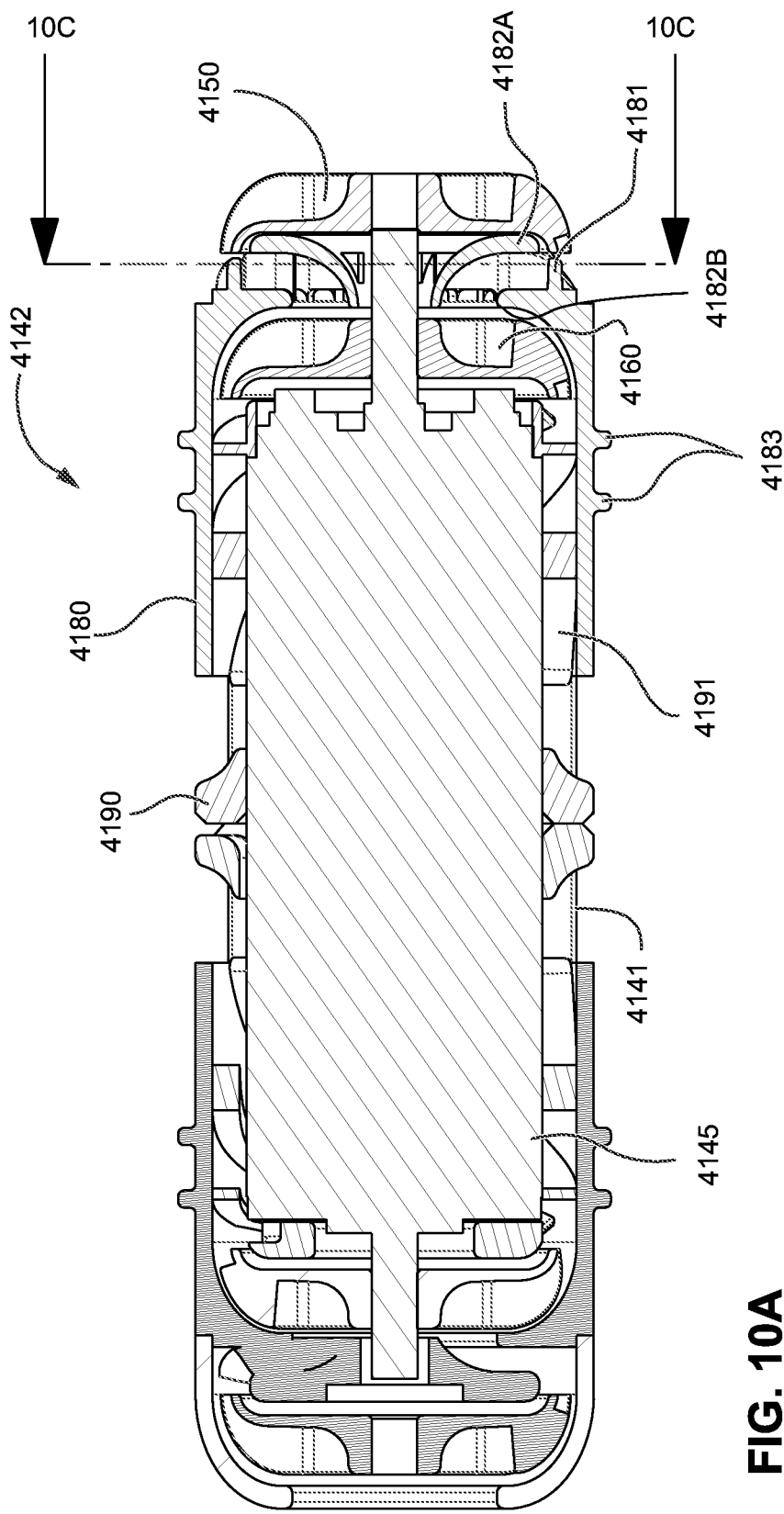

FIG. 10A depicts another cross-sectional view of a partially disassembled blower of an RPT system according to an example of the present technology.

Figure 10B:
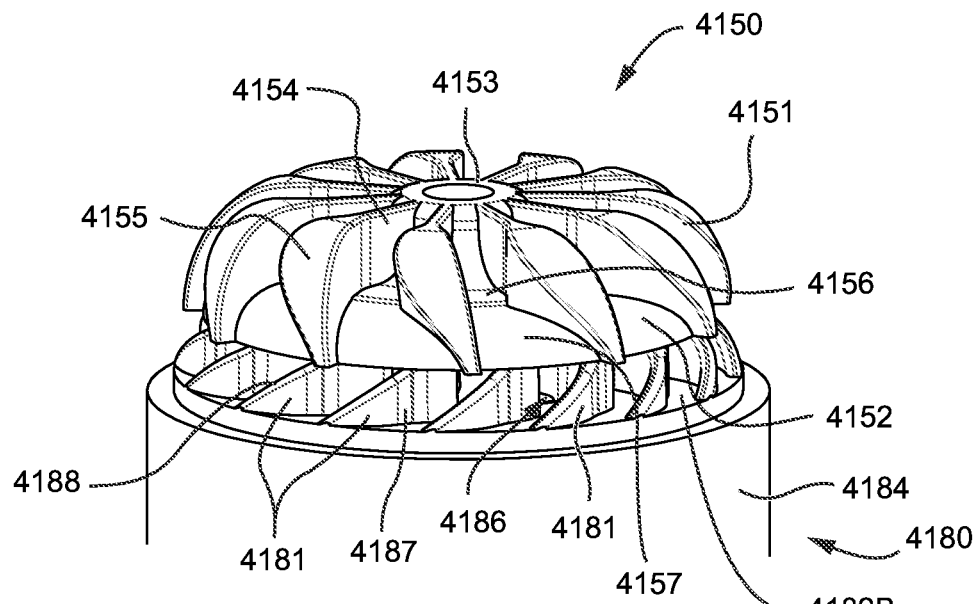

FIG. 10B depicts a perspective view of an end of a partially disassembled blower of an RPT system according to an example of the present technology.

Figure 10C:
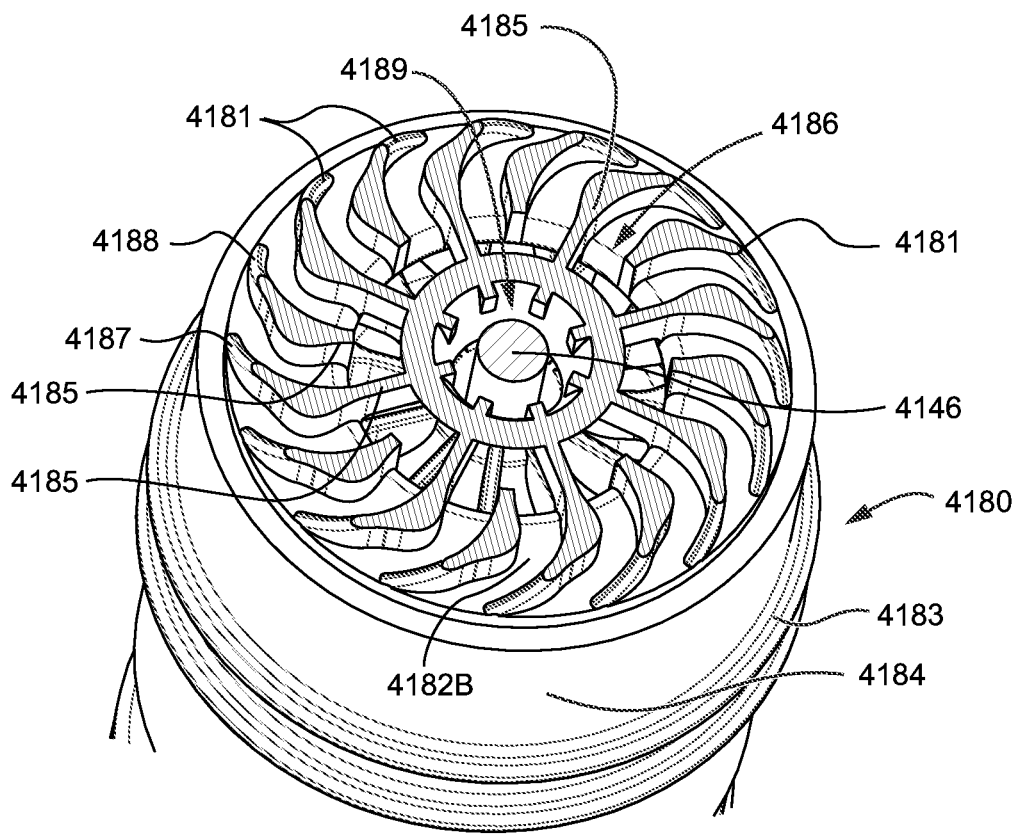

FIG. 10C depicts a cross-sectional view of an end of a partially disassembled blower of an RPT system taken through line 10C-10C of FIG. 10A according to an example of the present technology.

Figure 10D:
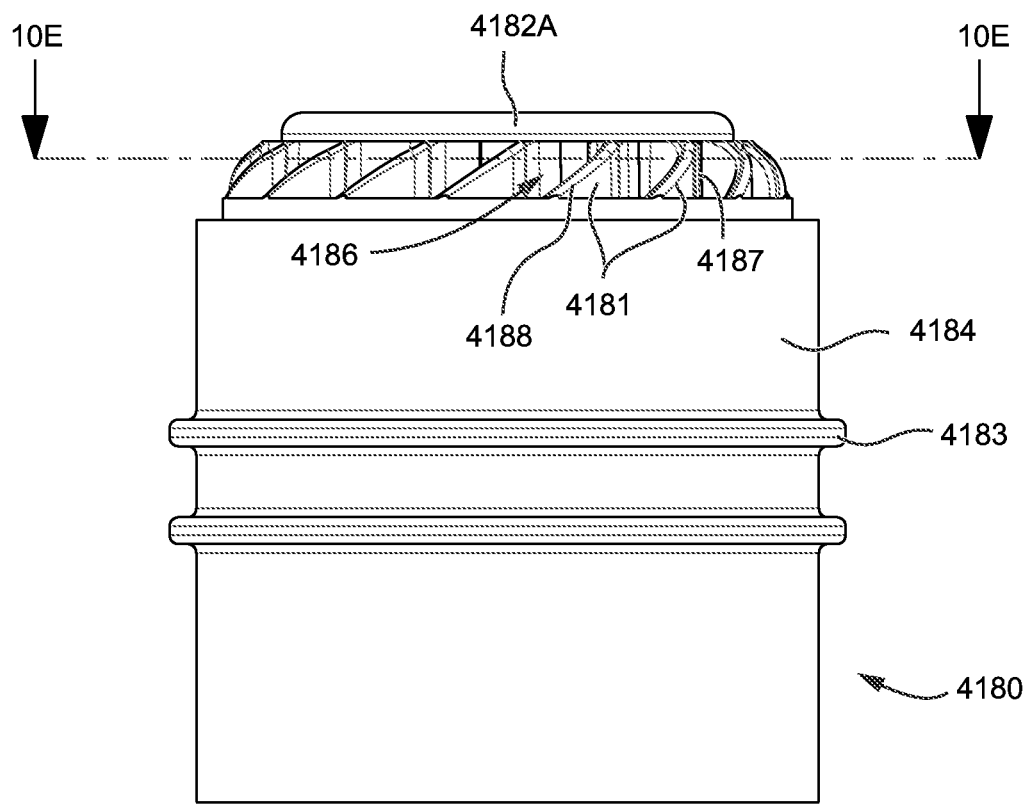

FIG. 10D depicts a side elevation view of a first stator of a blower of an RPT system according to an example of the present technology.

Figure 10E:
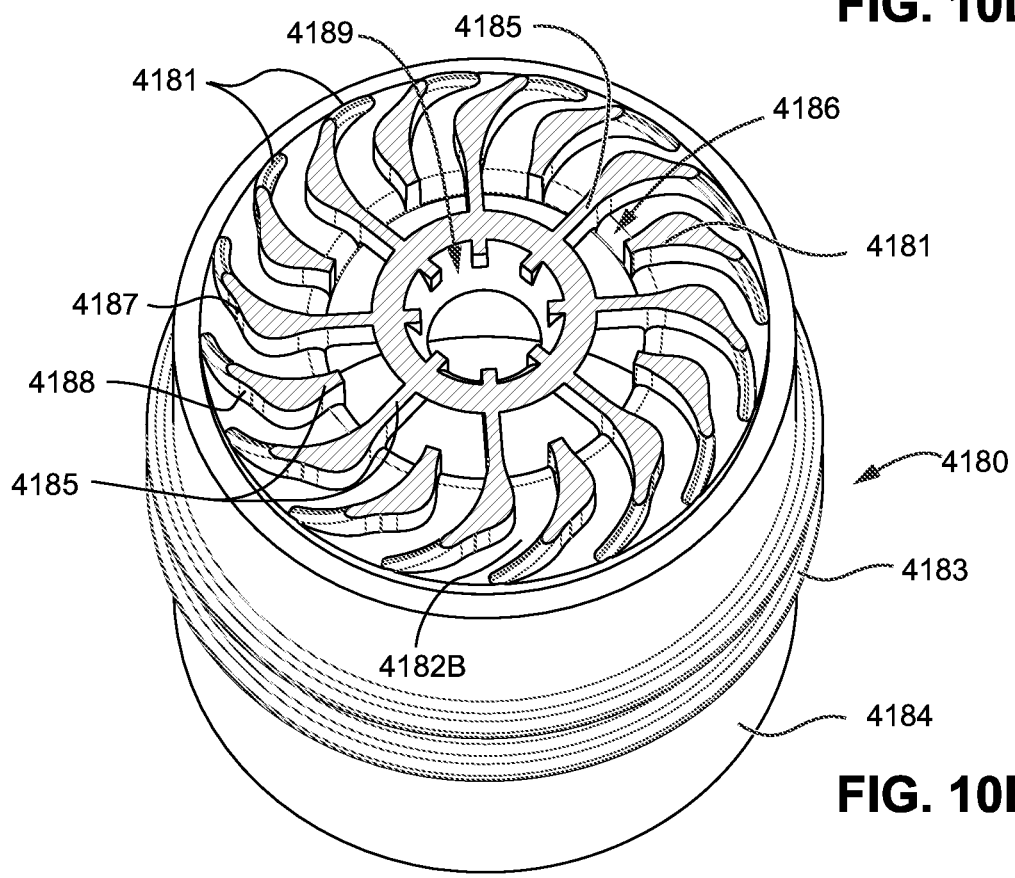

FIG. 10E depicts a cross-sectional view of a first stator of a blower of an RPT system taken through line 10E-10E of FIG. 10D according to an example of the present technology.

Figure 11A:
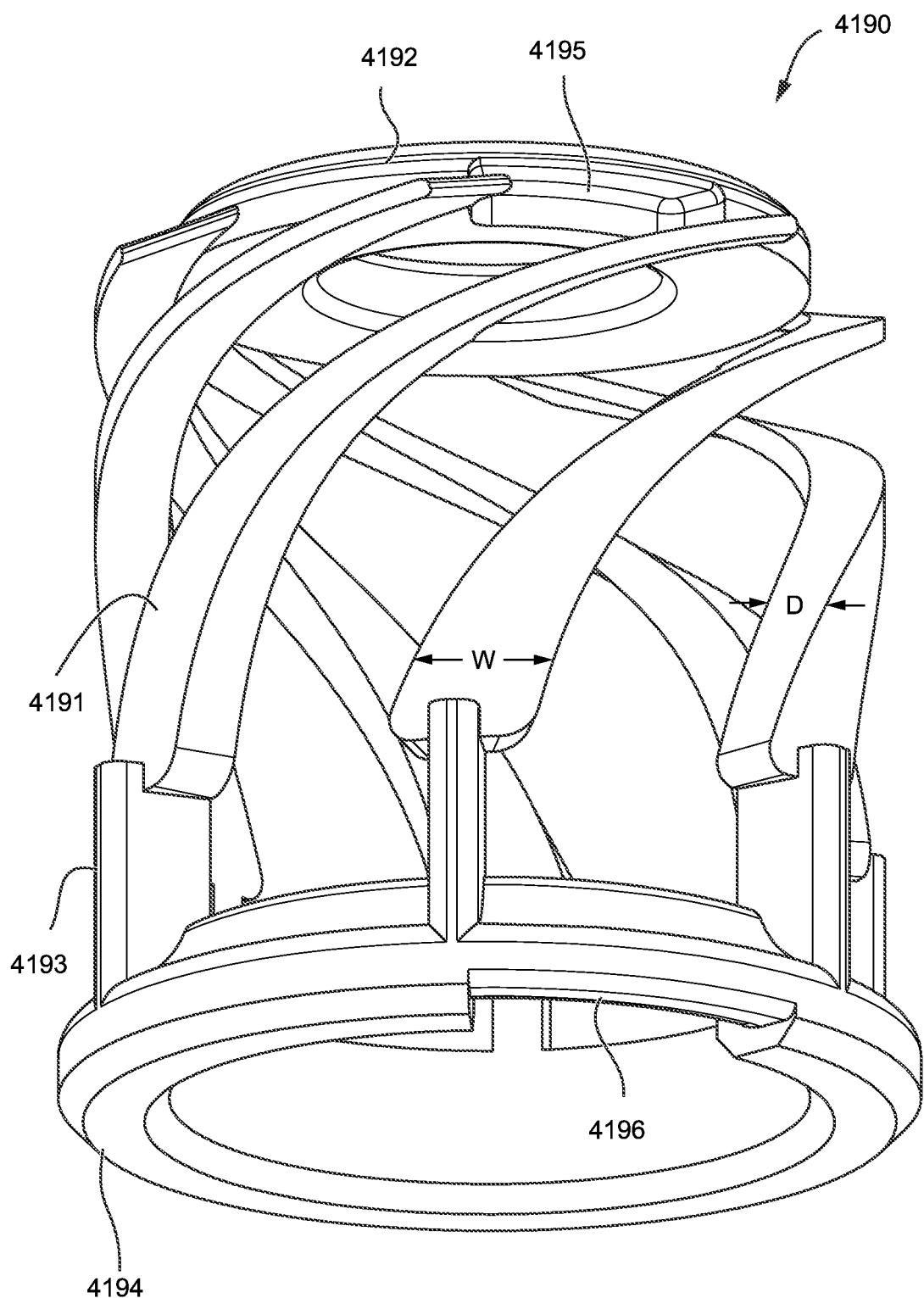

FIG. 11A depicts a perspective view of a second stator of a blower of an RPT system according to an example of the present technology.

Figure 11B:
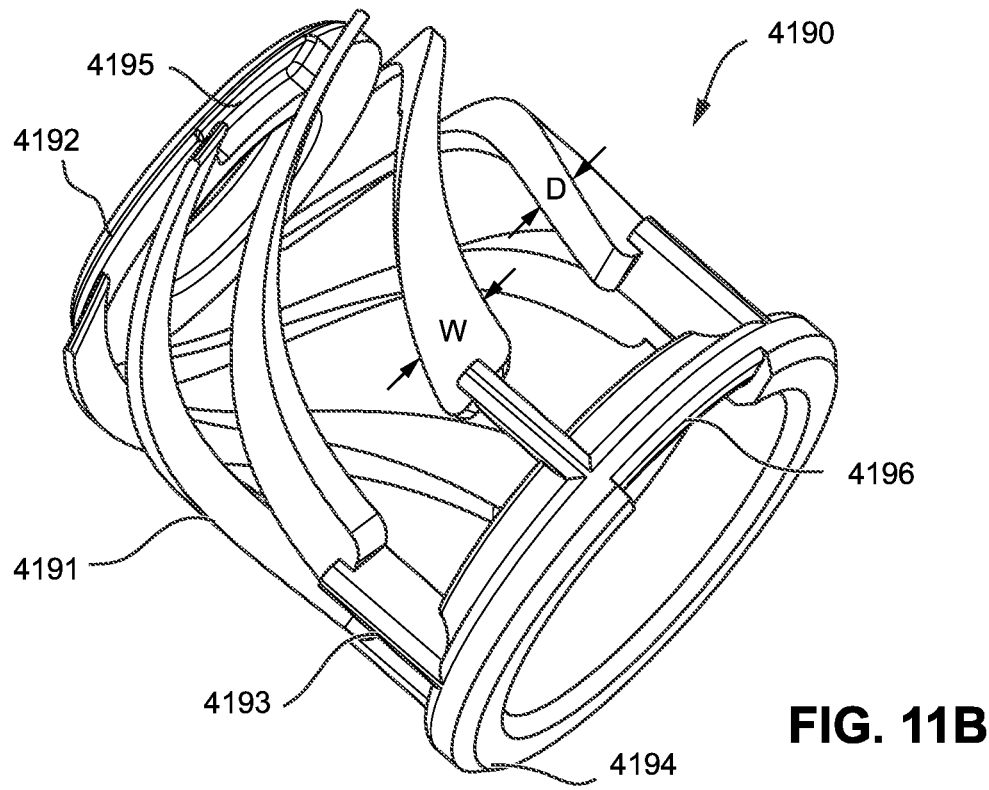

FIG. 11B depicts another perspective view of a second stator of a blower of an RPT system according to an example of the present technology.

Figure 11C:
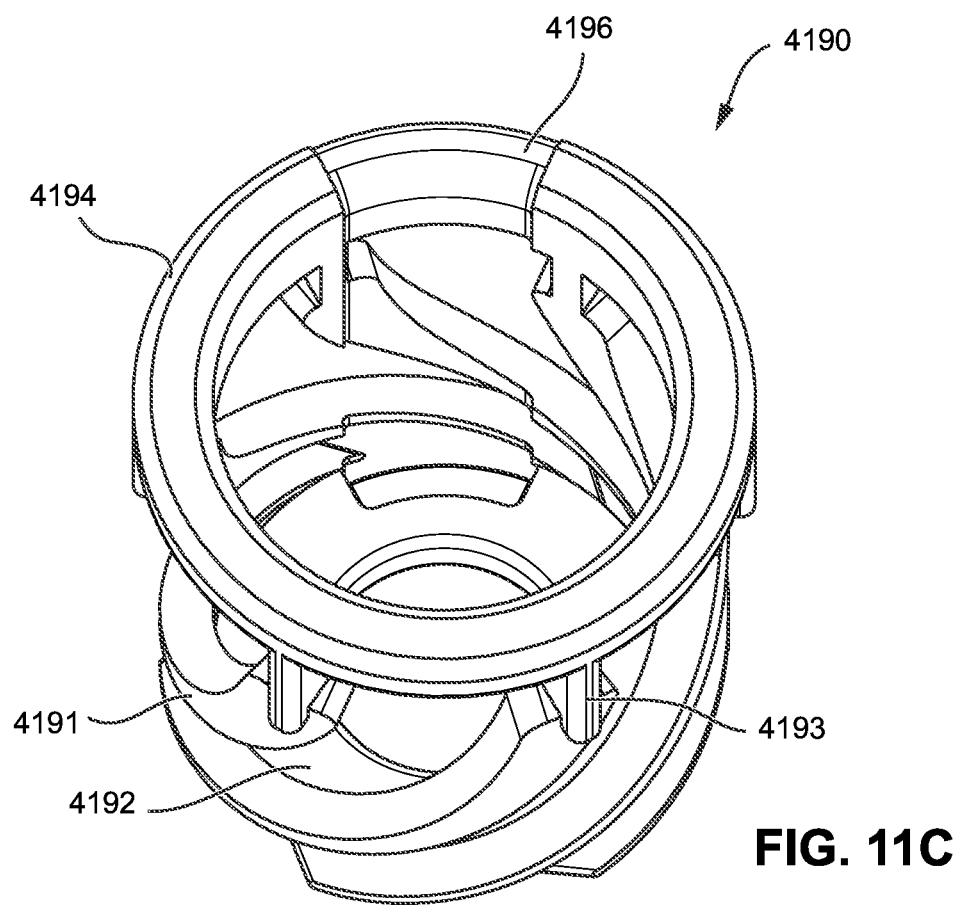

FIG. 11C depicts another perspective view of a second stator of a blower of an RPT system according to an example of the present technology.

Figure 12A:
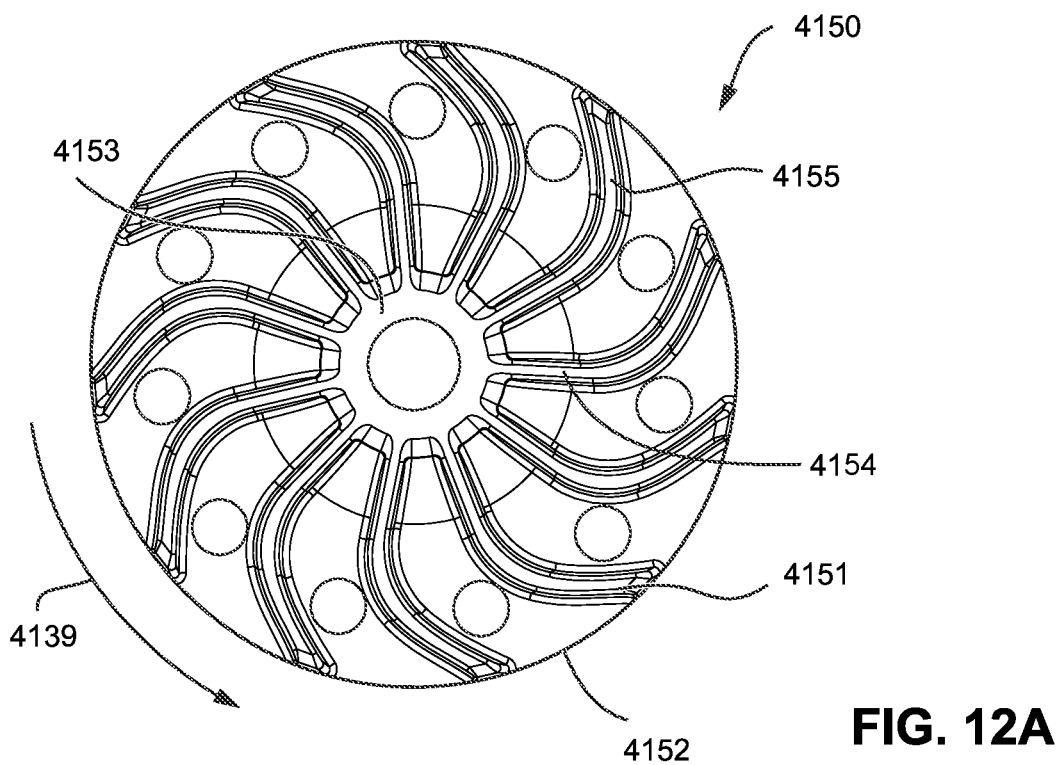

FIG. 12A depicts a plan view of an impeller of a blower of an RPT system according to an example of the present technology.

Figure 12B:
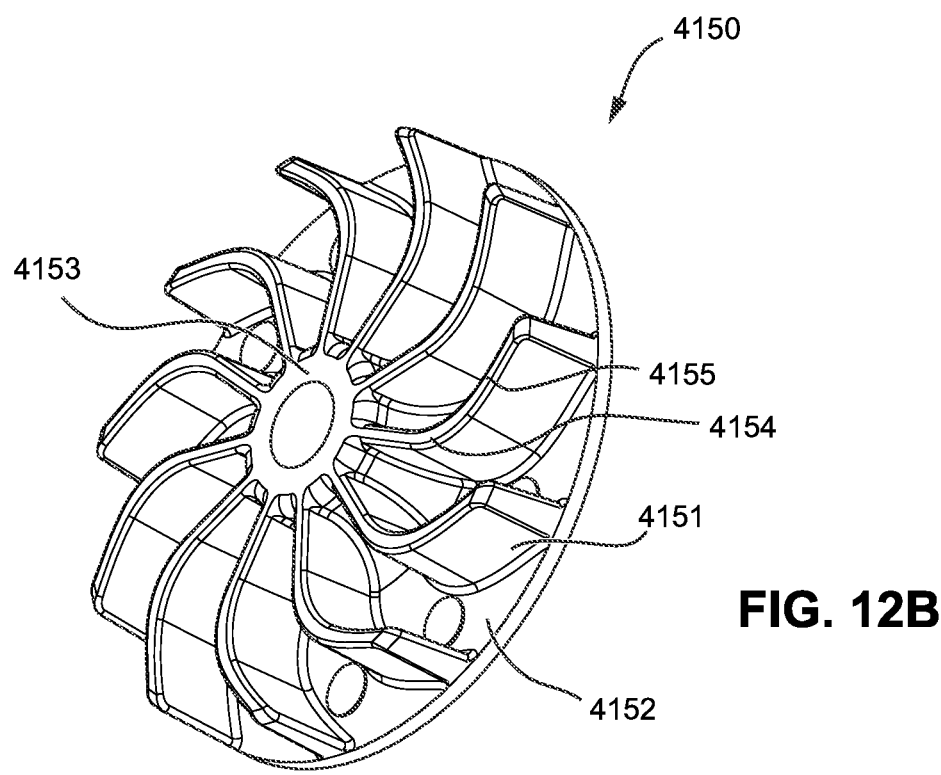

FIG. 12B depicts a perspective view of an impeller of a blower of an RPT system according to an example of the present technology.

Figure 13A:
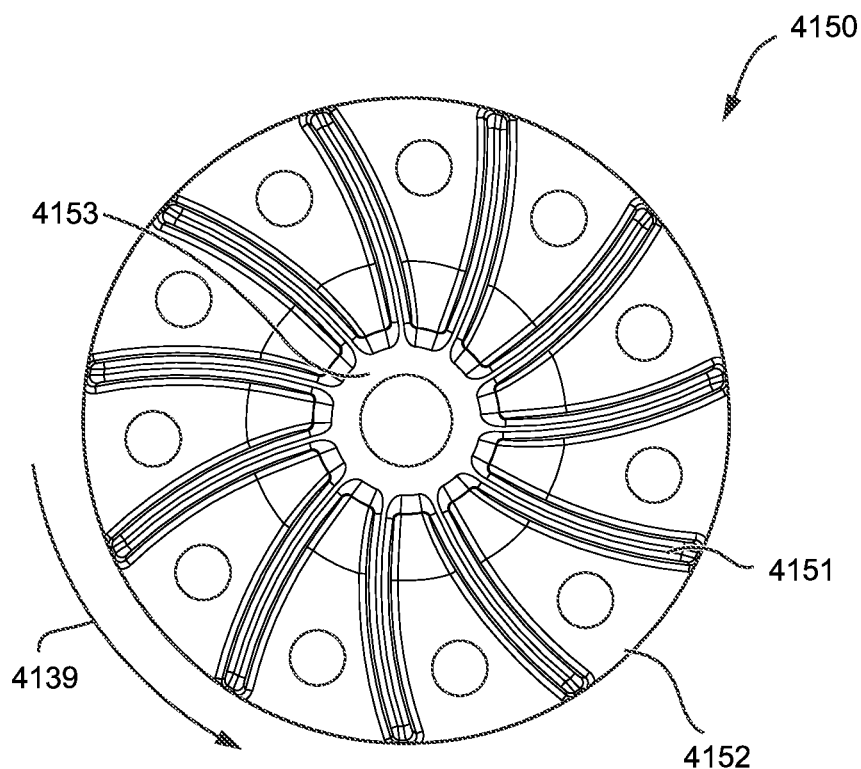

FIG. 13A depicts a plan view of an impeller of a blower of an RPT system according to an example of the present technology.

Figure 13B:
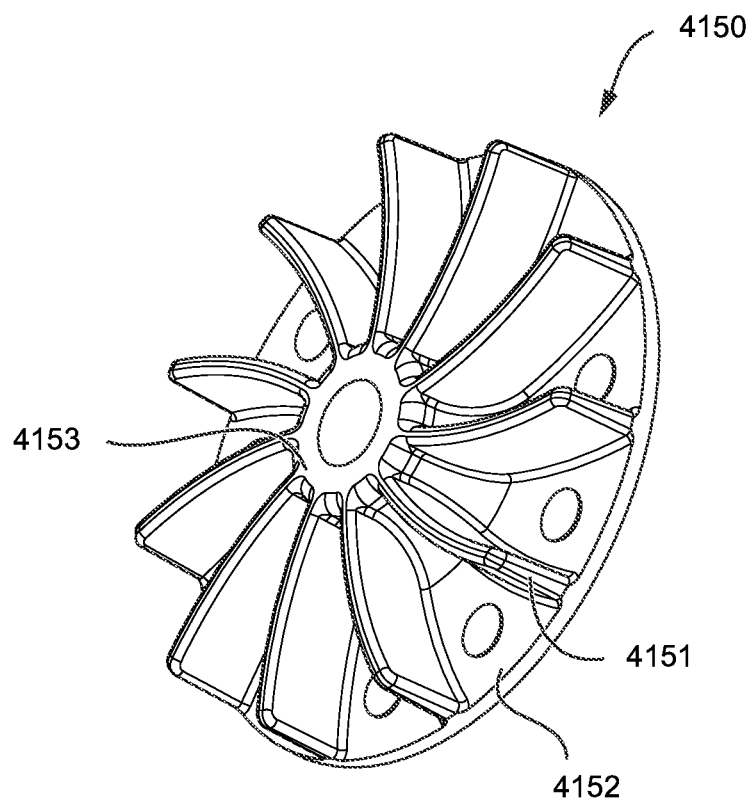

FIG. 13B depicts a perspective view of an impeller of a blower of an RPT system according to an example of the present technology.

Figure 14:
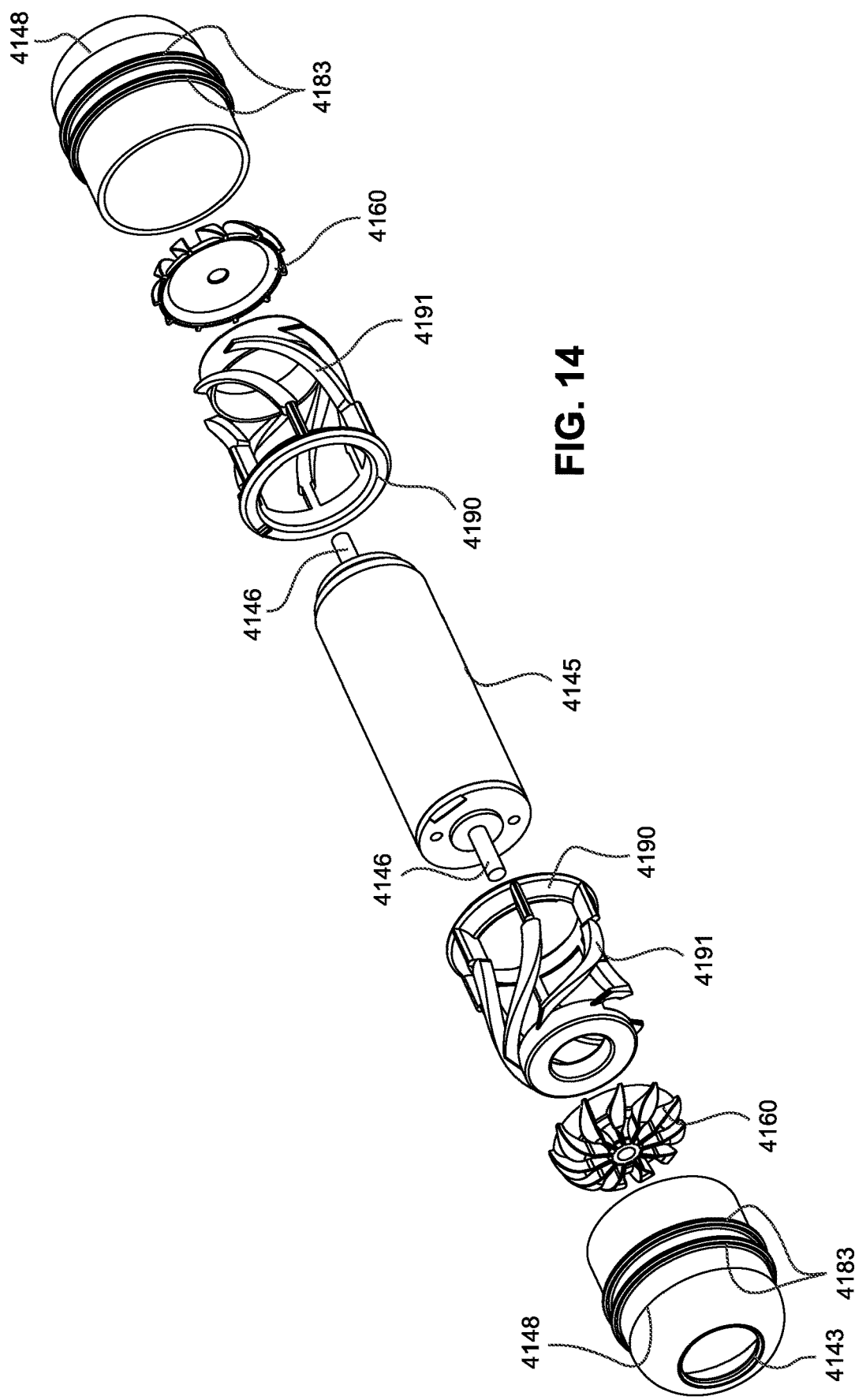

FIG. 14 depicts an exploded view of a blower of an RPT system according to an example of the present technology.

Figure 15A:
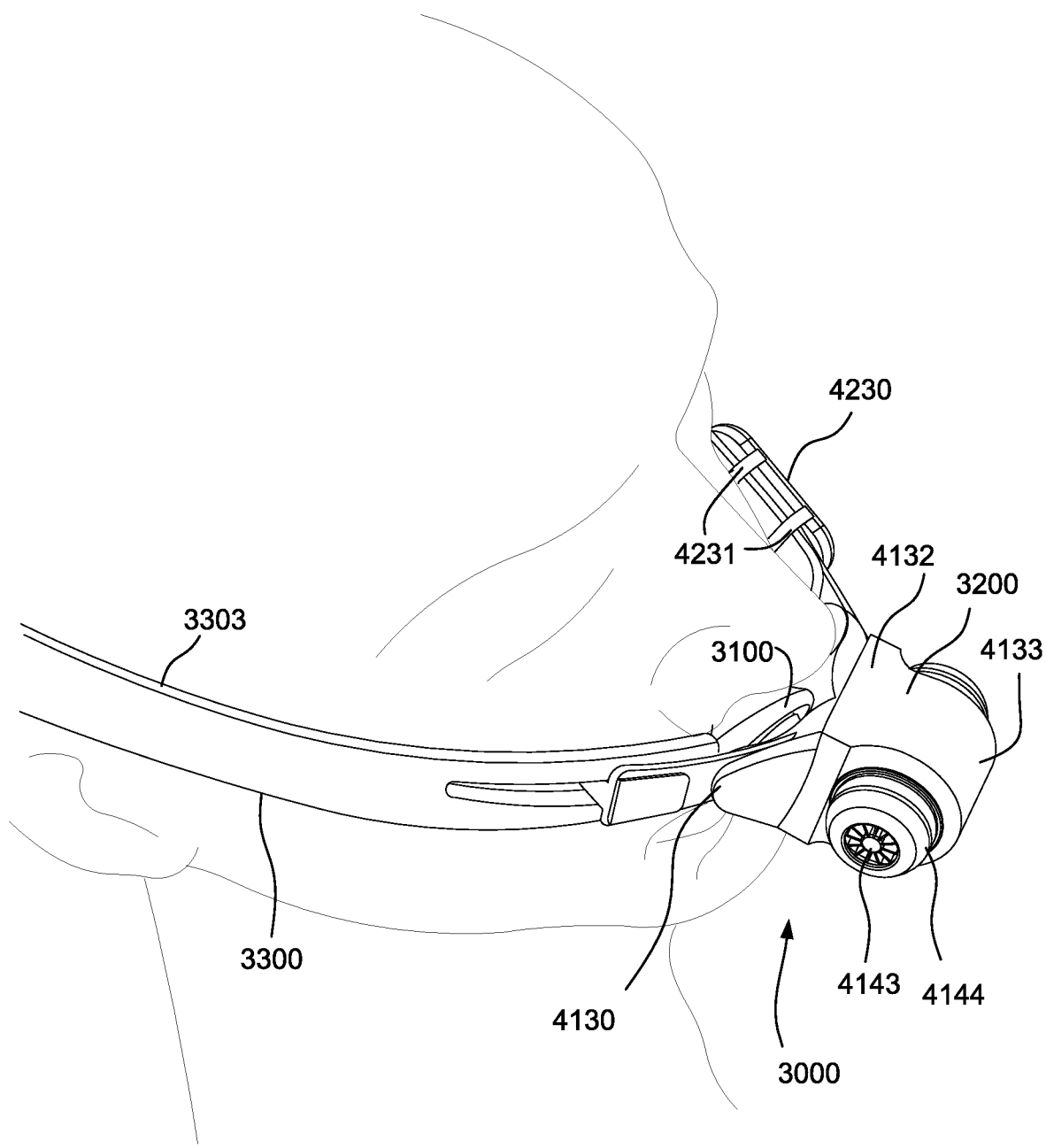

FIG. 15A depicts an anterior perspective view of a patient wearing an RPT system according to an example of the present technology.

Figure 15B:
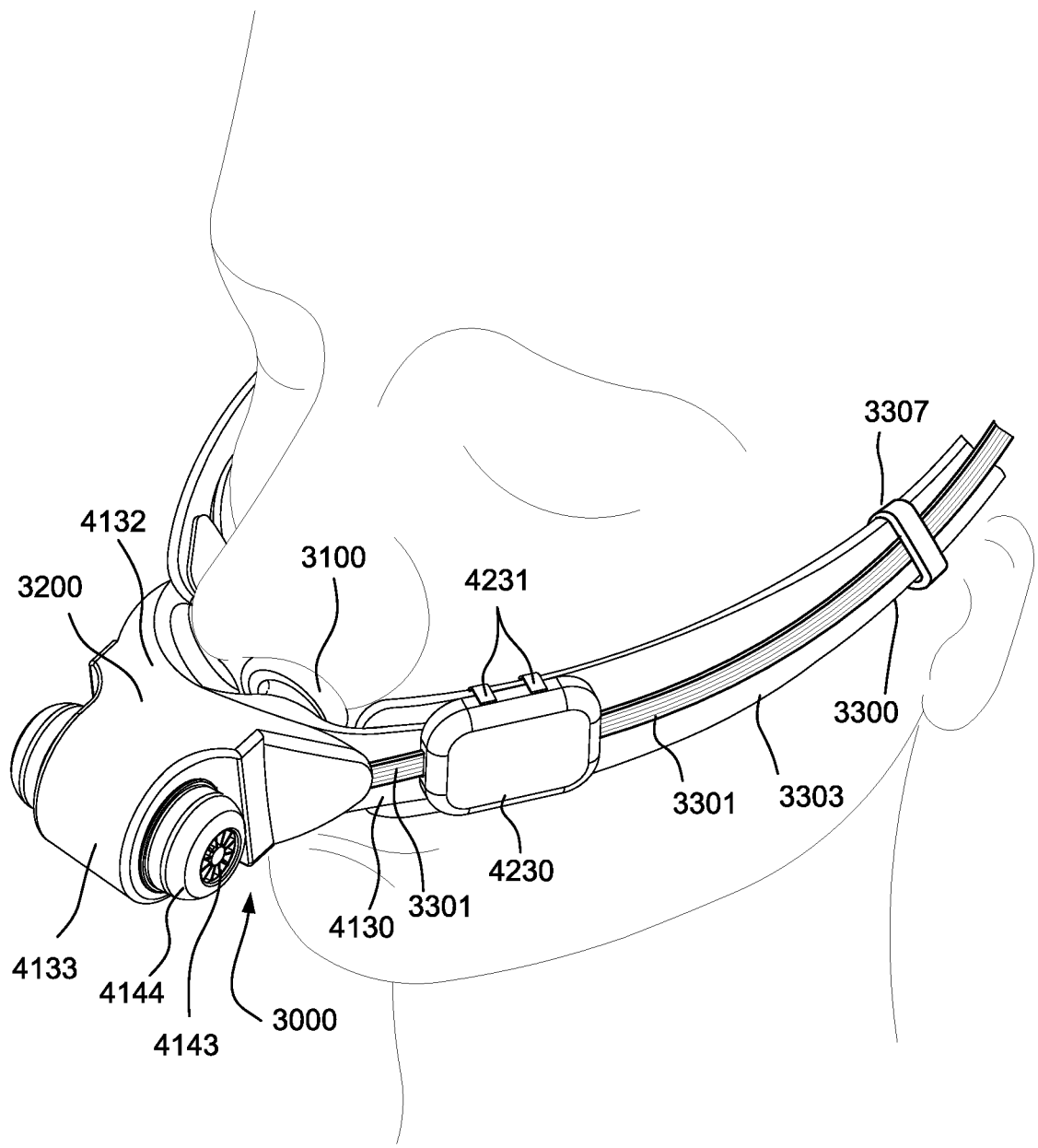

FIG. 15B depicts another anterior perspective view of a patient wearing an RPT system according to an example of the present technology.

Figure 15C:
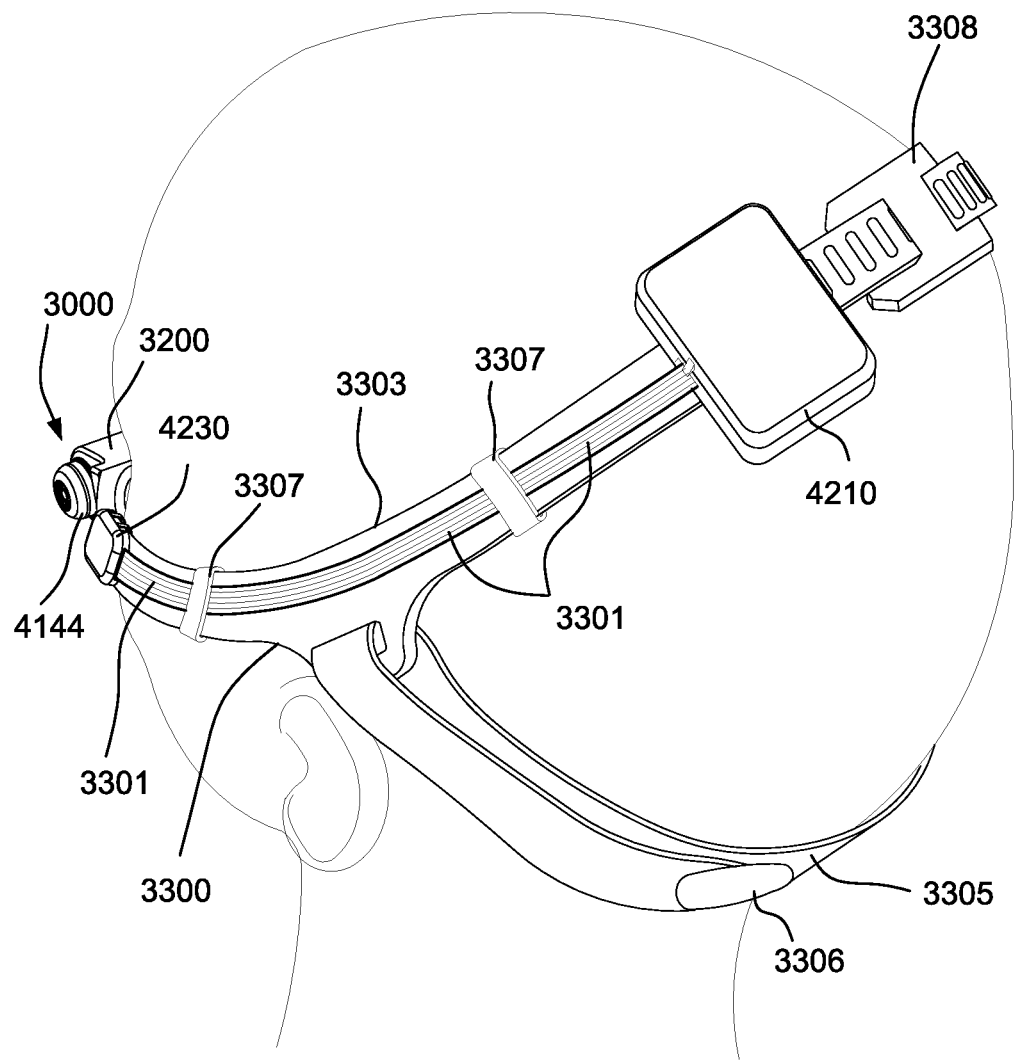

FIG. 15C depicts a posterior perspective view of a patient wearing an RPT system according to an example of the present technology.

Figure 16A:
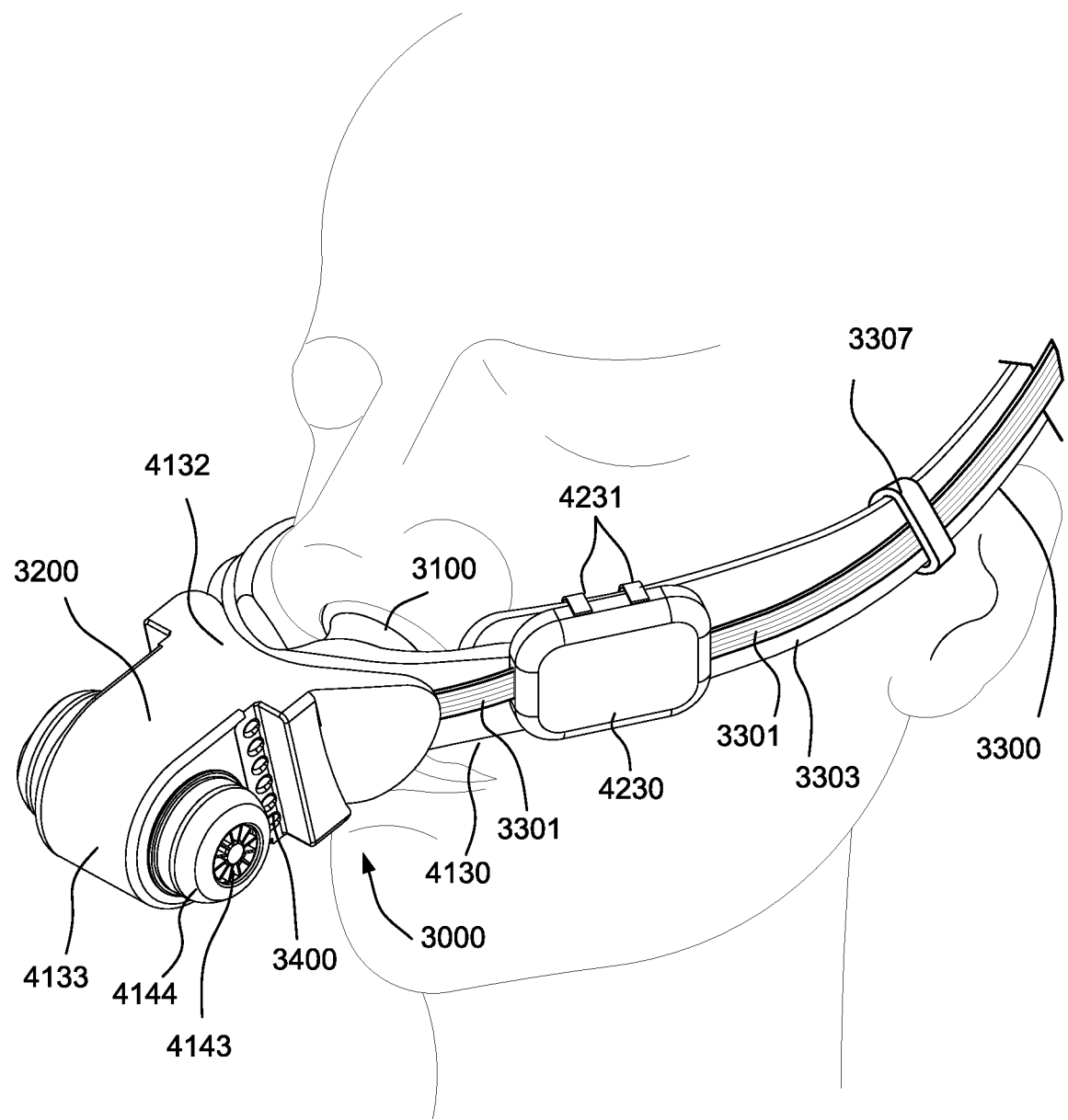

FIG. 16A depicts an anterior perspective view of a patient wearing an RPT system according to an example of the present technology.

Figure 16B:
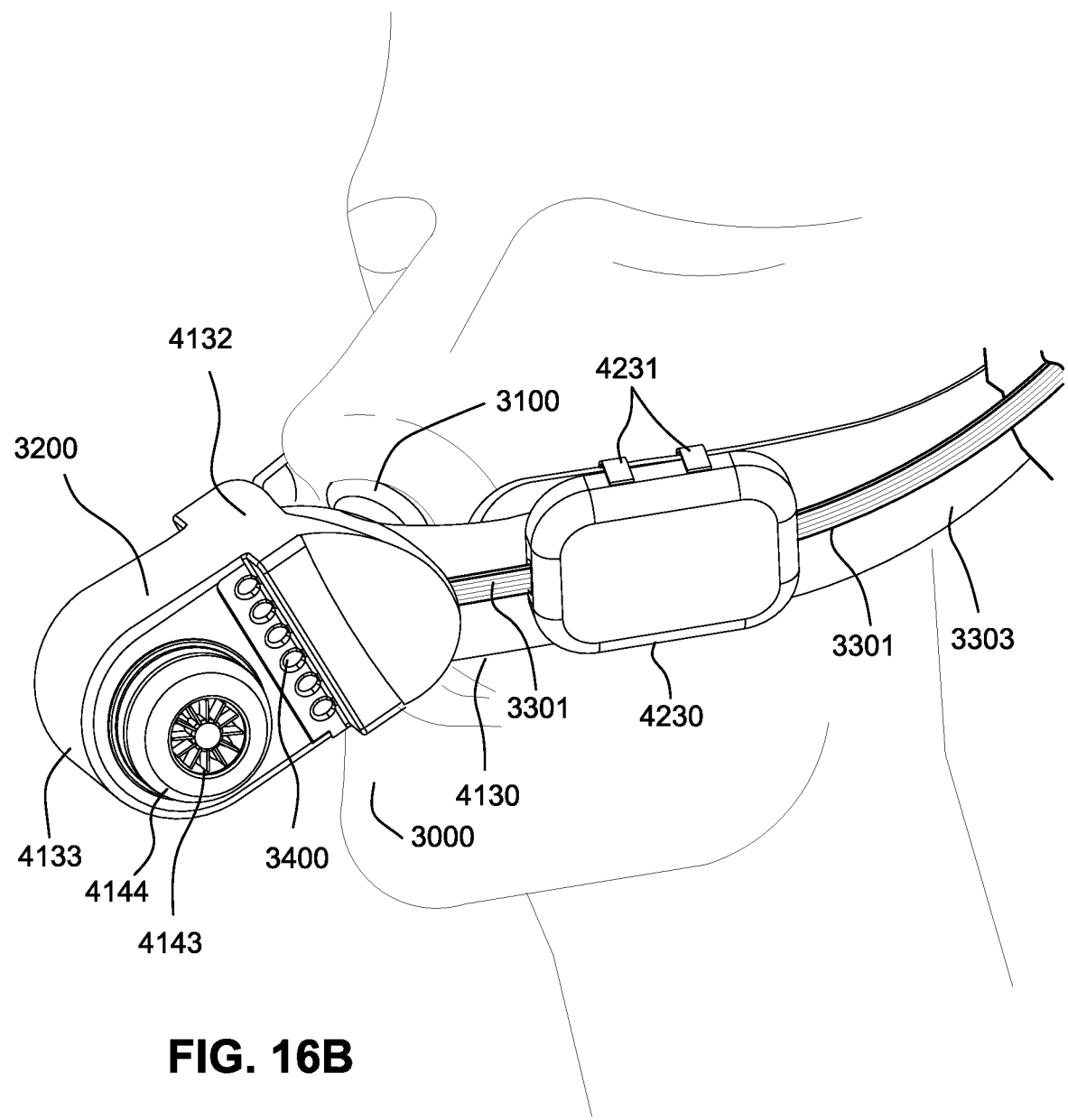

FIG. 16B depicts another perspective view of a patient wearing an RPT system according to an example of the present technology.

Figure 17:
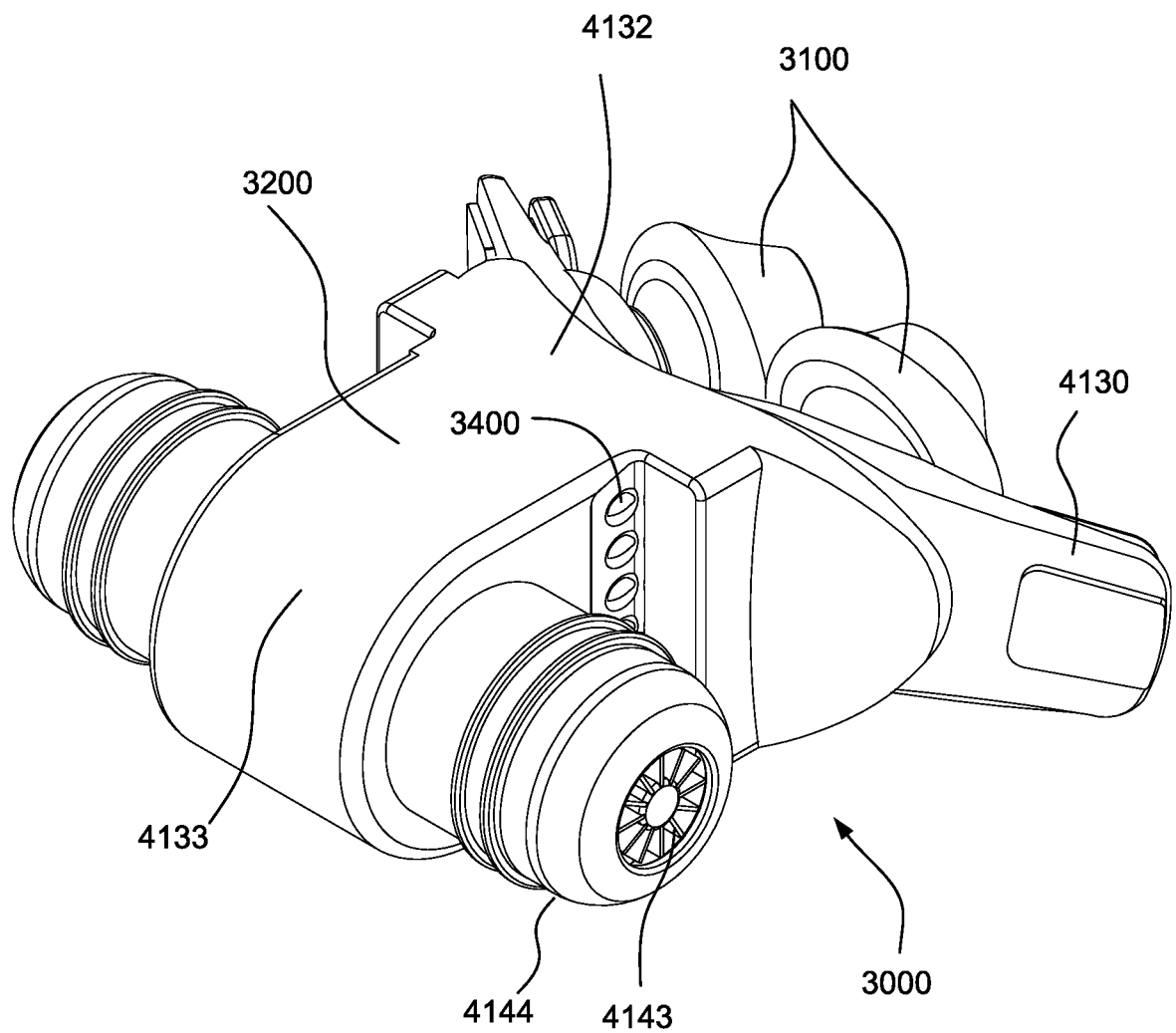

FIG. 17 depicts a perspective view of an RPT system according to an example of the present technology.

Figure 18A:
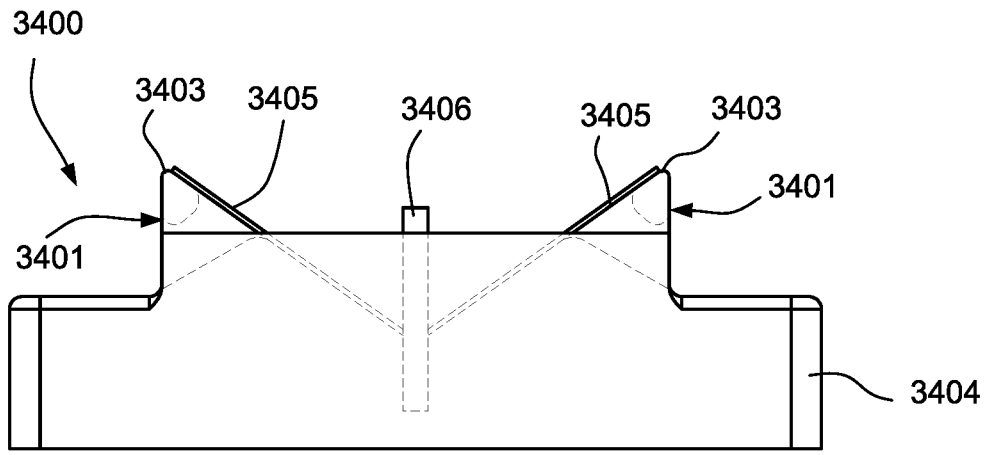

FIG. 18A depicts a side view of a vent assembly according to an example of the present technology.

Figure 18B:
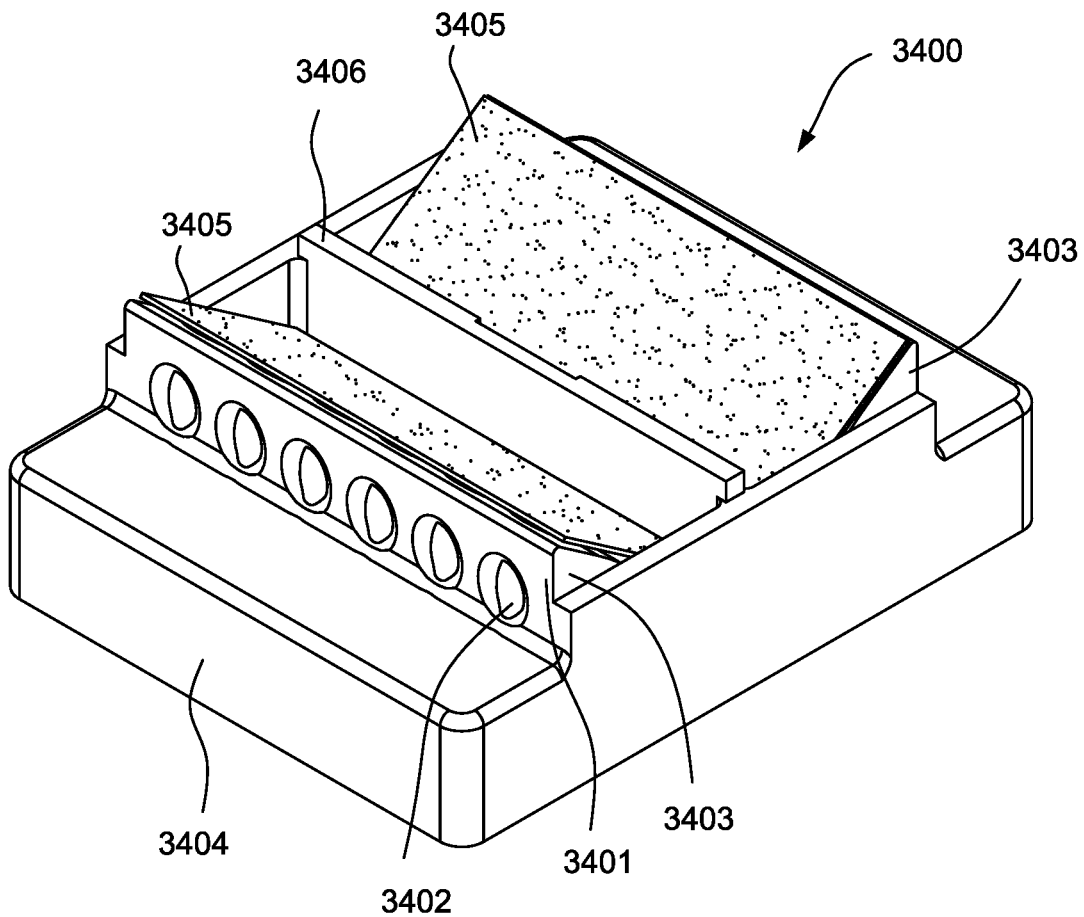

FIG. 18B depicts a top perspective view of a vent assembly according to an example of the present technology.

Figure 18C:
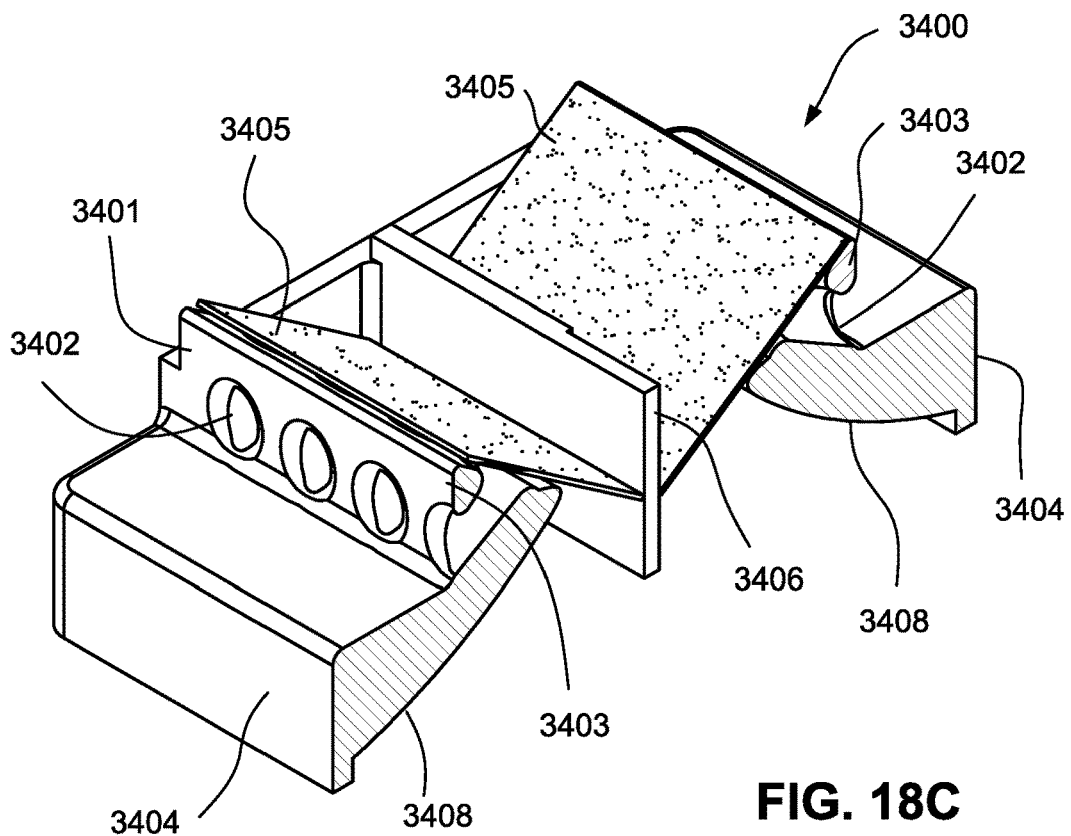

FIG. 18C depicts a cross-sectional perspective view of a vent assembly according to an example of the present technology.

Figure 18D:
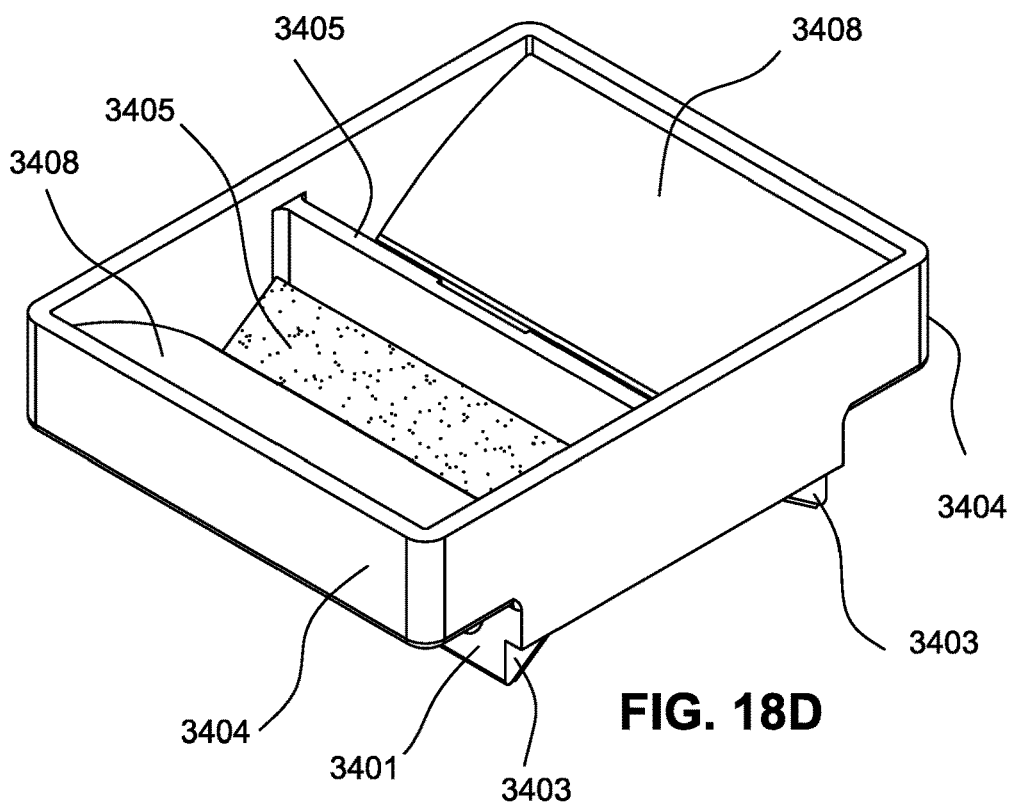

FIG. 18D depicts a bottom perspective view of a vent assembly according to an example of the present technology.

Figure 18E:
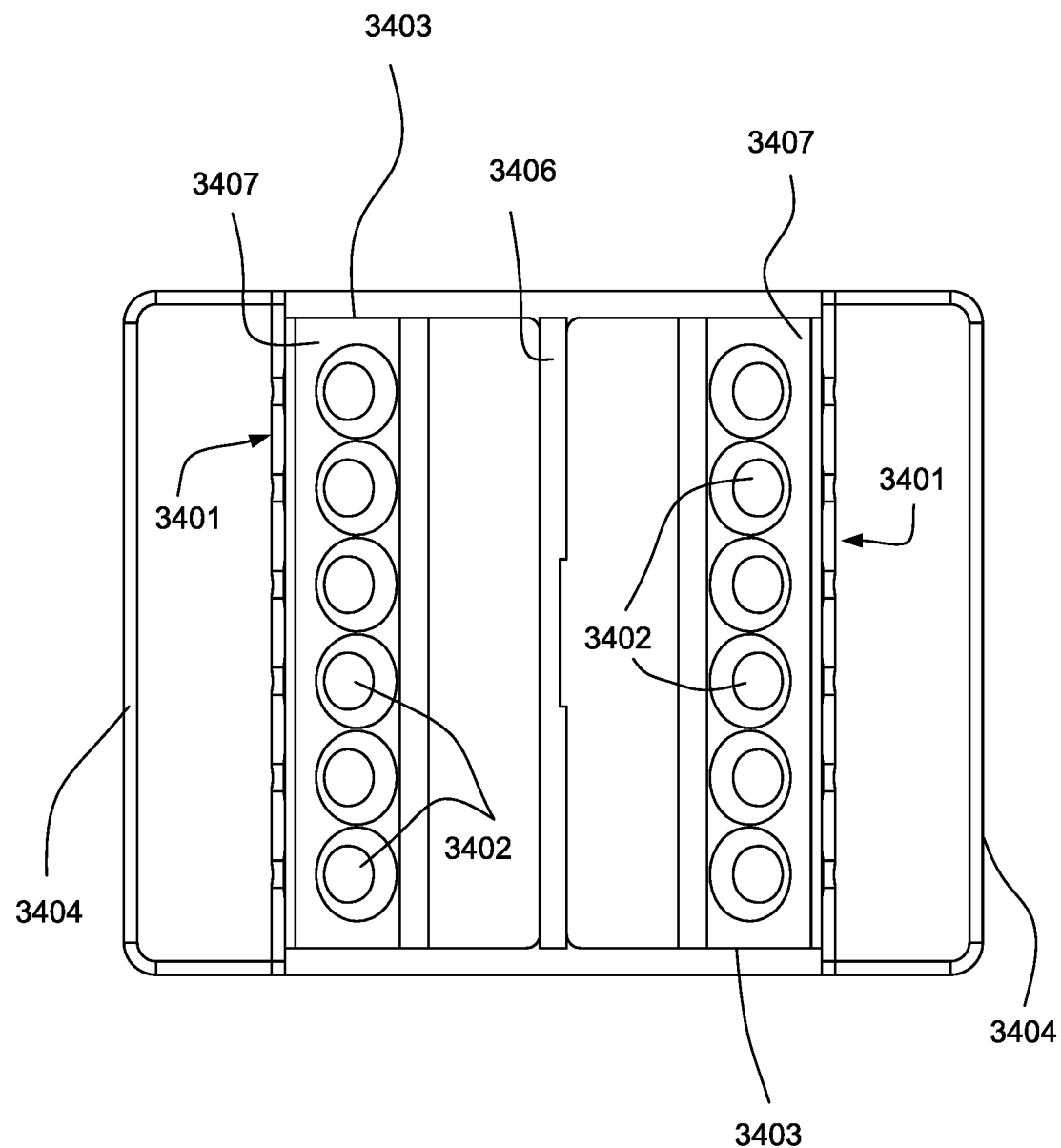

FIG. 18E depicts a top view of a vent assembly according to an example of the present technology.

Figure 18F:
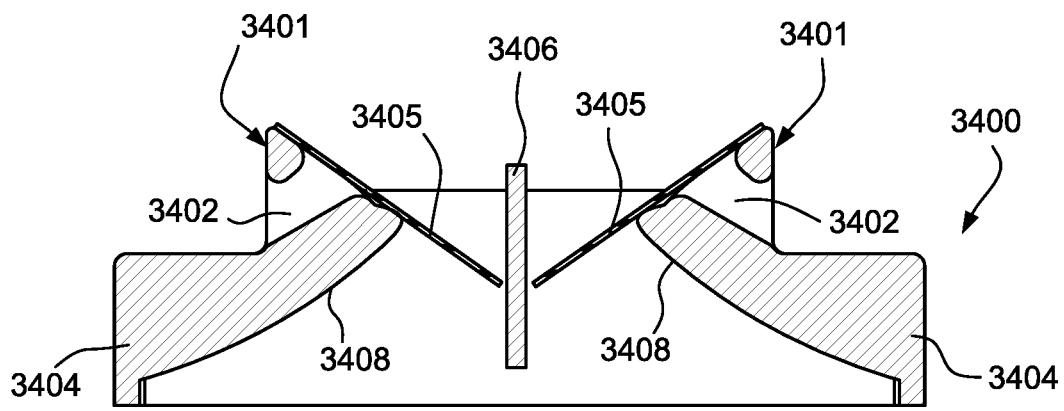

FIG. 18F depicts a side cross-sectional view of a vent assembly in an neutral state according to an example of the present technology.

Figure 18G:
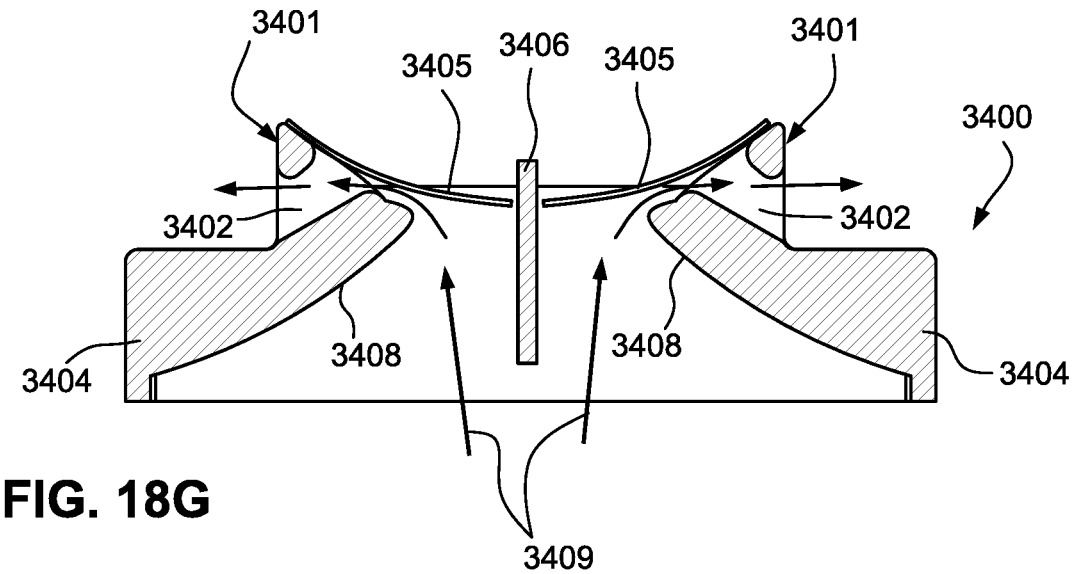

FIG. 18G depicts a side cross-sectional view of a vent assembly during venting according to an example of the present technology.

Figure 18H:
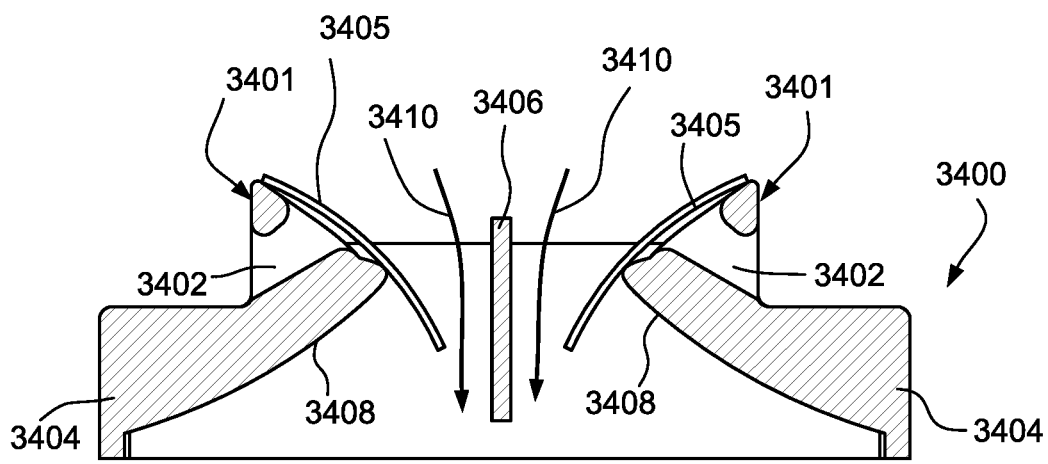

FIG. 18H depicts a side cross-sectional view of a vent assembly while a flow of pressurized gas is passing through the vent assembly to a patient according to an example of the present technology.

Figure 19A:
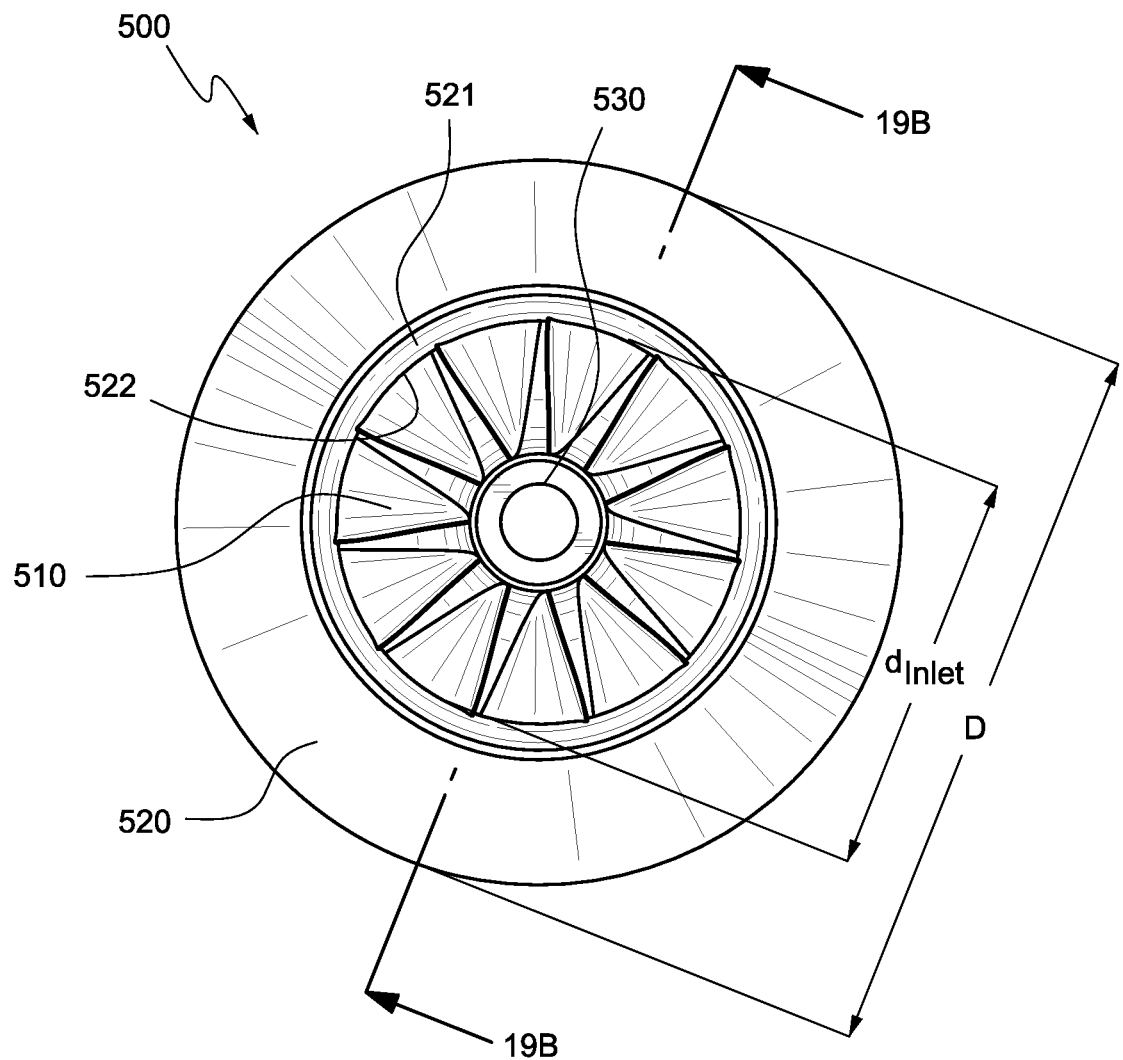

FIG. 19A shows an impeller in accordance with one form of the present technology.

Figure 19B:
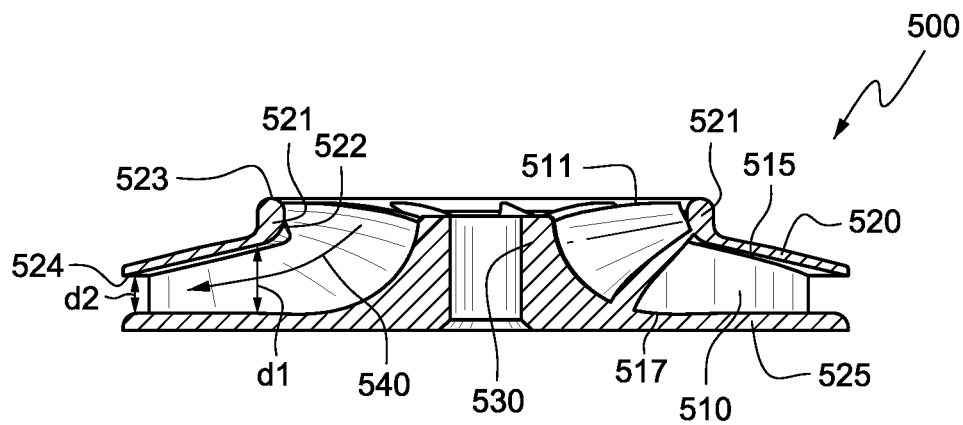

FIG. 19B shows a cross-section of the impeller shown in FIG. 19A.

Figure 19C:
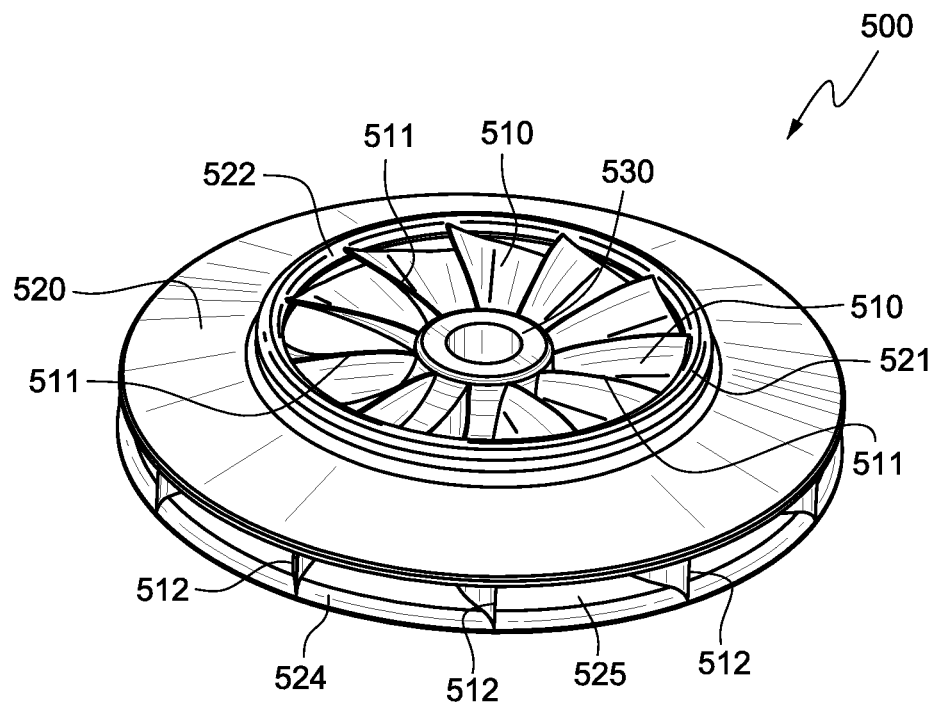

FIG. 19C shows an isometric view of the impeller shown in FIG. 19A.

Figure 19D:
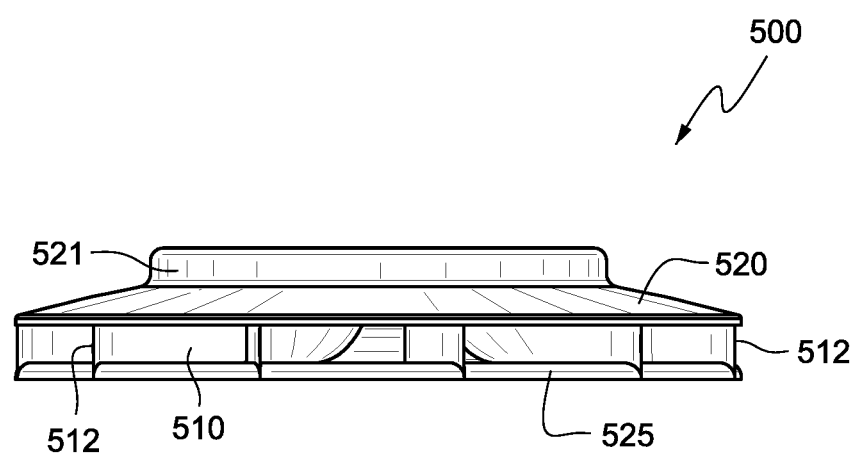

FIG. 19D shows an elevation view of the impeller shown in FIG. 19A.

Figure 19E:
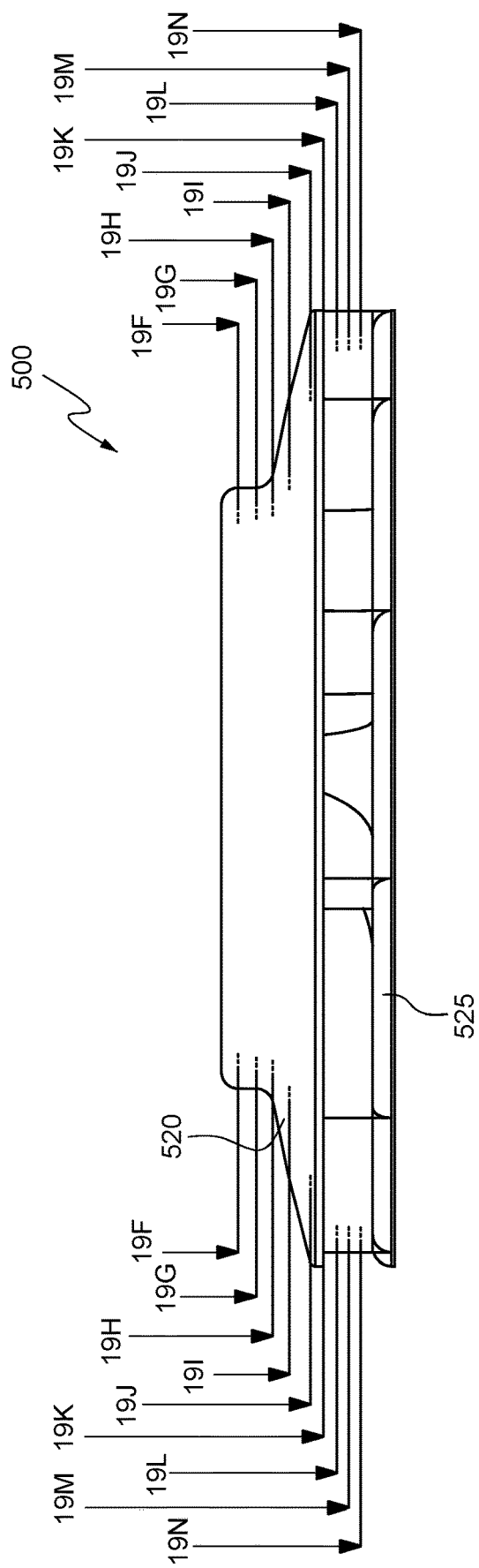

FIG. 19E shows an elevation view of the impeller shown in FIG. 19A, indicating cross sections taken for FIGS. 19F-19N.

FIGS. 19F-19N show plan views of an impeller in accordance with one form of the present technology at various cross sections as indicated on FIG. 19E.

Figure 19F:
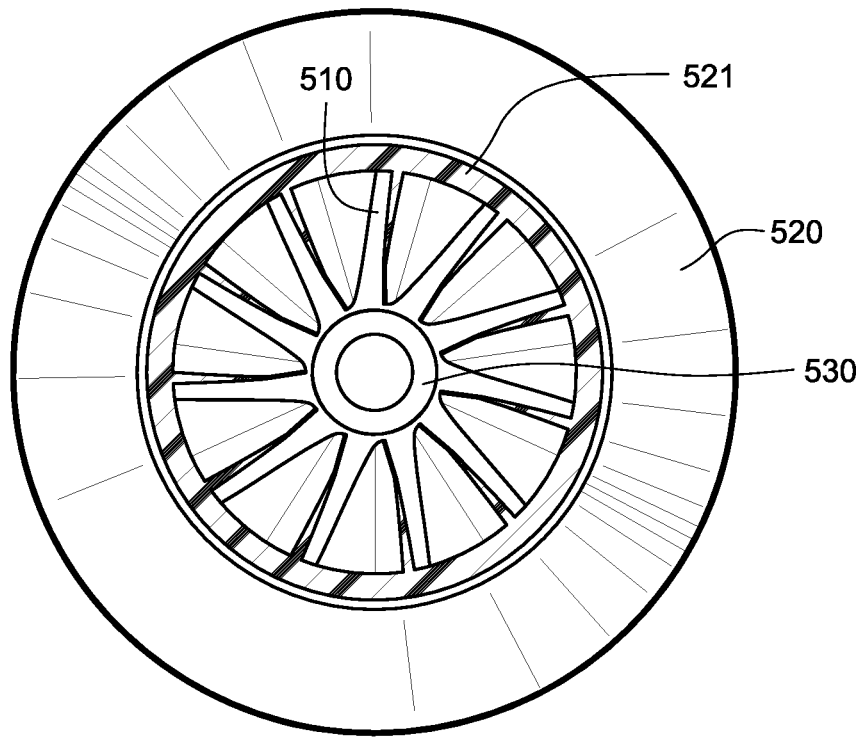
Figure 19G:
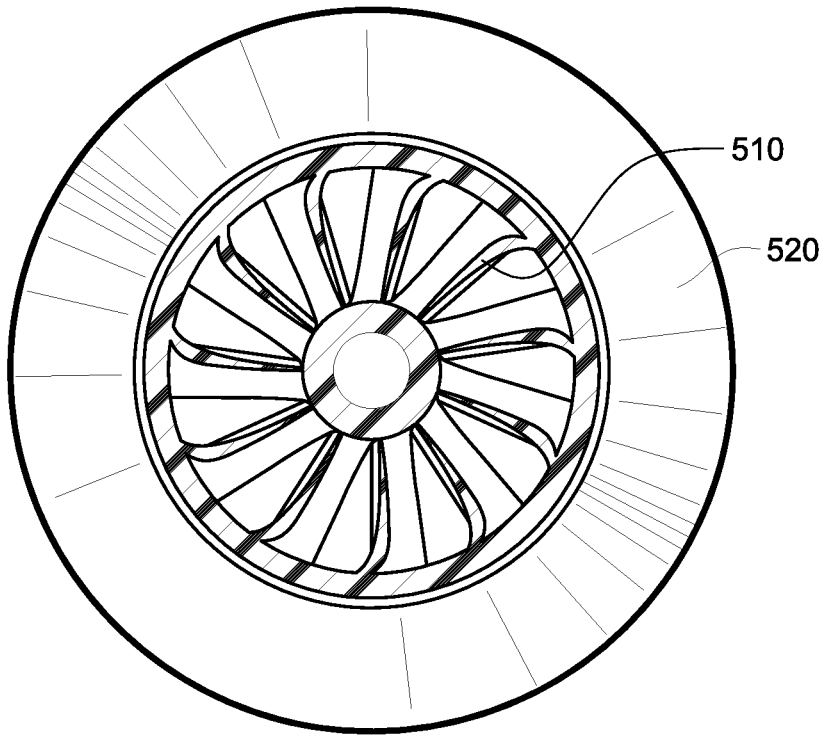
Figure 19H:
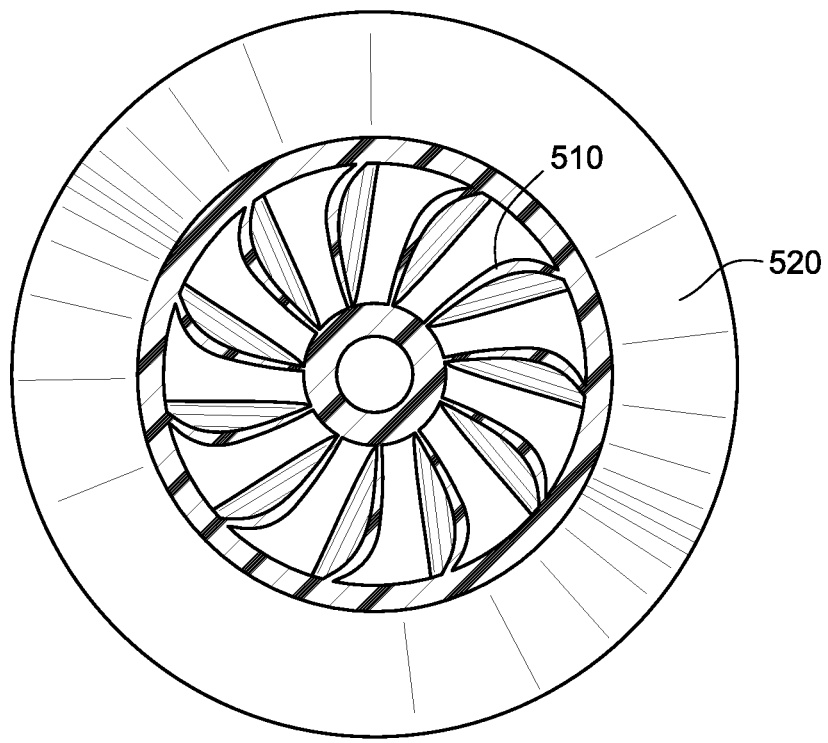
Figure 19I:
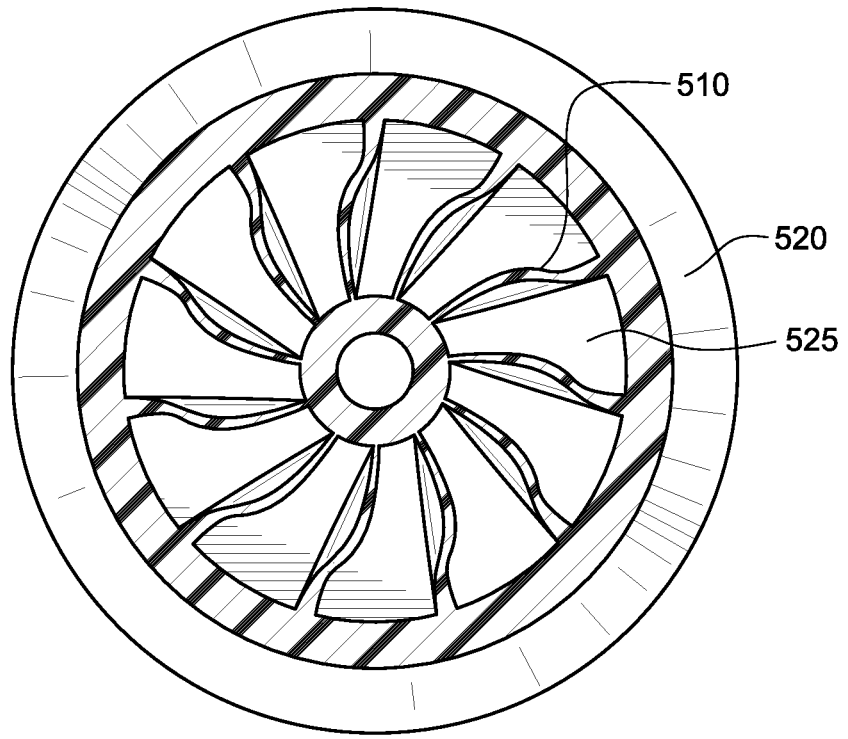
Figure 19J:
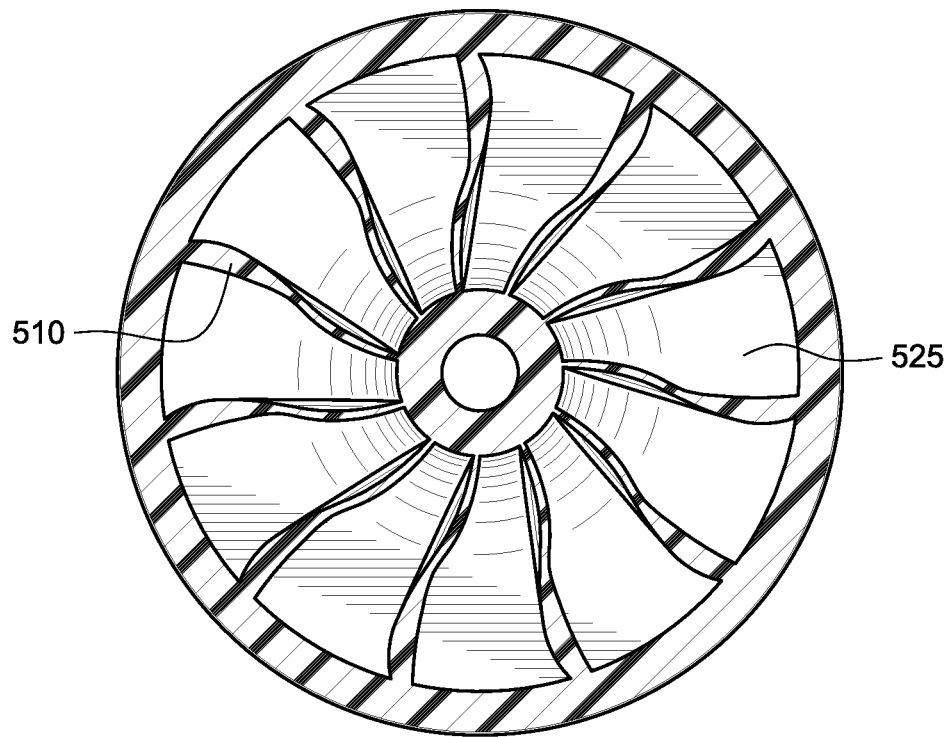
Figure 19K:
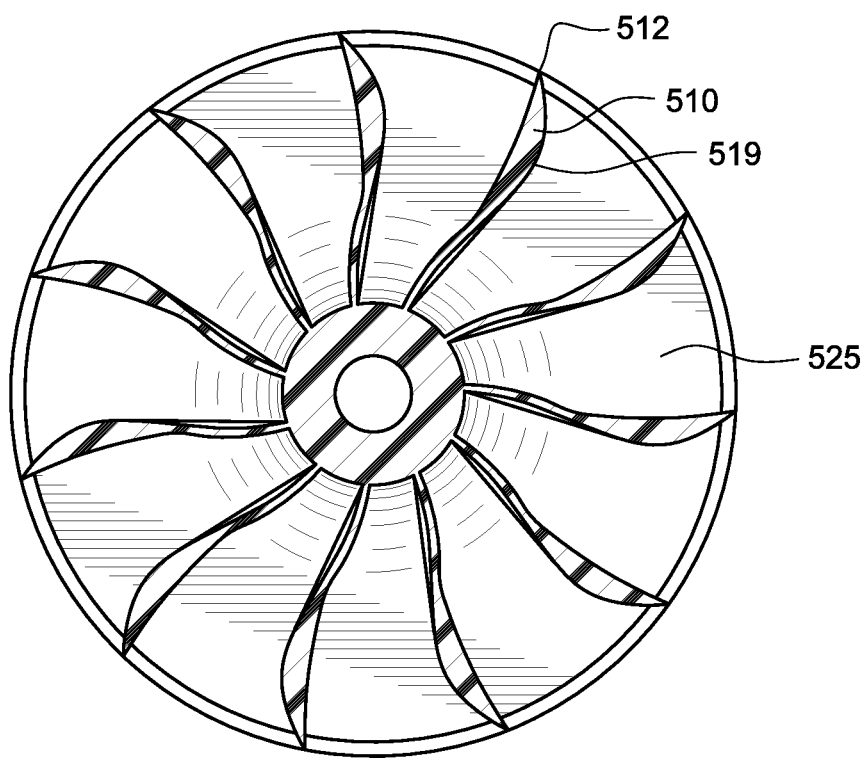
Figure 19L:
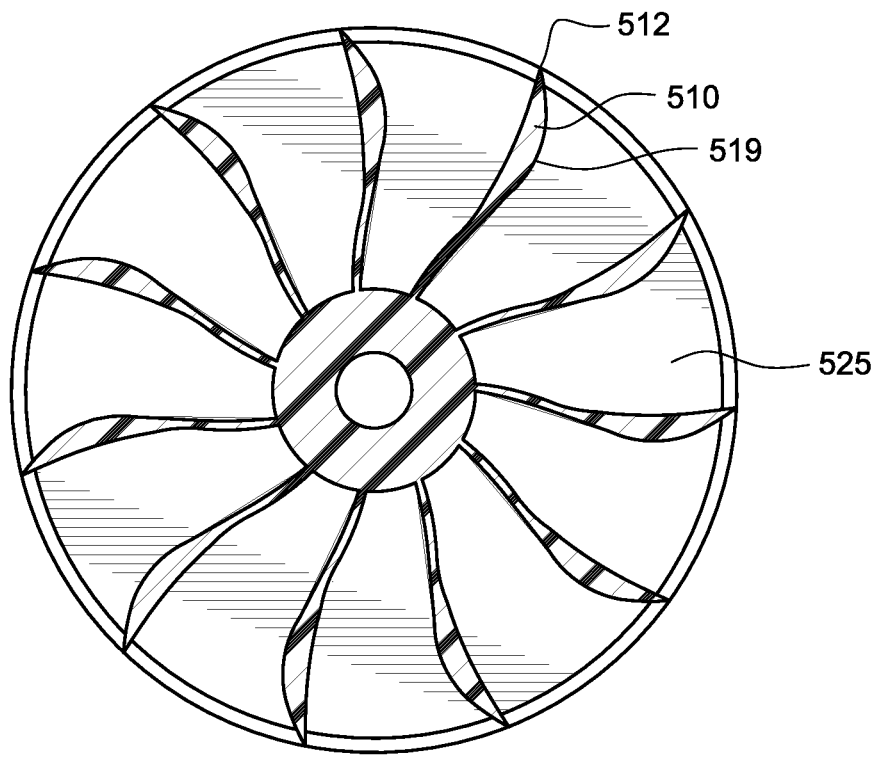
Figure 19M:
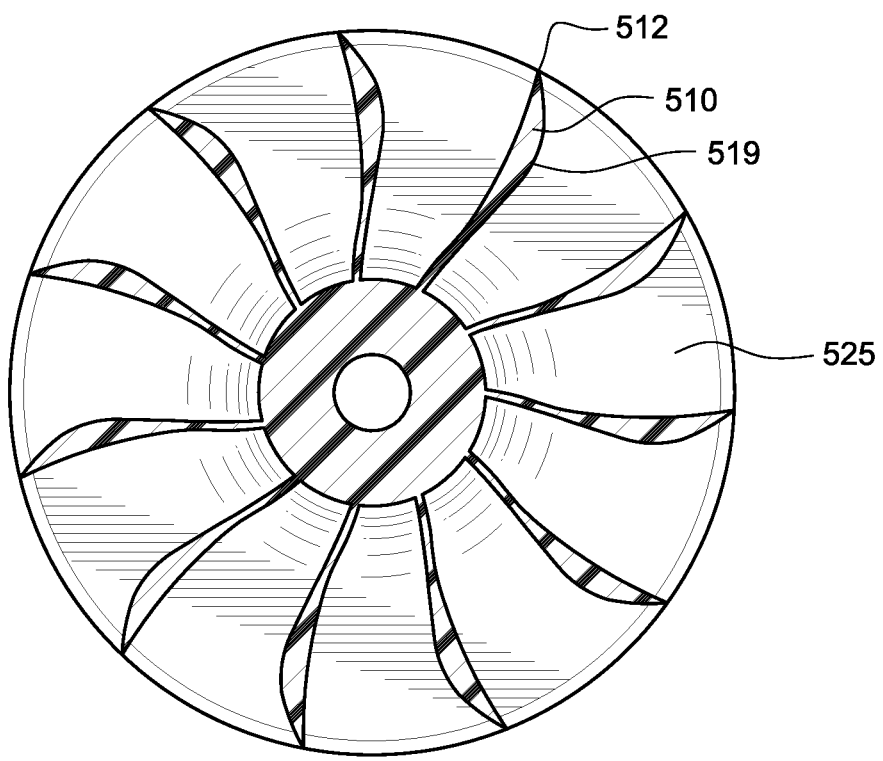
Figure 19N:
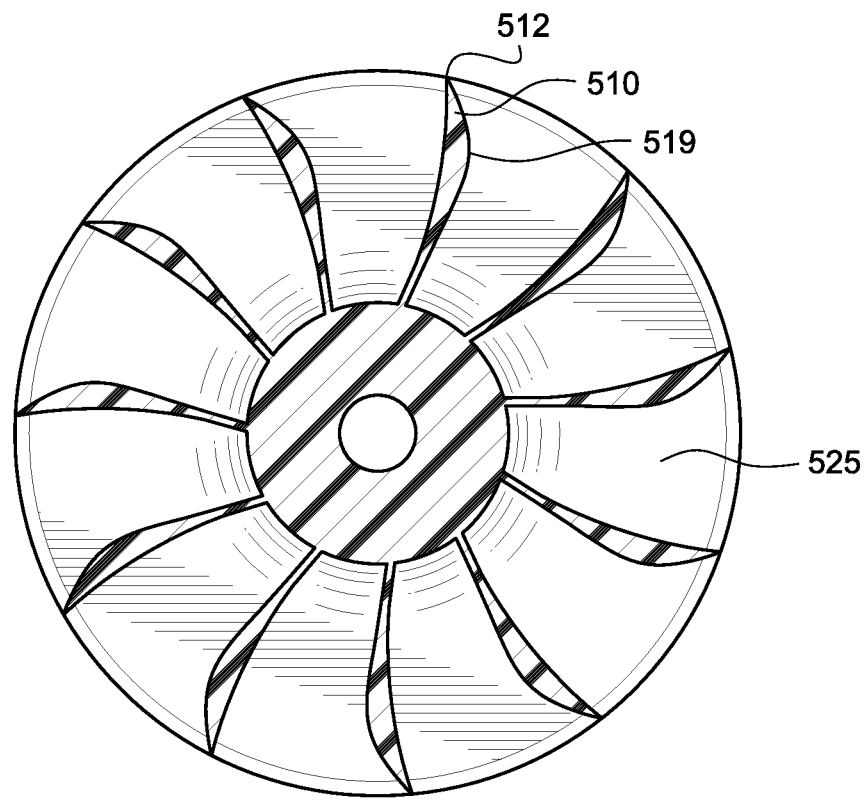
Figure 19O:
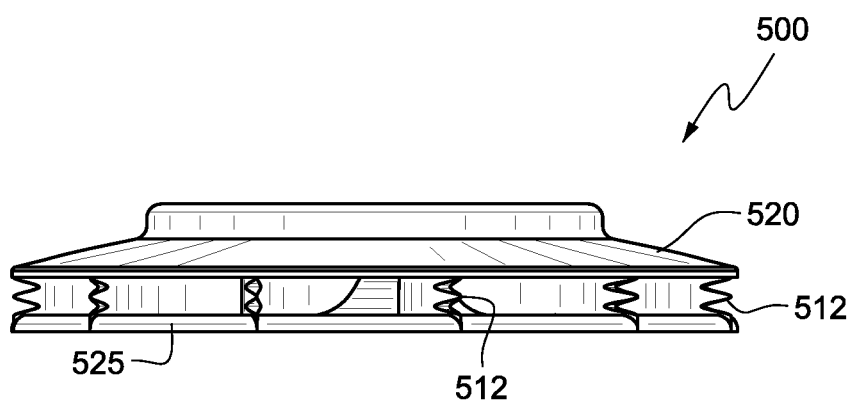

FIG. 19O shows an elevation view of an impeller in accordance with one form of the present technology.

Figure 19P:
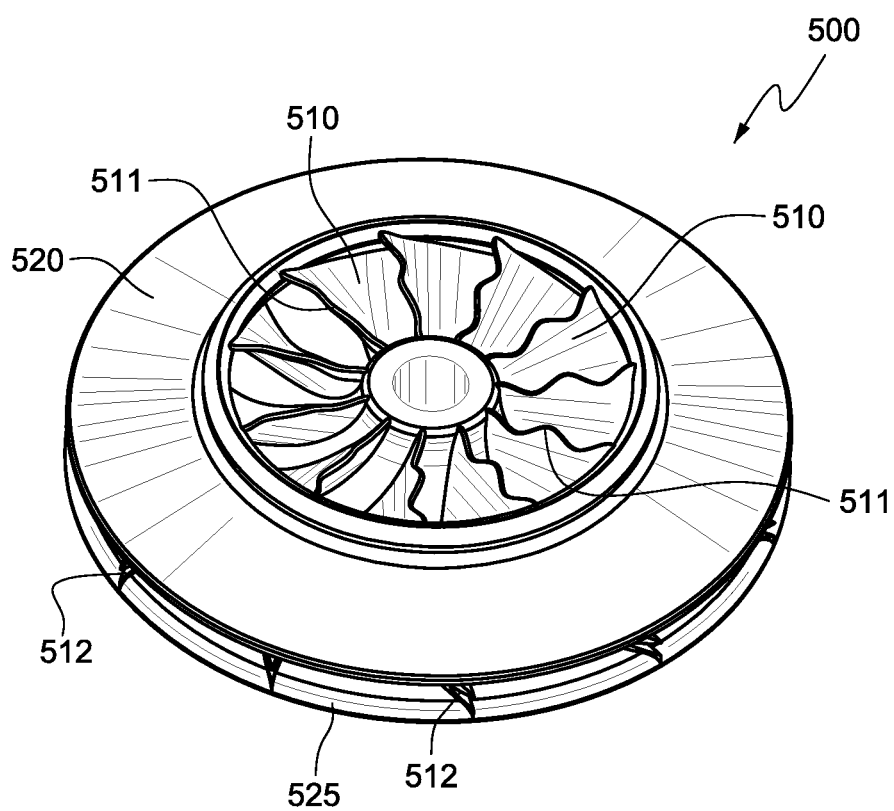

FIG. 19P shows an isometric view of the impeller shown in FIG. 19O.

Figure 19Q:
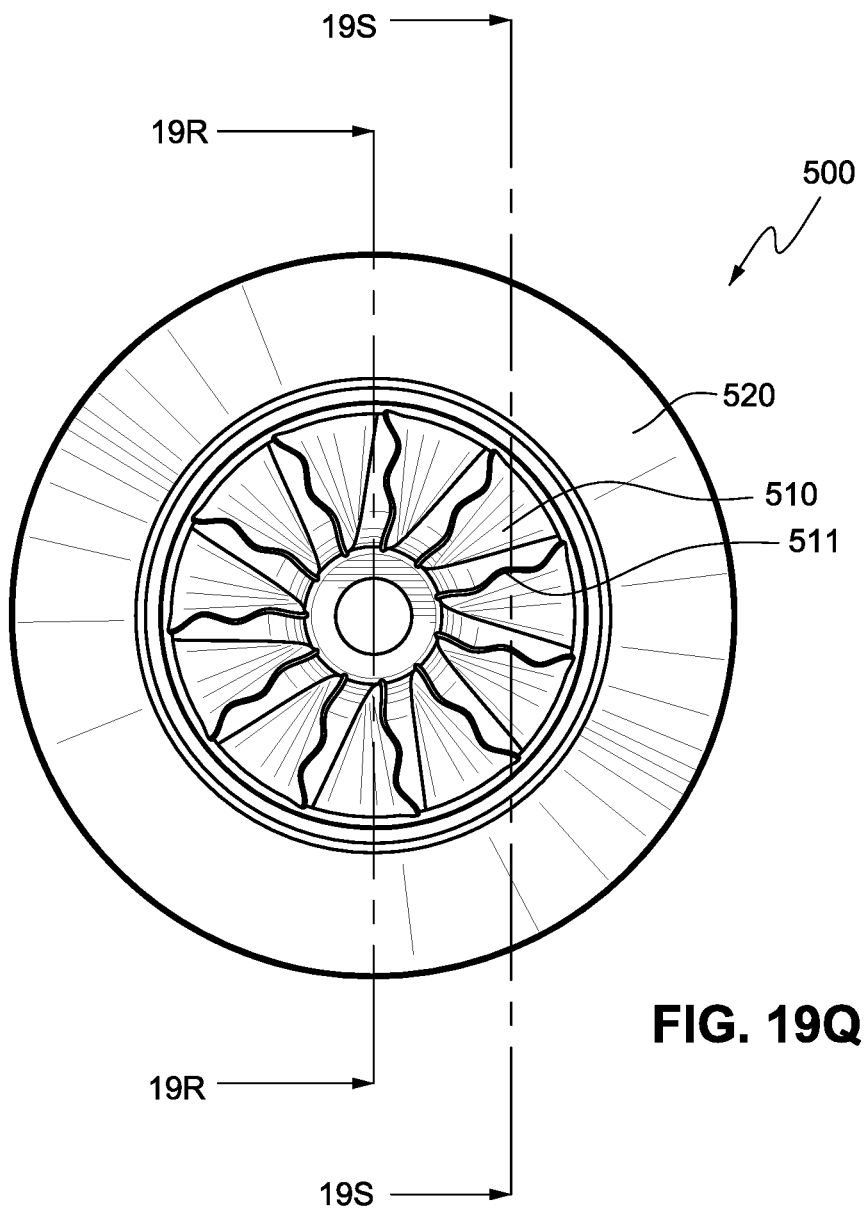
Figure 19R:
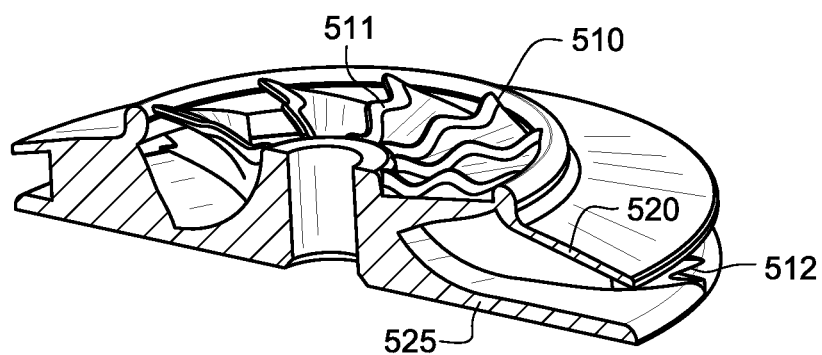
Figure 19S:
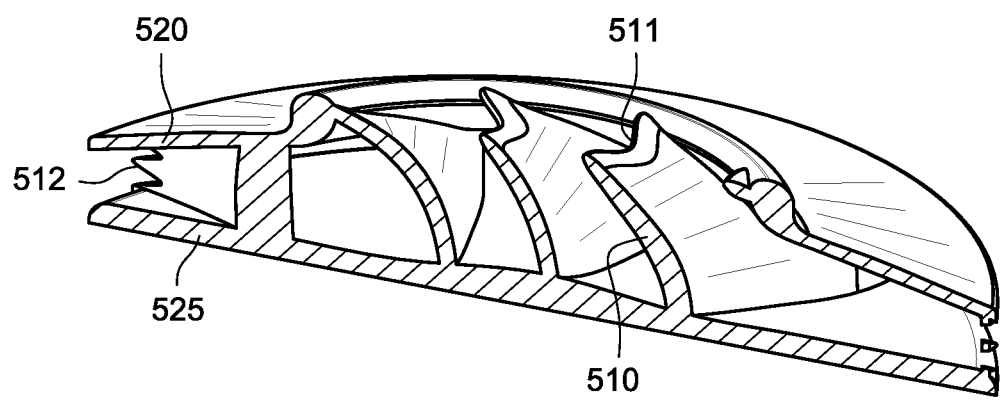

FIG. 19Q shows a plan view of the impeller shown in FIG. 19O, indicating cross-sections taken for FIGS. 19R-19S.

FIGS. 19R-19S show cross-sections of the impeller as indicated on FIG. 19Q.

Figure 19T:
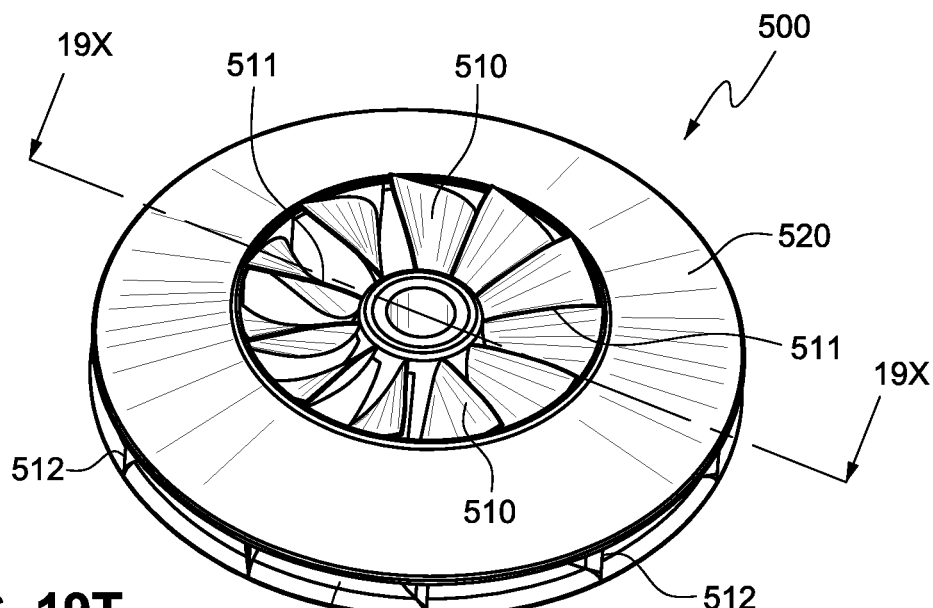

FIG. 19T shows an isometric view of an impeller in accordance with one form of the present technology.

Figure 19U:
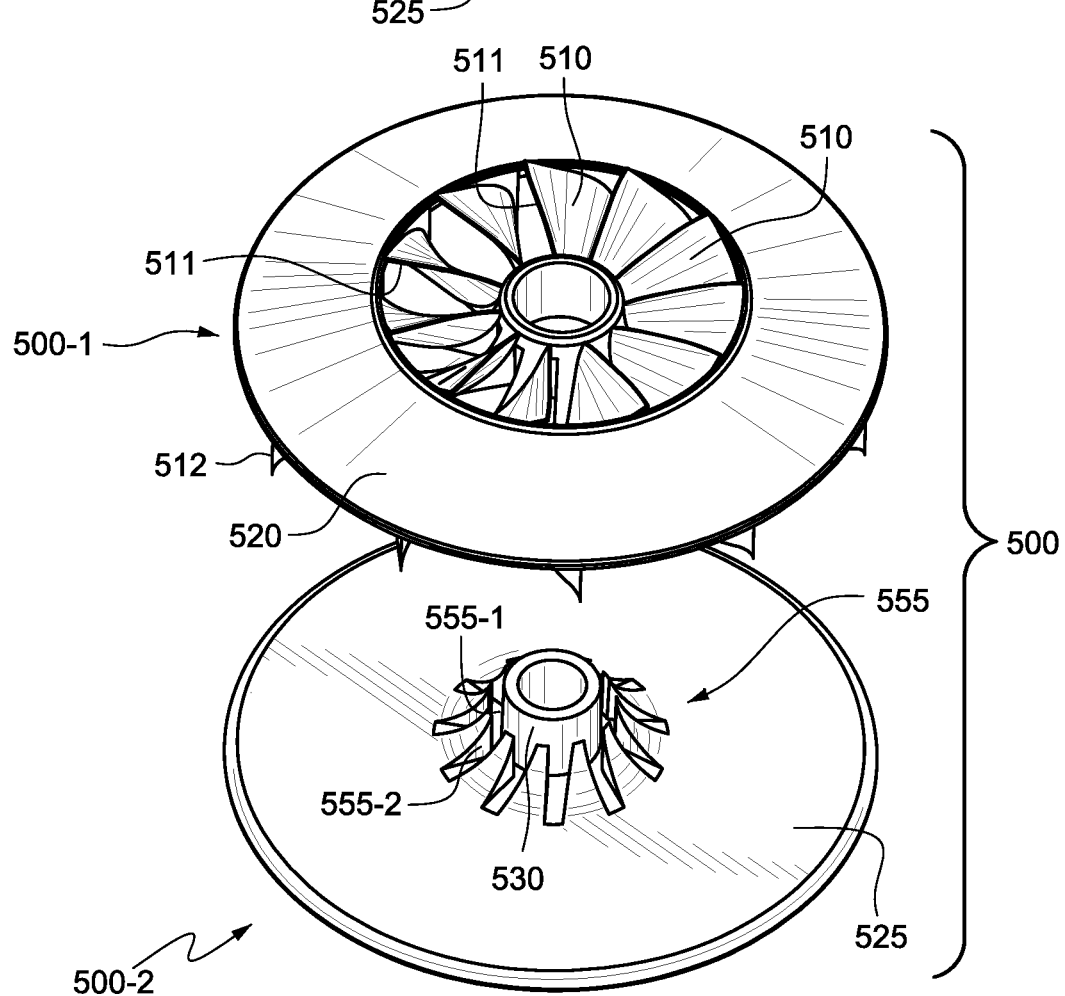

FIG. 19U shows an exploded view of the impeller shown in FIG. 19T.

Figure 19V:
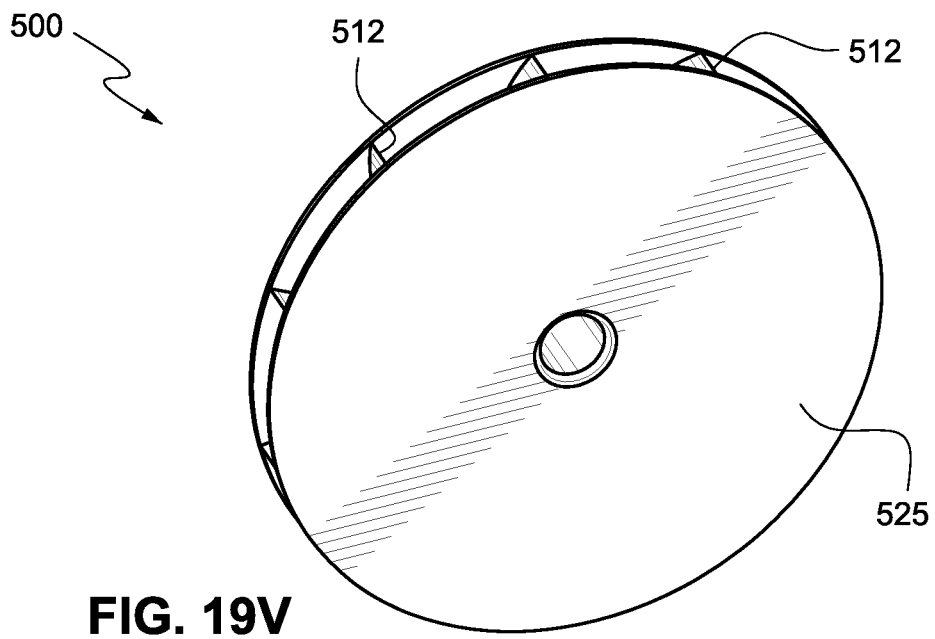

FIG. 19V shows a bottom isometric view of the impeller shown in FIG. 19T.

Figure 19W:
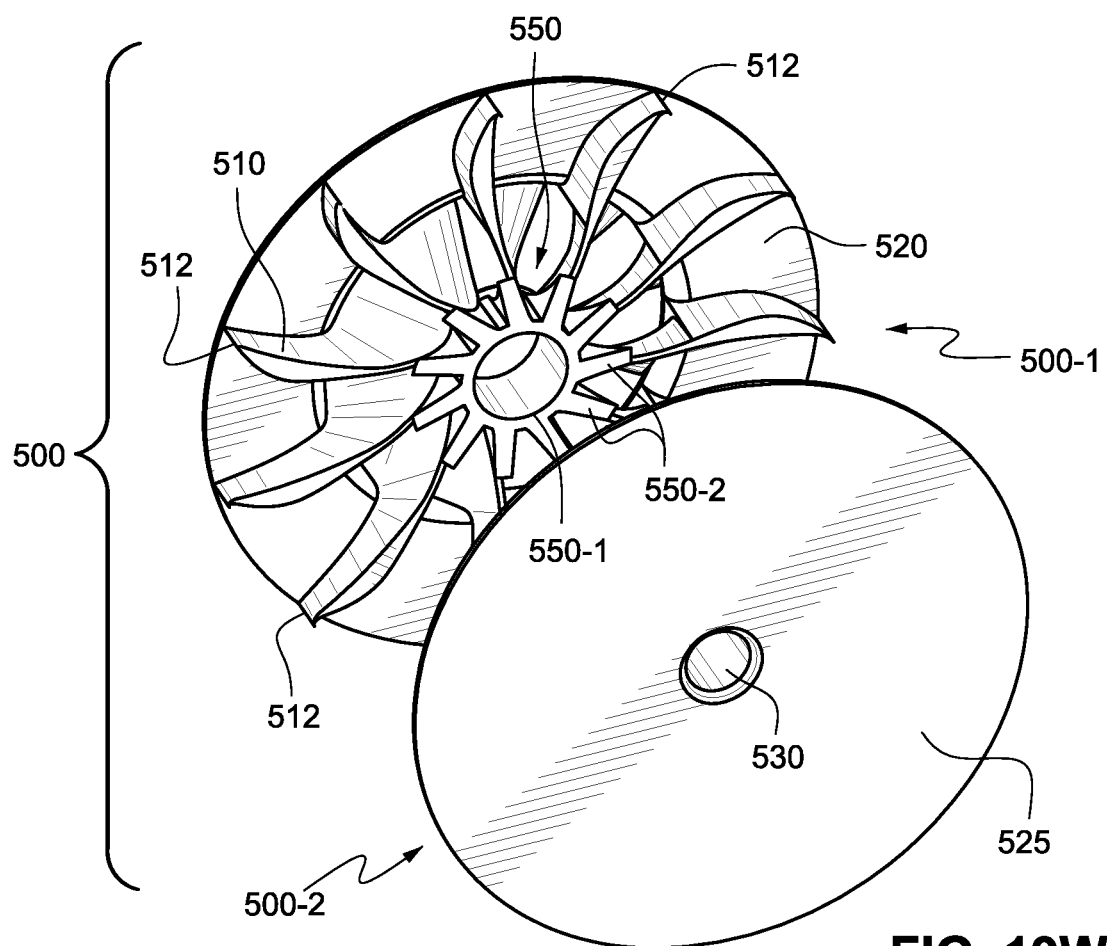

FIG. 19W shows an exploded view of the impeller shown in FIG. 19V.

Figure 19X:
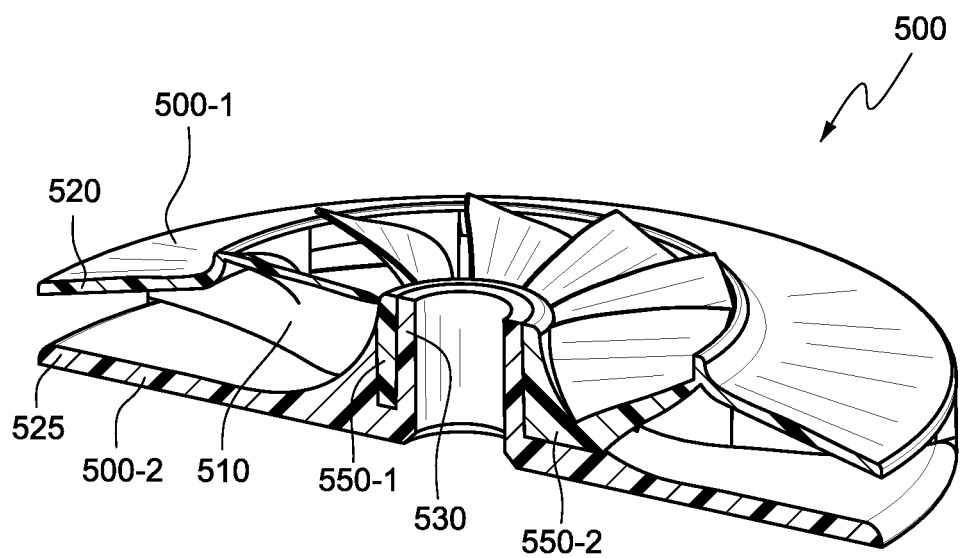

FIG. 19X shows a cross-section of the impeller as indicated on FIG. 19T.

Figure 19Y:
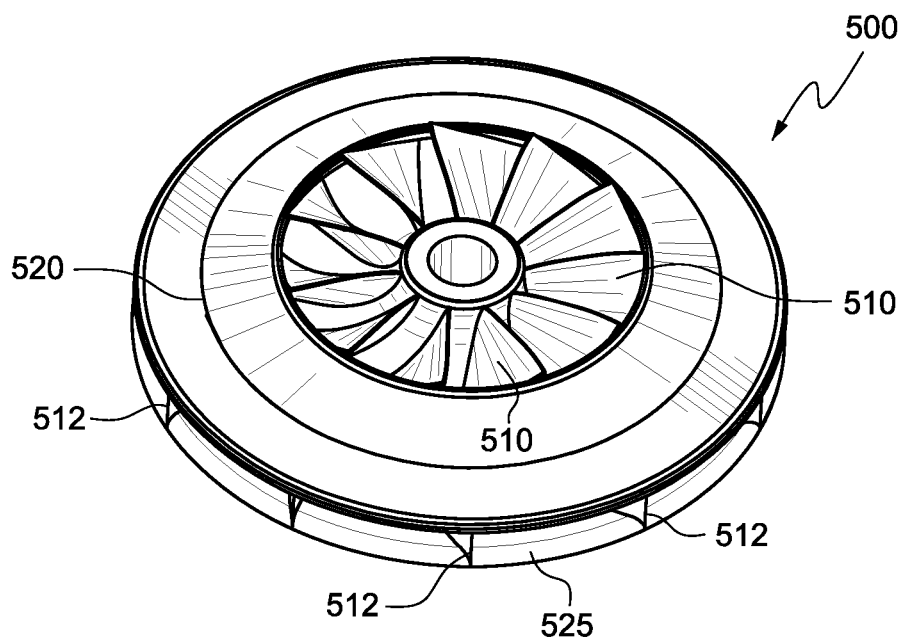

FIG. 19Y shows an isometric view of an impeller in accordance with one form of the present technology.

Figure 19Z:
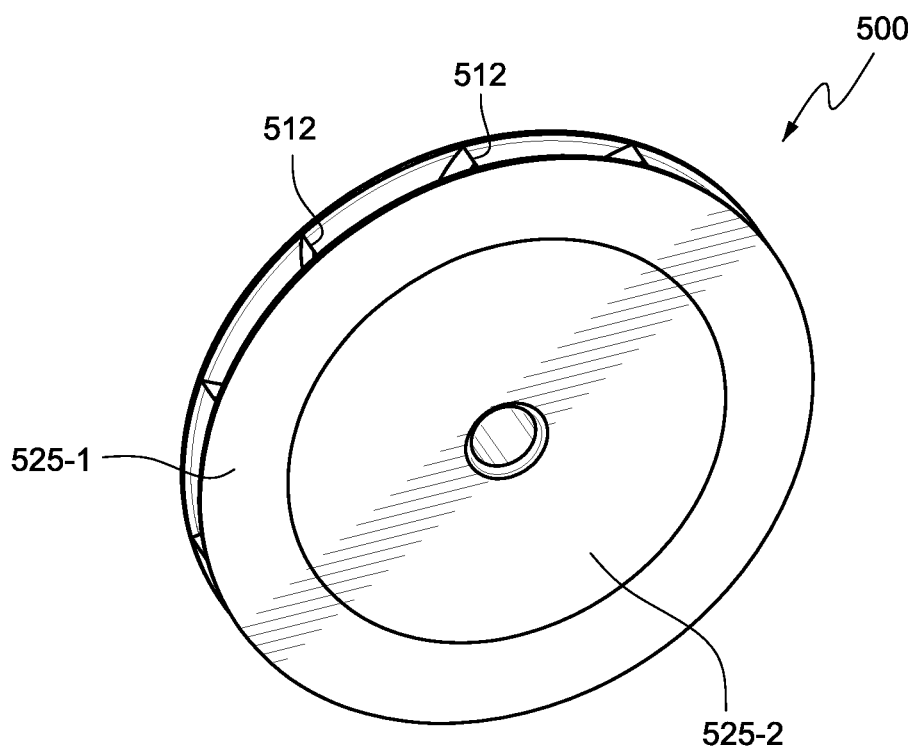
Figure 19A:
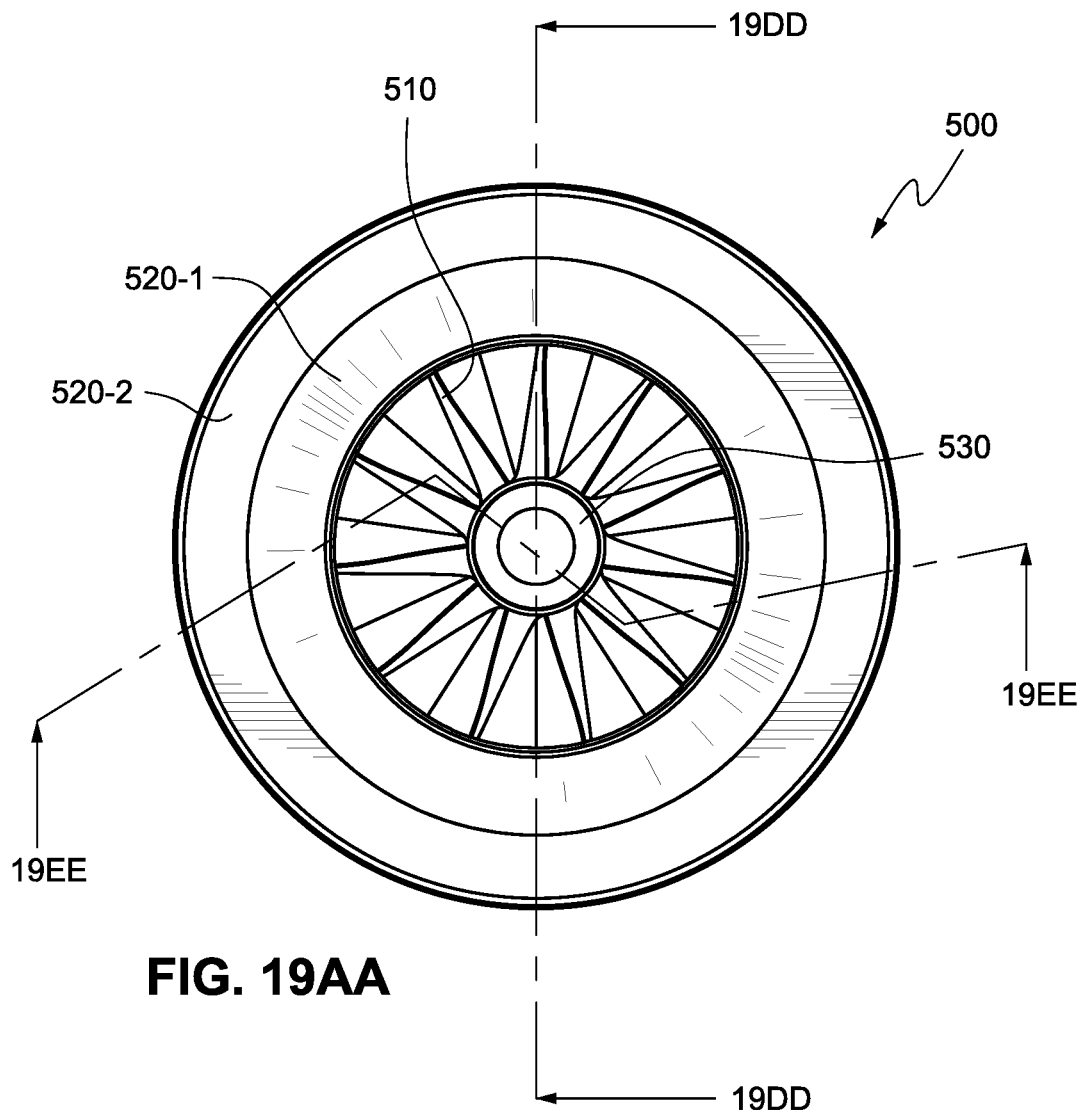
Figure 19B:
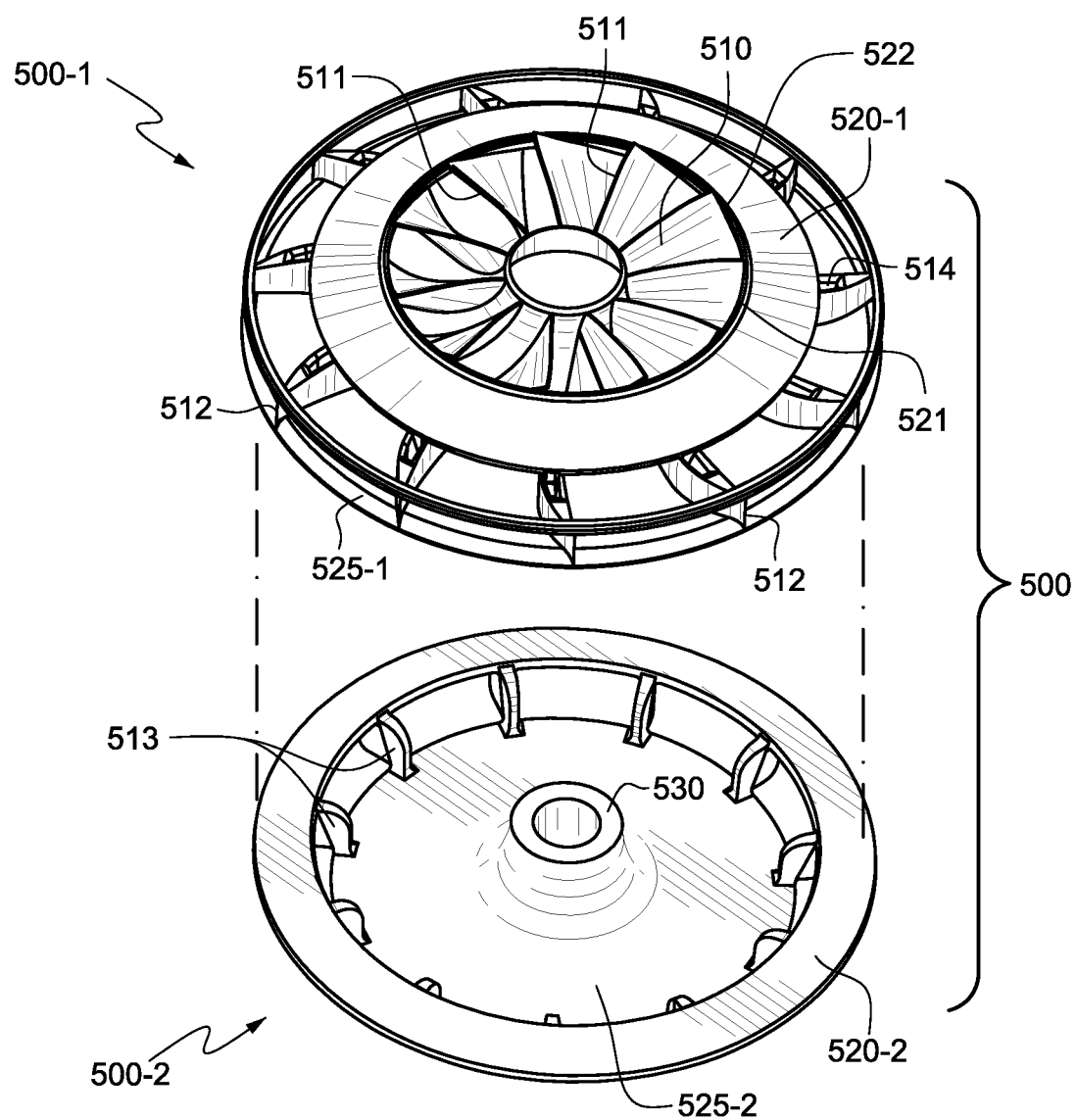
Figure 19C:
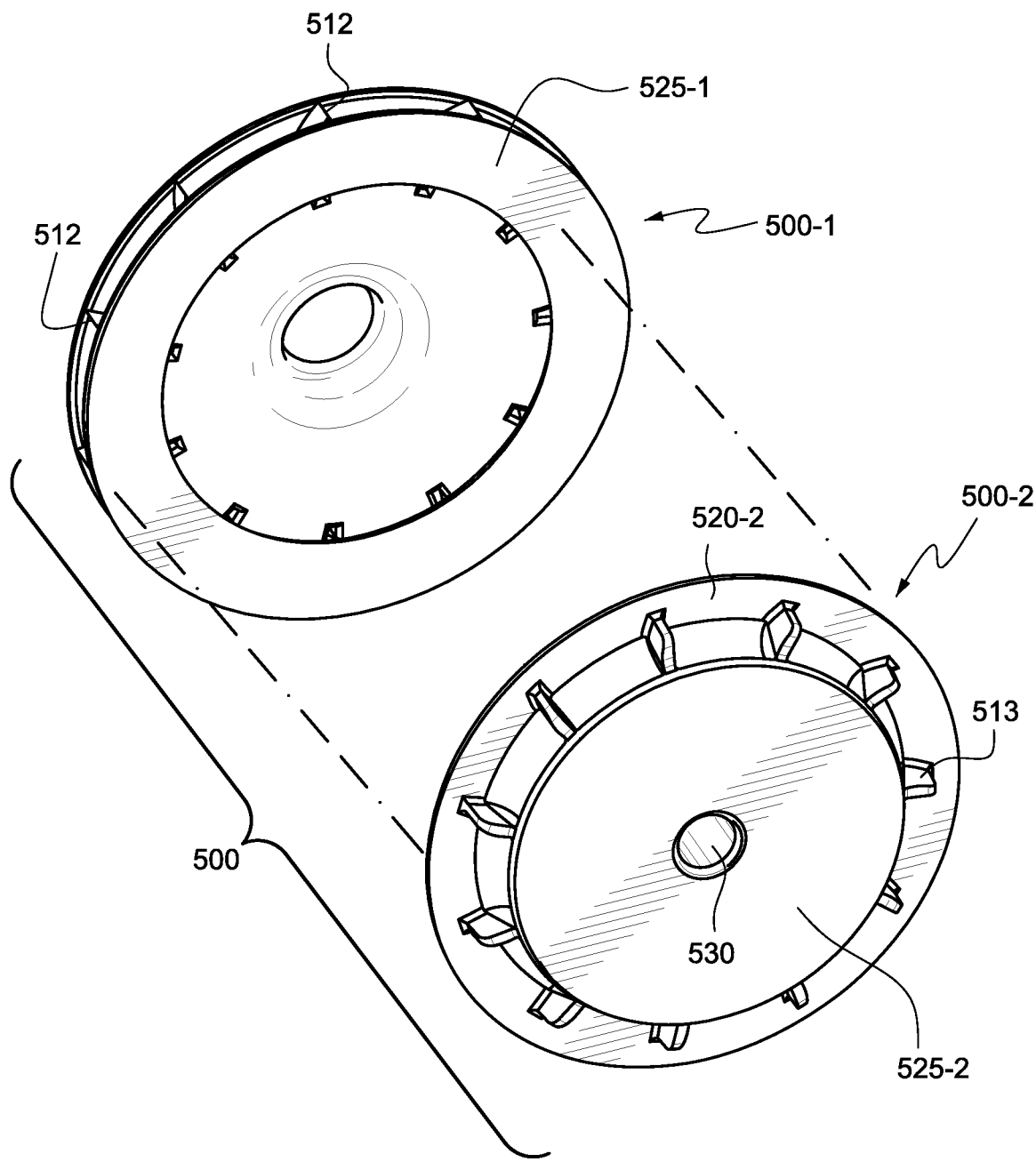
Figure 19D:
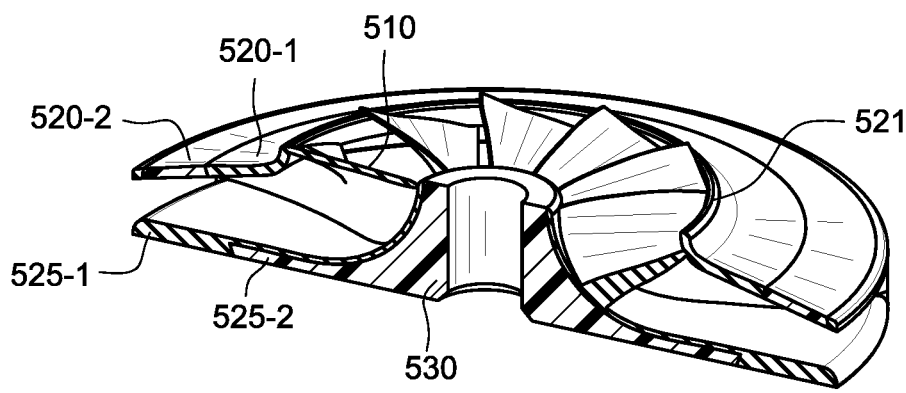
Figure 19E:
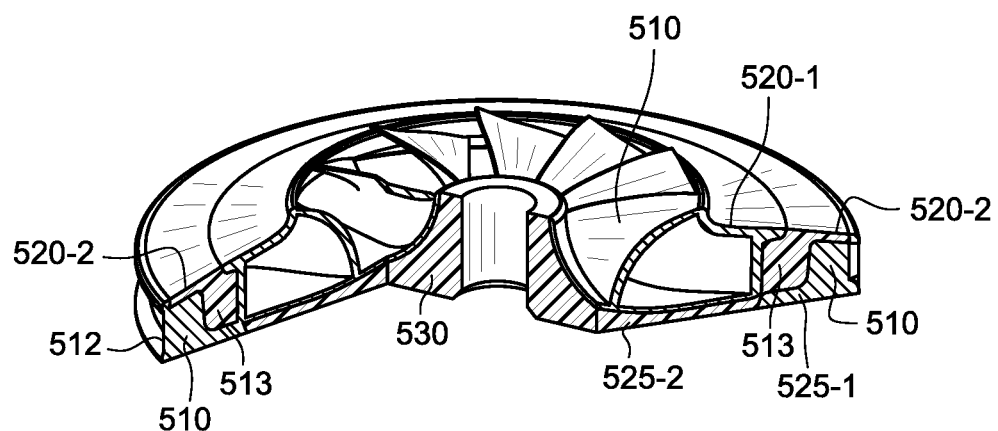
Figure 19F:
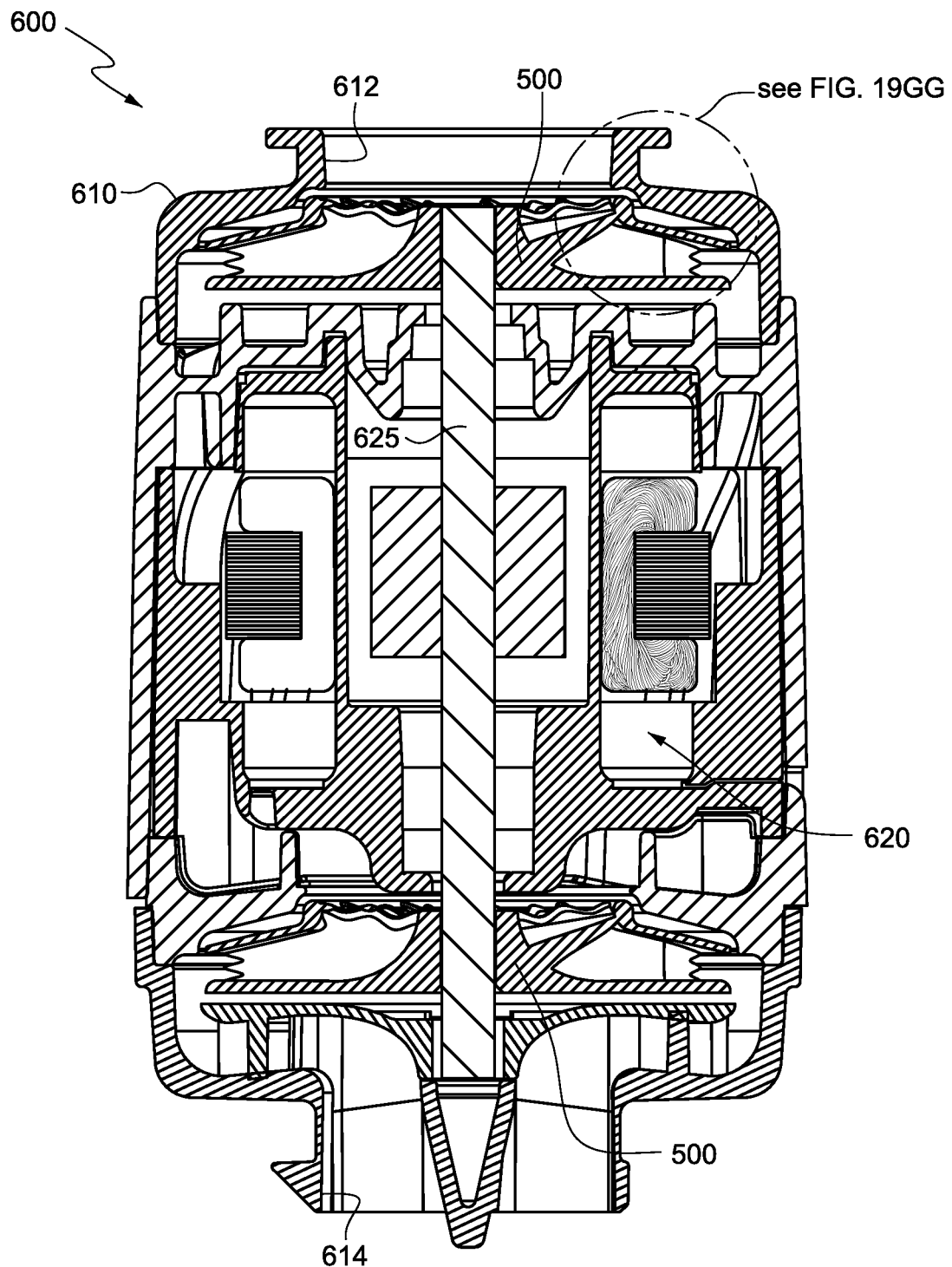
Figure 19G:
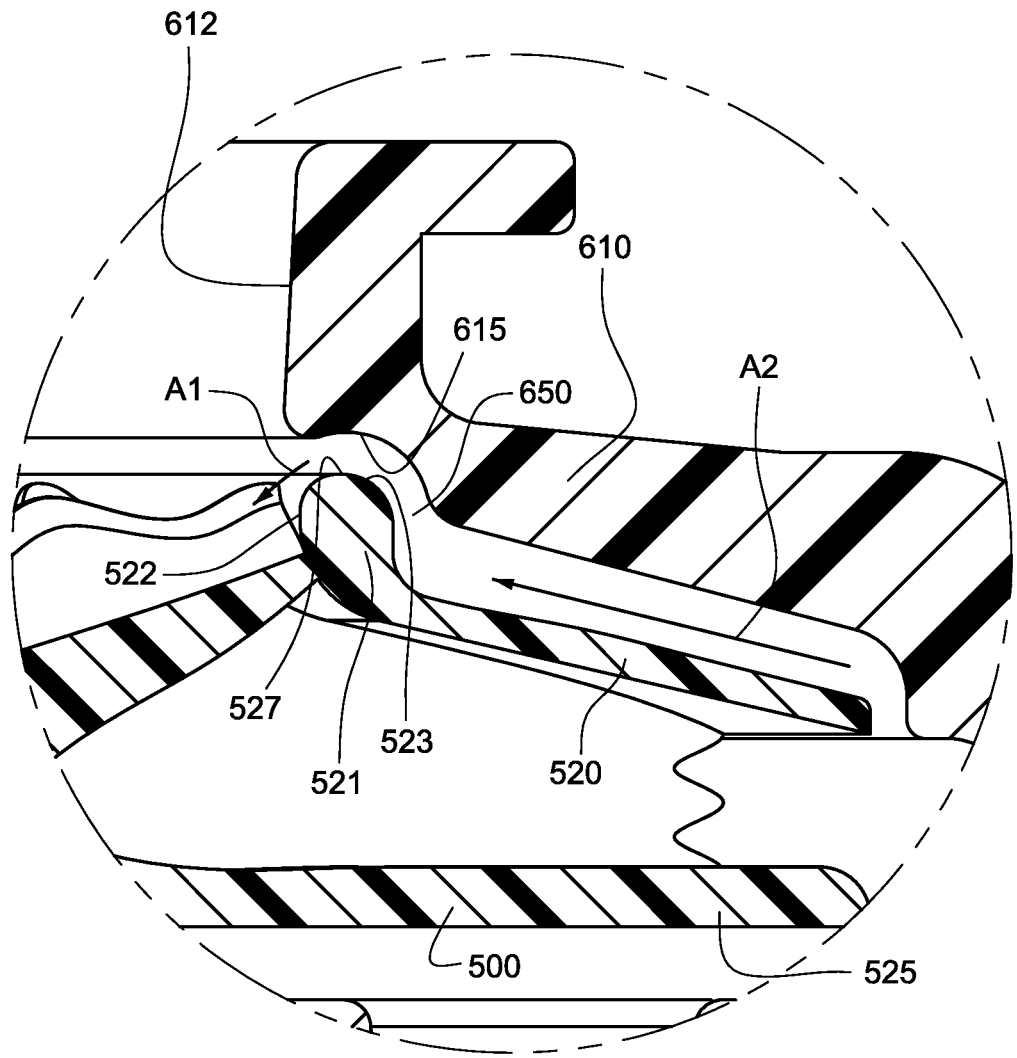

FIG. 19Z shows a bottom isometric view of the impeller shown in FIG. 19Y.

FIG. 19AA shows a plan view of the impeller shown in FIG. 19Y, indicating cross-sections taken for FIGS. 19DD-19EE.

FIG. 19BB shows an exploded view of the impeller shown in FIG. 19Y.

FIG. 19CC shows another exploded view of the impeller shown in FIG. 19Y.

FIGS. 19DD-19EE show cross-sections of the impeller as indicated on FIG. 19AA.

FIG. 19FF shows a cross-section of a blower for an RPT device including impellers in accordance with one form of the present technology.

FIG. 19GG is an enlarged portion of the blower as indicated on FIG. 19FF.

5 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

5.1 Therapy

In one form, the present technology comprises a method for treating a respiratory disorder comprising the step of applying positive pressure to the entrance of the airways of a patient 1000.

In certain examples of the present technology, a supply of air at positive pressure is provided to the nasal passages of the patient via one or both nares.

In certain examples of the present technology, mouth breathing is limited, restricted or prevented.

5.2 Treatment Systems

In one form, the present technology comprises an apparatus or device for treating a respiratory disorder. The apparatus or device may comprise an RPT device 4000 for supplying pressurised air to the patient 1000 via an air circuit 4170 to a patient interface 3000.

FIG. 6A depicts a schematic of a respiratory pressure therapy (RPT) system worn by a patient according to an example of the present technology. The RPT system includes a blower 4142 (FIG. 6B) to provide a flow of gas to the patient at a pressure greater than ambient, a seal-forming structure 3100 to form a seal with the entrance to the patient's airways, a plenum chamber 3200 (FIG. 6B) which supports the blower 4142 and is pressurized by the blower 4142 during therapy, a lateral portion of a tie of a positioning and stabilising structure 3303, a superior portion of a tie of a positioning and stabilising structure 3304, and a posterior portion of a tie of a positioning and stabilising structure 3305 to secure the RPT system to the patient during therapy, and a power supply 4210 to drive the blower and any other electrical components. Details of the various components of the exemplary RPT system are provided in the corresponding subsections below.

Figure 1:
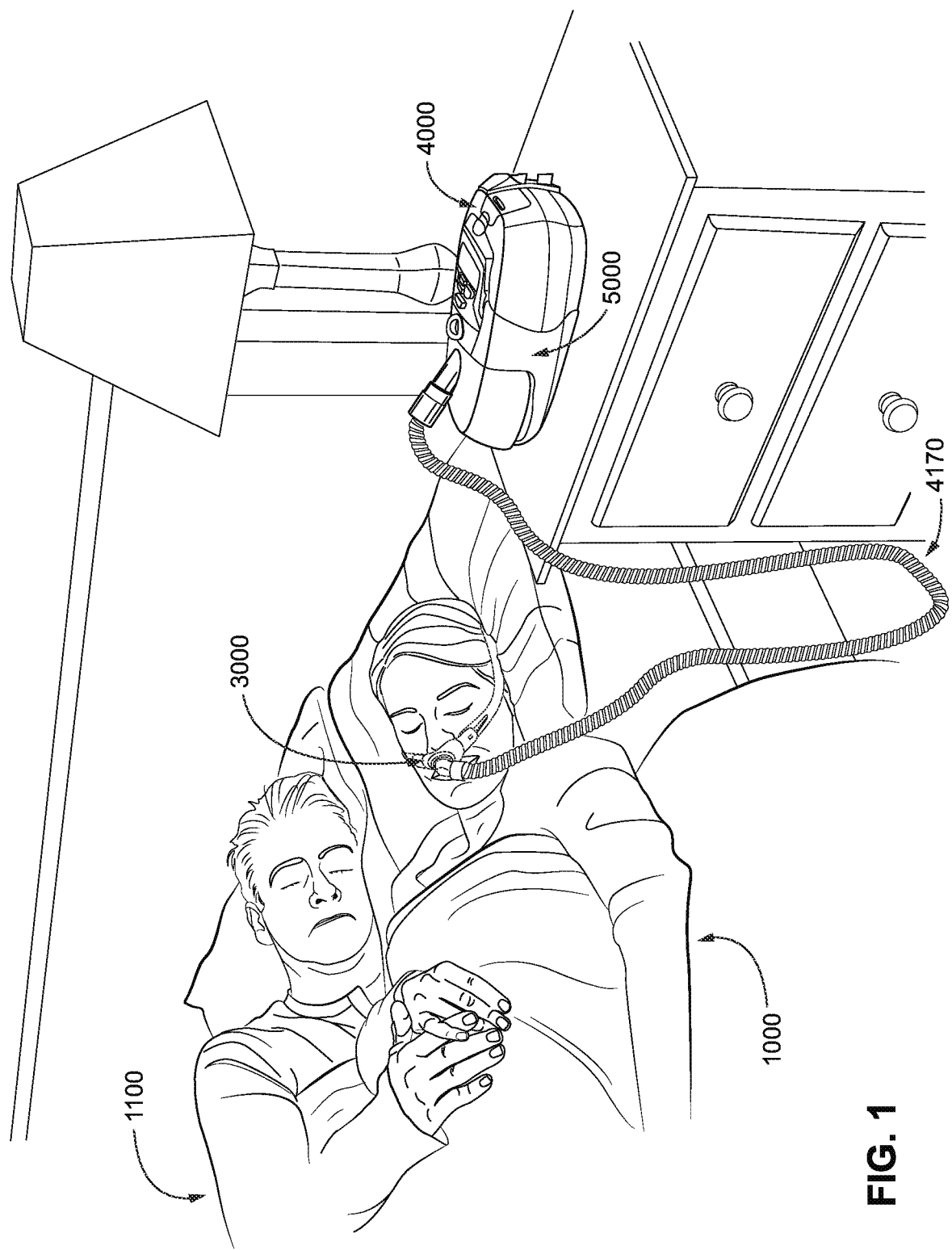
Figure 2:
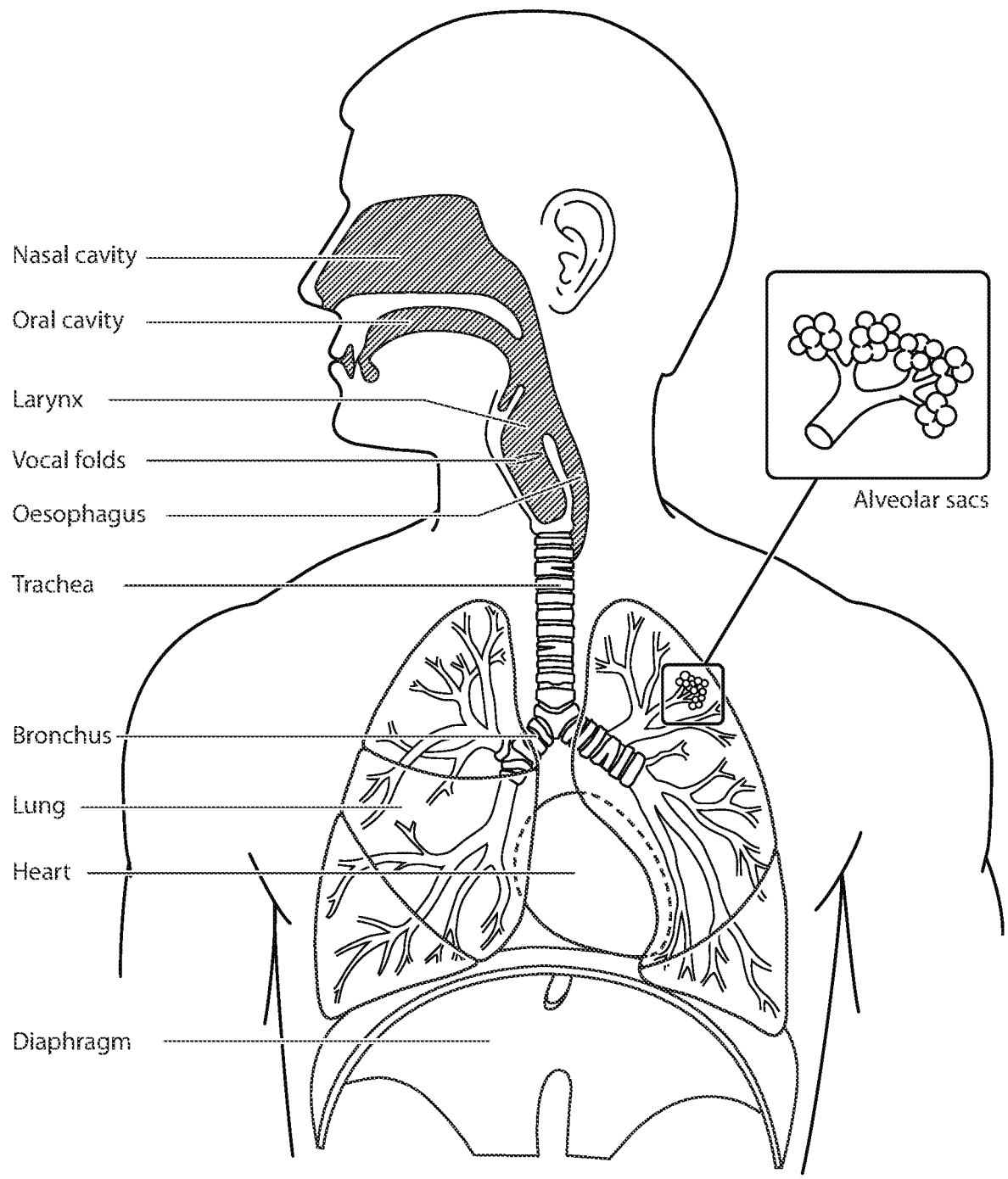
Figure 3:
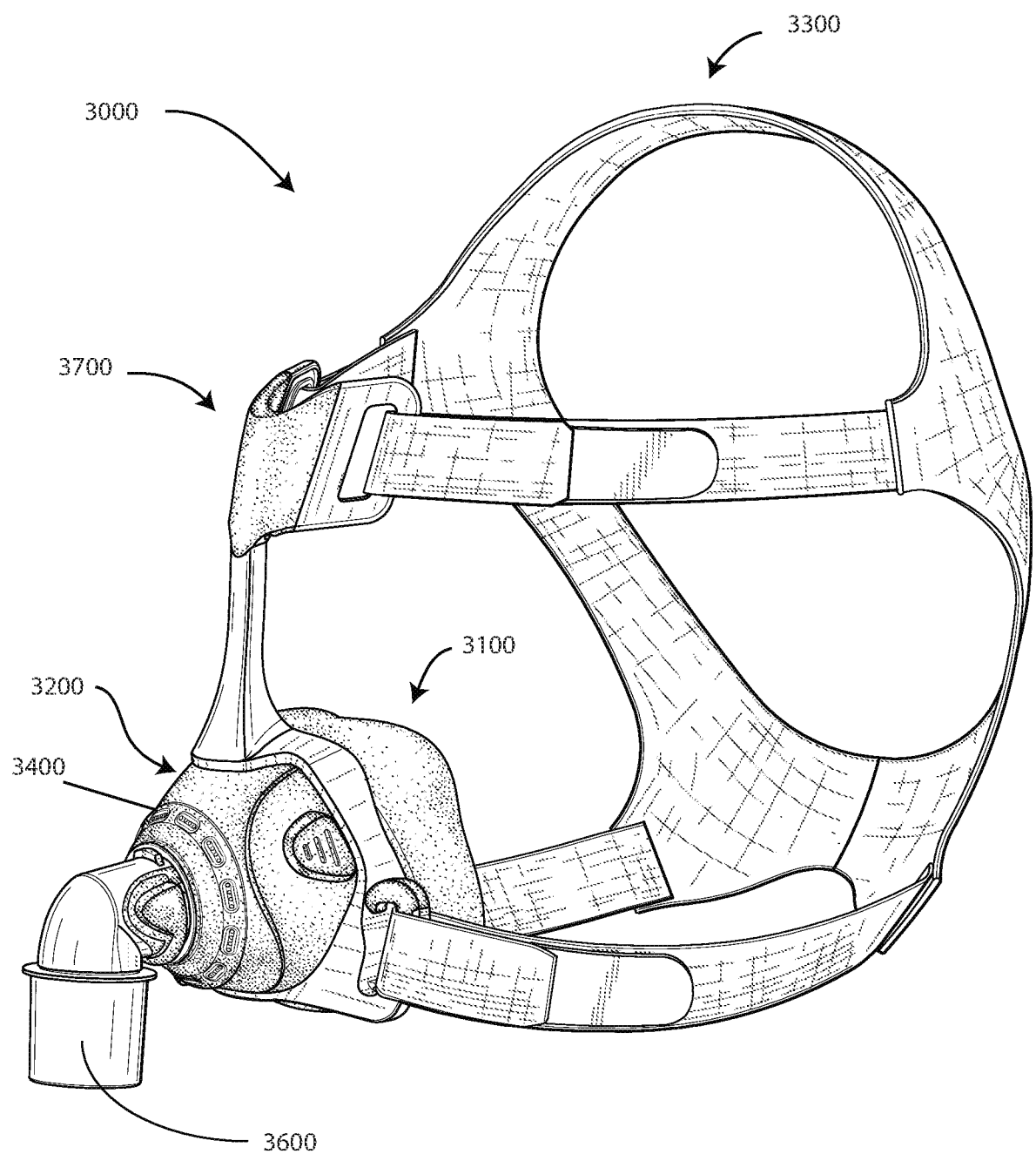
Figure 4A:
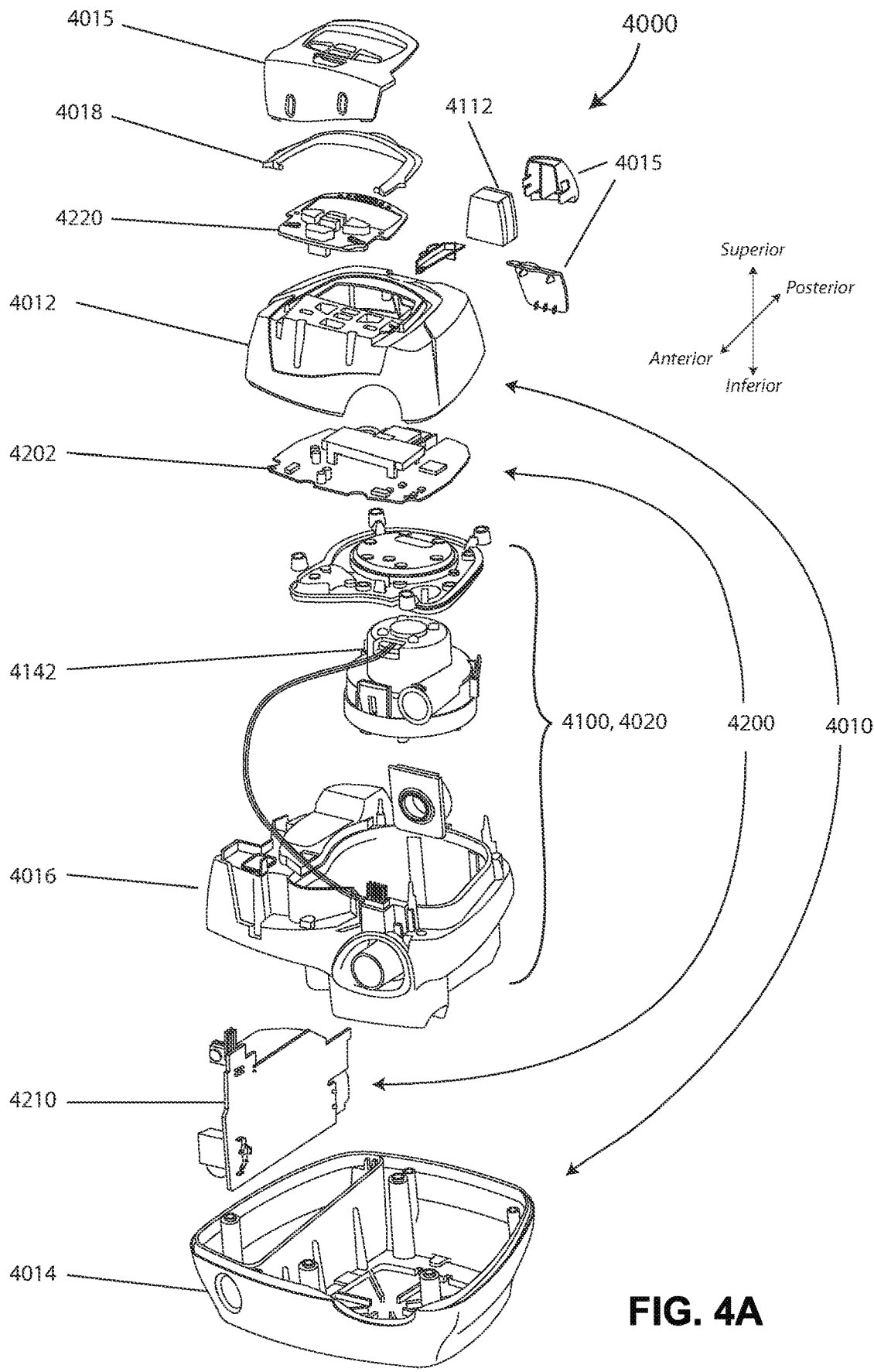
FIG. 4A shows an RPT device in accordance with one form of the present technology.
Figure 4B:
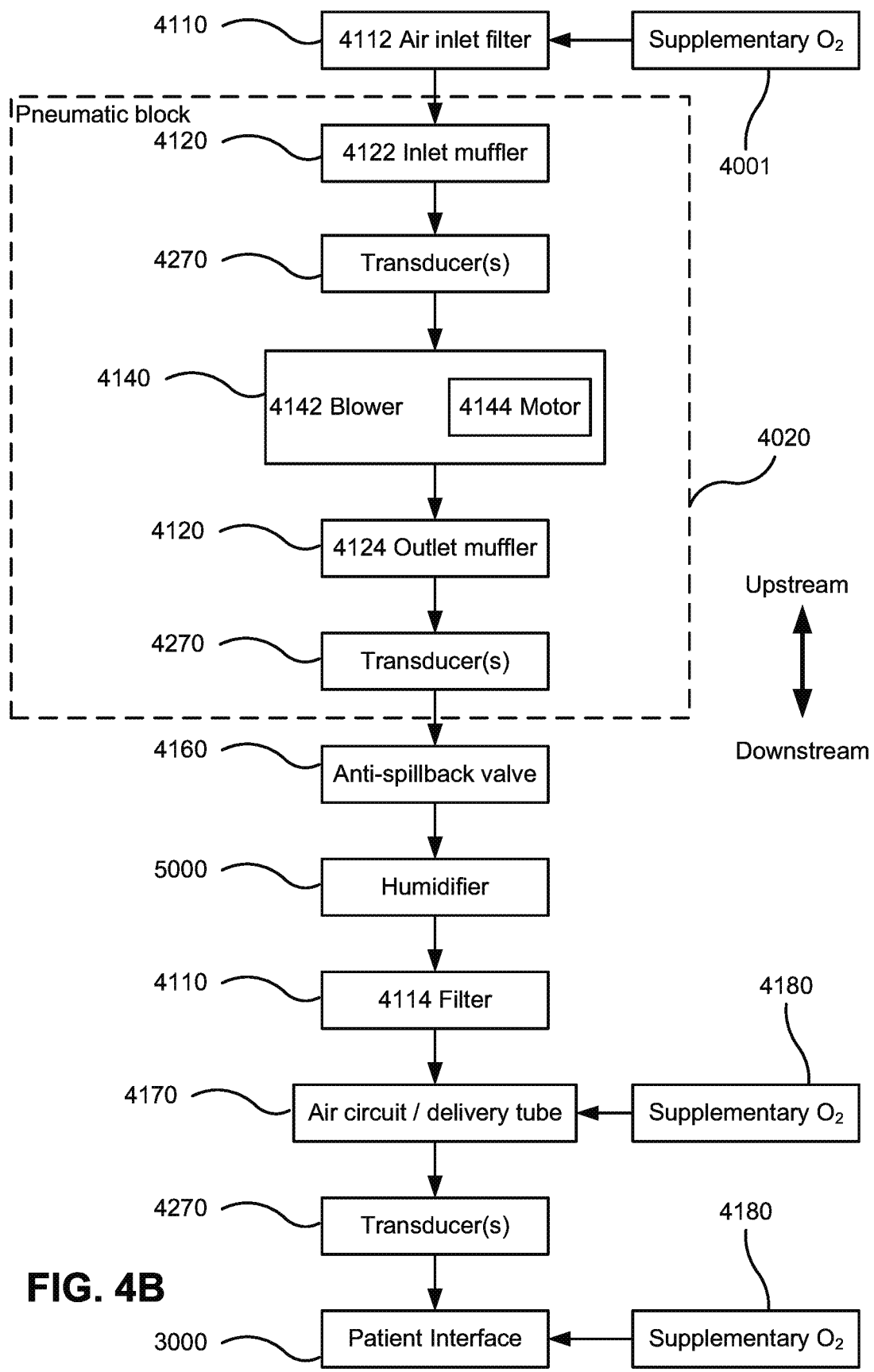
FIG. 4B is a schematic diagram of the pneumatic path of an RPT device in accordance with one form of the present technology. The directions of upstream and downstream are indicated.
Figure 4C:
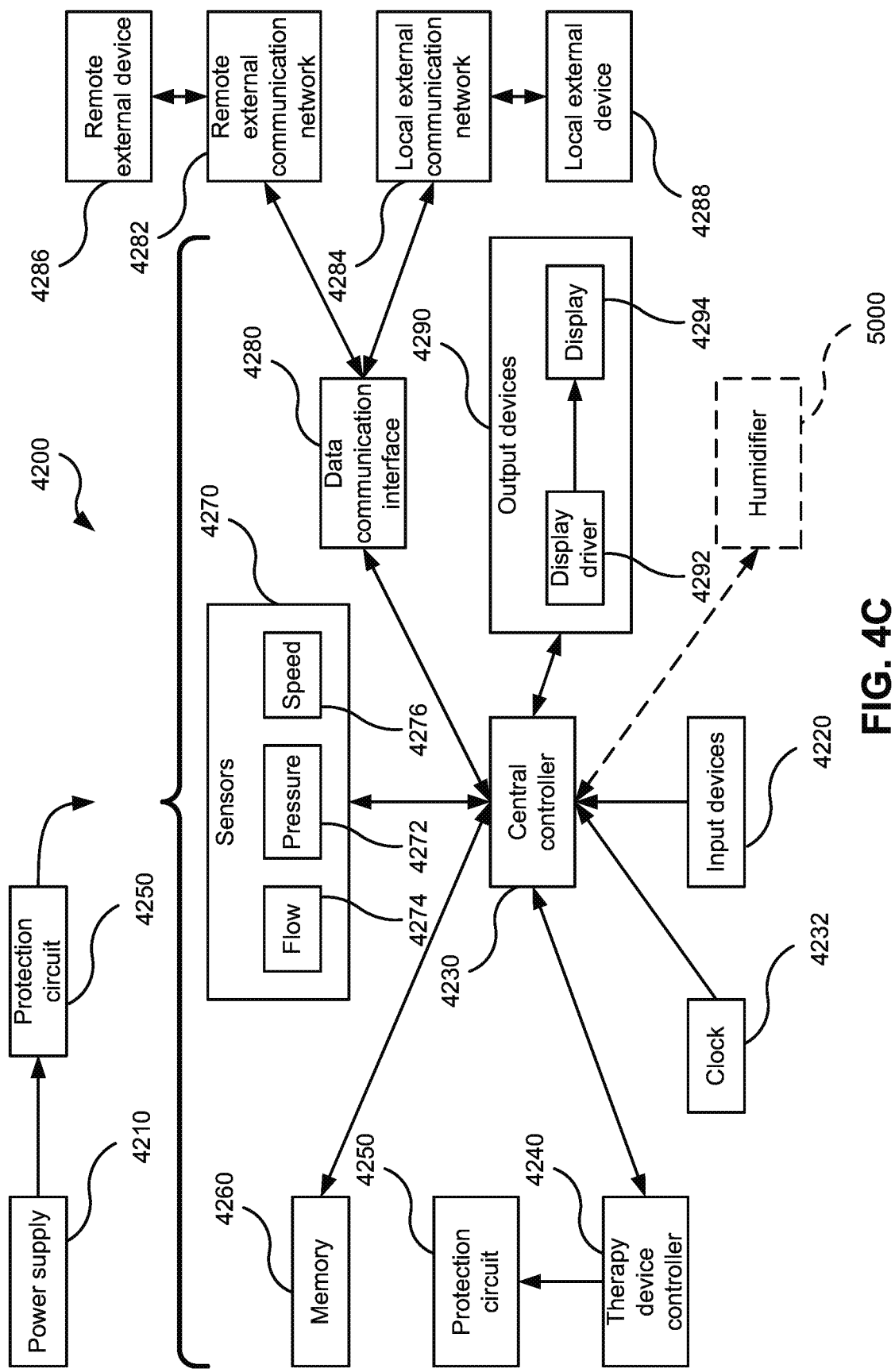
FIG. 4C is a schematic diagram of the electrical components of an RPT device in accordance with one form of the present technology.

According the example of the present technology that is depicted in FIG. 6A, the RPT system may be completely self-contained and patient-worn. In other words, all of the components need for RPT therapy are combined into one system that may be worn and supported entirely by the patient's head during use. Conventionally, RPT systems include a patient interface 3000 that is worn by the patient and includes a plenum chamber 3200 that is pressurized to the therapy pressure with a flow of gas, a seal-forming structure 3100 that forms a seal with the entrance to the patient's airways to provide a substantially sealed path for the flow of gas, and a positioning and stabilising structure 3300 that secures the seal-forming structure 3100 and plenum chamber 3200 during use. In such conventional systems, these are the only components that are actually supported on the patient's head. An example of these conventional systems are depicted in FIG. 1.

A respiratory pressure therapy (RPT) device 4000 is also provided in conventional systems to generate the flow of gas at a pressure greater than ambient. Due to the pressure and flow rate necessary for adequate therapy, the RPT device 4000 is typically a relatively large device that has been typically provided as a separate device that is supported near, but not on, the patient during therapy. In other words, prior art RPT devices 4000 are relatively large in size and weight due to technological limitations such that an adequate therapy pressure and flow rate can only be generated by such a large device that the patient cannot comfortably wear the RPT device during use. Accordingly, the RPT device 4000 is typically located on the patient's nightstand or similar structure to keep the RPT device 4000 in close proximity Since the patient will typically be in his or her bed wearing the patient interface 3000 and the RPT device 4000 is located nearby, an air circuit 4170 is also included to provide the flow of pressurised gas from the RPT device 4000 to the patient interface 3000. Furthermore, since the conventional RPT device 4000 is located at a distance from the patient such that the air circuit 4170 is required to deliver the flow of gas to the patient, the RPT device 4000 must be powerful enough to account for pressure losses associated with directing the flow of gas down the air circuit 4170 to the patient interface 3000.

While the overall arrangement described above has been the norm in respiratory therapy for several decades, the present technology represents an improvement by allowing the entire RPT system to be comfortably worn by the patient during therapy. The features described in detail below explain how the various components can be reduced in size and weight sufficiently for the patient to wear comfortably and, in cases where the RPT system is used to treat sleep-disordered breathing, sleep with the entire system on the head.

An example of the present technology depicted in FIG. 6A is a respiratory pressure therapy (RPT) system that includes a plenum chamber 3200 pressurisable to a therapeutic pressure of at least 6 cmH$_2$O above ambient air pressure. The RPT system also includes a seal-forming structure 3100 constructed and arranged to form a seal with a region of the patient's face at or surrounding an entrance to the patient's airways such that a flow of gas at said therapeutic pressure is delivered to at least the entrance to the patient's nares. The seal-forming structure 3100 may be constructed and arranged to maintain said therapeutic pressure in the plenum chamber 3200 throughout the patient's respiratory cycle in use. A positioning and stabilising structure 3300 constructed and arranged to hold the seal-forming structure in a therapeutically effective position on the patient's head may also be provided. The positioning and stabilising structure 3300 may include at least one tie. A lateral portion of the tie 3303 may be constructed and arranged to overlie a region of the patient's head superior to the otobasion superior in use. A superior portion 3304 of the tie may be constructed and arranged to overlie a region of the patient's head in a region of the parietal bone in use. A posterior portion 3305 of the tie may be constructed and arranged to overlie a region of the patient's head in a region of the occipital bone in use. The positioning and stabilising structure 3300 may include a non-rigid decoupling portion. The RPT system may also include a blower 4142 that is configured to generate the flow of gas and pressurise the plenum chamber 3200 to the therapeutic pressure. The blower 4142 may be connected to the plenum chamber 3200 such that the blower 4142 is supported from the patient's head in use. The blower 4142 may be arranged with respect to the patient's head in use such that the axis of rotation of the motor 4145 is perpendicular to the patient's sagittal plane. A power supply 4210 to provide electrical power to the blower 4142 may also be included in the RPT system. The plenum chamber 3200, seal-forming structure 3100, and the blower 4142 may be arranged so as not to extend beyond the patient's mental protuberance in use.

FIGS. 15A-15C and 16A-16C depict other examples of the RPT system of the present technology. FIG. 17 depicts the RPT system in isolation, i.e., not worn by a patient, and without the positioning and stabilizing structure 3300. These examples include the primary components described above and in greater detail below, including, inter alia, the seal-forming structure 3100, the plenum chamber, the positioning and stabilising structure 3300, the blower 4142 (not visible in these views), the vent assembly 3400, the power supply 4210, and the central controller 4230. These examples will be described in greater detail below.

5.3 Patient Interface

A non-invasive patient interface 3000 in accordance with one aspect of the present technology comprises the following functional aspects: a seal-forming structure 3100, a plenum chamber 3200, a positioning and stabilising structure 3300, a vent or vent assembly 3400, and a forehead support 3700. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

If a patient interface is unable to comfortably deliver a minimum level of positive pressure to the airways, the patient interface may be unsuitable for respiratory pressure therapy.

The patient interface 3000 in accordance with some forms of the present technology may be constructed and arranged to be able to provide a supply of air at a positive pressure of at least 6, 10 or 20 cmH$_2$O with respect to ambient.

As described in the preceding subsection, the RPT system of the present technology may be understood to comprise a number of the basic elements of a conventional patient interface 3000 that are described below in greater detail, e.g., a seal-forming structure 3100, a plenum chamber 3200, and a positioning and stabilising structure 3300. The exemplary RPT system of the present technology improves upon the conventional patient interface 3000 by adding the blower 4142 directly to the patient interface 3000, e.g., on the plenum chamber 3200, to provide the pressurised flow of gas. Thus, the blower 4142 may be understood to be suspended or supported on the patient's head by the patient interface. The power supply 4210 may also be provided directly to the patient interface 3000, e.g., on the positioning and stabilising structure 3300, to provide electrical power to the blower 4142 and any other components as needed. By arranging the blower 4142 and the power supply 4210 on the patient interface 3000, the need for the air circuit 4170 and any other wires or connections extending from the patient is eliminated. Accordingly, undesirable effects and forces on the patient interface 3000, such as tube drag caused by the air circuit 4170 may be reduced or eliminated.

5.3.1 Seal-Forming Structure

In one form of the present technology, a seal-forming structure 3100 provides a target seal-forming region, and may additionally provide a cushioning function. The target seal-forming region is a region on the seal-forming structure 3100 where sealing may occur. The region where sealing actually occurs—the actual sealing surface—may change within a given treatment session, from day to day, and from patient to patient, depending on a range of factors including for example, where the patient interface was placed on the face, tension in the positioning and stabilising structure and the shape of a patient's face.

In certain forms of the present technology, the seal-forming structure 3100 is constructed from a biocompatible material, e.g., silicone rubber.

A seal-forming structure 3100 in accordance with the present technology may be constructed from a soft, flexible, resilient material such as silicone.

In another form of the present technology, the RPT system is supported on the patient's head solely by the sealing engagement of the seal-forming structure 3100 with the entrance(s) to the patient's airways. For example, the seal-forming structure 3100 may comprise prongs or nasal inserts that are inserted into the patient's nares and the prongs or nasal inserts are shaped and dimensioned to provide a sufficiently rigid connection to allow the RPT system to be supported only by that connection. Thus, the positioning and stabilising structure 3300 features described below may be eliminated completely from the RPT system or the positioning and stabilising structure 3300 may at least be further simplified.

The seal-forming structure 3100 of the present technology may comprise a silicone cushion that encloses the blower 4142 and is connected to the plenum chamber 3200 such that the blower 4142 is supported by the positioning and stabilising structure 3300 and the seal-forming structure 3100 in use. In other words, the seal-forming structure 3100 may be configured to suspend the RPT system by providing a location for support and engagement with the patient's face. Accordingly, the seal-forming structure 3100 may also isolate vibration generated by the blower 4142 from the patient's face.

The seal-forming structure 3100 of the present technology may be constructed such that no part thereof enters the patient's mouth in use. Also, the seal-forming structure 3100 of the present technology may be constructed such that it does not extend internally of the patient's airways. As described above, the seal-forming structure 3100 of the present technology may comprise a pair of nasal puffs, or nasal pillows, each nasal puff or nasal pillow being constructed and arranged to form a seal with a respective naris of the nose of the patient. The seal-forming structure 3100 of the present technology may form a seal in use on a nose bridge region or on a nose-ridge region of the patient's face and may form a seal in use on an upper lip region of the patient's face. The seal-forming structure 3100 of the present technology may form a seal in use on a nose bridge region or on a nose-ridge region of the patient's face and may form a seal in use on a chin-region of the patient's face.

The seal-forming structure 3100 of the present technology may comprise an elastically deformable material that is less rigid than the plenum chamber 3200. For example, the elastically deformable material may be silicone rubber, e.g., liquid silicone rubber (LSR) or compression molded silicone rubber (CMSR). A portion of the seal-forming structure 3100 may substantially enclose the plenum chamber 3200 and the blower 4142 while allowing at least an inlet 4143 of the blower 4142 to remain exposed. The seal-forming structure 3100 may be shaped and dimensioned to at least partially isolate the patient's head from vibration and dampen sound generated by the blower 4142 in use. The elastically deformable material of the seal-forming structure 3100 may be selected to at least partially isolate the patient's head from vibration and dampen sound generated by the blower 4142 in use.

Elastic deformability of the seal-forming structure 3100 may help the RPT system absorb motion of the heavier components (e.g., the blower 4142) to allow the RPT system to remain in place during use. Otherwise, if the seal-forming structure 3100 provided too stiff of an interface with the patient's head, the patient's movements might disrupt the connection. Furthermore, constructing the seal-forming structure 3100 from a material with vibration isolation and/or dampening properties may be advantageous where the motor 4145 of the blower 4142 is capable of high rotational speeds (e.g., 50,000 rpm to 80,000 rpm) and/or where the control system may change the rotational speed frequently during therapy such that the torque associated with speed changes causes the RPT system to move relative to the patient's head. Accordingly, the vibration dampening properties of the material may help to isolate the patient's head from what would otherwise be disruptive forces transferred to the patient's head. In addition, a reduced inertia of the blower, such as from a reduced diameter of an impeller, may further improve a performance of the seal-forming structure 3100.

Alternatively, the RPT system may comprise a cover constructed of an elastically deformable material that is less rigid than the plenum chamber 3200. The cover may substantially enclose the plenum chamber 3200 and the blower 4142 while allowing at least an inlet 4143 of the blower 4142 to remain exposed. The cover may be shaped and dimensioned to at least partially isolate the patient's head from vibration and dampen sound generated by the blower 4142 in use. The elastically deformable material of the cover may be selected to at least partially isolate the patient's head from vibration and dampen sound generated by the blower 4142 in use. In this alternative, a seal-forming structure 3100 may be included with the features described above, but may be a separate component from the cover. Such a construction may be advantageous so that the materials, shape, and dimensions of the seal-forming structure 3100 can be optimized for its intended functions, while allowing the materials, shape, and dimensions of the cover to be optimized for its intended functions.

The examples shown in FIGS. 15A-15C, 16A-16C, and 17 include a seal-forming structure 3100. The seal-forming structure 3100 in these examples is in the form of nasal pillows, each forming an individual seal with the corresponding nostril. However, other variations are envisioned, such as a nasal cushion that provides the flow of pressurized gas to the patient's nostrils but not the mouth, a nasal cradle cushion that provides the flow of pressurized gas to the patient's nostrils but not the mouth and that seals at the base of the patient's nose and does not extend above the bridge or the tip of the patient's nose, a full-face cushion with a single opening that provides the flow of pressurized gas to the patient's nostrils and mouth, or an oro-nasal cushion that includes separate openings to provide the flow of pressurized gas to the patient's nose and mouth separately.

In the examples shown in FIGS. 15A-15C, 16A-16C, and 17, the seal-forming structure 3100 is connected to the plenum chamber 3200 at the upper housing portion 4132. The connection may be permanent (i.e., the seal-forming structure 3100 cannot be separated from the upper housing portion 4132 without damaging one or both components) or the seal-forming structure 3100 may be removable to allow for cleaning or replacement. The seal-forming structure 3100 may be made from a flexible material such as liquid silicone rubber, and may be overmolded to the upper housing portion 4132 in the permanent connection variation. Alternatively, the permanent connection may be formed by molding the seal-forming structure 3100 onto the upper housing portion 4132 such that a mechanical interlock is formed. In the removable connection examples, the upper housing portion 4132 and the seal-forming structure 3100 may include structures shaped to form a mechanical interlock that is separable by deforming one or both of the upper housing portion 4132 and the seal-forming structure 3100.

5.3.2 Plenum Chamber

The plenum chamber 3200 of the exemplary RPT system may be formed by at least one housing portion. In the example depicted in FIGS. 6A-6C, an upper housing portion 4132 and a lower housing portion 4133 form the plenum chamber 3200. Also in this example, the blower 4142 may be contained at least partially within the plenum chamber 3200 such that when the blower 4142 is operated the plenum chamber 3200 is pressurized by the flow of gas generated by the blower 4142. The upper housing portion 4132 may also have a plenum chamber outlet 4131. The flow of gas generated by blower 4142 may pass through the plenum chamber 3200 to at least the entrance to the patient's nares in use via the plenum chamber outlet 4131. Actual contact with the face is provided by the seal-forming structure 3100. The seal-forming structure 3100 may be joined to and extend in use about the entire perimeter of at least the plenum chamber outlet 4131. In some forms, the plenum chamber 3200 and the seal-forming structure 3100 are formed from a single homogeneous piece of material.

The upper housing portion 4132 and the lower housing portion 4133 may be at least partially separable to allow the blower 4142 to be removed from the plenum chamber 3200. For example, the housing portion(s) may be joined at one side in a clamshell arrangement to allow the plenum chamber 3200 to be opened and closed so that the blower 4142 can be removed. Thus, beneficially, a user may be able to choose from a plurality of patient interfaces to use with the blower 4142 according to the user's preference.

According to some form of the present technology, a kit may comprise a blower 4142 and one of: a plurality of plenum chambers 3200 configured to receive the blower 4142, and/or a plurality of positioning and stabilising structures 3300. The kit may comprise further components such as a power supply, to allow a user to configure and/or assemble an RPT system for use according to their preferences from such a kit.

The housing portion(s) of the plenum chamber 3200 may also comprise at least one sealing structure to seal between the upper housing portion 4132 and the lower housing portion 4133 and/or along the line of separation in the clamshell arrangement described above.

In another example of the present technology, the entire plenum chamber 3200, e.g., between the upper housing portion 4132 and the lower housing portion 4133, may be comprised of an elastically deformable material, such as silicone. The plenum chamber 3200 according to this example may comprise two separate pieces, i.e., the upper housing portion 4132 and the lower housing portion 4133, that are joined together to form the plenum chamber 3200 or the plenum chamber 3200 may comprise a single structure, e.g., in which the upper housing portion 4132 and the lower housing portion 4133 are formed from a single, homogeneous piece of material.

In certain forms of the present technology, the plenum chamber 3200 is at least partly constructed from a transparent material, e.g., a transparent polycarbonate. The use of a transparent material can reduce the obtrusiveness of the patient interface, and help improve compliance with therapy. The use of a transparent material can aid a clinician to observe how the patient interface is located and functioning.

In certain forms of the present technology, the plenum chamber 3200 is at least partly constructed from a translucent material. The use of a translucent material can reduce the obtrusiveness of the patient interface, and help improve compliance with therapy.

In one form, the plenum chamber 3200 may comprise a lower housing portion 4133 constructed from a soft, damped material such as silicone, and an upper housing portion 4132 constructed from a rigid material such as a polycarbonate. Alternatively, FIGS. 6D and 6E depict a variation that excludes the upper housing portion 4132 such that the seal-forming structure 3100 would be directly connected to the lower housing portion 4133, which would reduce dead space within the plenum chamber 3200.

Additionally, FIG. 6E shows a heat and moisture exchanger (HME) 6000 positioned within the lower housing portion 4133 and supported by the HME retention structure 4135.

The plenum chamber 3200 may also include at least one attachment structure 4130 to attach the positioning and stabilising structure 3300 to secure the RPT system to the patient's head in use. The example depicted in FIGS. 6A-6C shows the attachment structure 4130 formed integrally with the lower housing portion 4133 as one homogeneous piece of material. The attachment structure 4130 may also be a separate component that is attached to one of the housing portions of the plenum chamber 3200. The attachment structure 4130 may be joined to the positioning and stabilising structure 3300 by clips or by looping straps of the positioning and stabilising structure through corresponding attachment structures 4130.

The RPT system of the present technology may also comprise a heat and moisture exchanger (HME) that absorbs heat and moisture from gas exhaled by the patient. The heat and moisture absorbed by the HME during therapy may then be transferred to the flow of gas generated by the blower 4142 to humidify the flow of gas before it reaches the patient's airways. Providing the RPT system with an HME may obviate the need for conventional powered humidification. According to the example depicted in FIGS. 6A-6C, the HME may be located within the plenum chamber 3200 such that it that is positioned in the flow of gas and downstream of the blower 4142. As can be seen in FIG. 6B, an HME retention structure 4135 is provided on the lower housing portion 4133 to retain the HME within the plenum chamber 3200, but the HME retention structure 4135 may be provided on the upper housing portion 4132 instead, may be a part of the HME or may be a separable part altogether. As will be described below, the HME may be provided within the plenum chamber 3200 and downstream of the blower 4142 because the RPT system may be unvented such that the patient's exhalate travels along the same path but in an opposite direction to the flow of gas generated by the blower 4142 for therapy. Therefore, the inhaled and exhaled flows of gas will both pass through the HME.

The HME of the present technology may be made of a foam material or a paper material. Other porous materials are also envisioned. Accordingly, the HME may also act as a filter.

The examples shown in FIGS. 15A-15C, 16A-16C, and 17 include a plenum chamber 3200 that may be formed by the upper housing portion 4132 and the lower housing portion 4133. In the examples shown in FIGS. 6A-6C, the upper housing portion 4132 and the lower housing portion 4133 are separate components that may be joined together to form the plenum chamber 3200 and to allow access to components therein. However, in the examples shown in FIGS. 15A-15C, 16A-16C, and 17, the upper housing portion 4132 and the lower housing portion 4133 are a single, unitary component that forms the plenum chamber 3200.

In the examples shown in FIGS. 16A-16C and 17, the upper housing portion 4132 includes a vent assembly 3400 that is described in greater detail below. The vent assembly 3400 permits gas to be discharged to atmosphere to expel $CO_2$ exhaled by the patient, which prevents undesirable $CO_2$ rebreathing. The examples shown in FIGS. 15A-15C do not include a vent assembly 3400.

5.3.3 Positioning and Stabilising Structure

The seal-forming structure 3100 of the patient interface 3000 of the present technology may be held in sealing position in use by the positioning and stabilising structure 3300, such as when the RPT device is in operation, and/or not in operation.

In one form of the present technology, a positioning and stabilising structure 3300 is provided that is configured in a manner consistent with being worn by a patient while sleeping.

In one form of the present technology, a positioning and stabilising structure 3300 is provided with a decoupling portion located between an anterior portion of the positioning and stabilising structure 3300 and a posterior portion of the positioning and stabilising structure 3300. The decoupling portion does not resist compression and may be, e.g., a flexible or floppy strap. The decoupling portion is constructed and arranged so that when the patient lies with their head on a pillow, the presence of the decoupling portion prevents a force on the posterior portion from being transmitted along the positioning and stabilising structure 3300 and disrupting the seal.

In one form of the present technology, a positioning and stabilising structure 3300 comprises a strap constructed from a laminate of a fabric patient-contacting layer, a foam inner layer and a fabric outer layer.

In certain forms of the present technology, a positioning and stabilising structure 3300 comprises a strap that is extensible, e.g., resiliently extensible.

In some forms, the positioning and stabilising structure 3300 may be configured to allow, or support, transmission of at least one of power and/or signals. For example, the positioning and stabilising structure 3300 may comprise, or support thereon, an electrically conductive portion configured to provide electrical communication therethrough.

In the example of the RPT system depicted in FIG. 6A, the positioning and stabilising structure 3300 may comprise at least one wire 3301 supported by the positioning and stabilising structure 3300. The wire(s) 3301 may provide electrical communication between the blower 4142 and the power supply 4210, e.g., a battery, such as for power and/or signalling. The wire(s) 3301 may be contained within a lateral portion 3303 of the positioning and stabilising structure 3300, e.g., one or more of the ties that pass superior or inferior to the patient's otobasion superior. The wire 3301 may comprise a relatively thin cross-section so as to maintain a low-profile and not be uncomfortable for the patient. The wire 3301 may be configured such that its rigidity is relatively small in comparison to that of the supporting positioning and stabilising structure 3300, so as to not significantly prevent the positioning and stabilising structure from conforming to the patient's face. In one example, the wire 3301 may be in the form of a flexible printed circuit (FPC). Such a configuration may beneficially allow a patient to sleep comfortably at night while using the RPT system to receive respiratory treatment.

For example, the wire 3301 may have a thickness of less than 3 mm. The wire 3301 may be as thin as 0.5 mm, 0.2 mm or 0.1 mm, allowing the lateral portion 3303 to be flexible and/or thin, such that it may conform readily to the contours of the patient's face or head without being uncomfortable. The wire 3301 may be covered in the lateral portion 3303, such as by being encapsulated or covered, for example in silicone, foam or in a fabric material. The power supply 4210 may be provided to the superior portion 3304 of the positioning and stabilising structure 3300 such that the wire(s) 3301 pass from the power supply 4210 to the blower 4142 thought the lateral portion of the tie 3303. Of course, the wire 3301 may comprise one or more layers (e.g. for insulation and/or further shielding) in addition to its conductive portions, such as polyester layers in FPC.

The positioning and stabilising structure 3300 may also include at least one tube 3302 in fluid communication with the plenum chamber 3200 at a first end via the port 4134 and a pressure transducer at a second end. The tube(s) 3302 may be contained within the lateral portion 3303 of the positioning and stabilising structure 3300, e.g., one or more of the ties that pass superior or inferior to the patient's otobasion superior.

The positioning and stabilising structure 3300 may also include a rigidiser arm to increase the rigidity of the lateral ties that join to the plenum chamber 3200 at the attachment structures 4130. Since the entire RPT system may be supported on the patient's head, the relatively soft and flexible materials of the positioning and stabilising structure 3300 alone may be insufficiently rigid to support the RPT system in use, in particular the blower 4142, the plenum chamber 3200, and the seal-forming structure 3100. By adding rigidiser arms to the lateral ties of the positioning and stabilising structure 3300, the weight of the RPT system can be more adequately supported in the desired position and only exceptional outside forces would be able to disrupt the sealing engagement with the patient's airways. The rigidiser may also at least partly cover a wire 3301 such as on one side of the wire 3301 or enclose the wire.

Furthermore, the length of at least one of the ties of the positioning and stabilising structure 3300 may be adjustable to allow the patient to set the tension generated by the positioning and stabilising structure 3300. Thus, the patient can ensure that the RPT system, in particular the positioning and stabilising structure 3300, fits comfortably while maintaining an adequate seal and a desired position.

The examples shown in FIGS. 15A-15C and 16A-16C include a positioning and stabilising structure 3300. The positioning and stabilising structure 3300 of these examples may include lateral portions 3303 that pass along respective sides of the patient's head. The lateral portions 3303 may pass above the patient's ears. The lateral portions 3303 may pass below the patient's eyes. The positioning and stabilising structure 3300 of these examples may include a posterior portion 3305 that may be adjustable. For example, the posterior portion 3305 may include a tab 3306 that forms a hook-and-loop connection to secure the posterior portion 3305 at the desired length. The posterior portion 3305 may be include one of hook or loop material and the tab 3306 may include the other of hook and loop material. An adjustment mechanism 3308 may also be provided to allow adjustment of the superior portion 3304 to accommodate patient heads of different sizes and shapes.

The positioning and stabilising structure 3300 in the examples shown in FIGS. 15A-15C and 16A-16C may also include one or more wires 3301 that may provide power from a power supply 4210 to the blower 4142. Also, the wire(s) 3301 may provide control signals to the blower 4142 from the central controller 4230. Additionally, if one or more sensors are included, e.g., a pressure sensor within the plenum chamber 3200, the one or more sensors may communicate signals to the central controller 4230 via the wire(s) 3301. The wire(s) 3301 may be secured to lateral portions 3303 and/or superior portions 3304 by one or more retainers 3307. Additionally, the central controller 4230 may be secured to the positioning and stabilising structure 3300 with one or more retainers 4231, e.g., at the lateral portion 3303 or the superior portion 3304. Also, the power supply 4210 may be secured to the positioning and stabilising structure 3300 with one or more retainers (not shown), e.g., at the lateral portion 3303 or the superior portion 3304. The power supply 4210 and/or the central controller 4230 may be contained with a housing that is connected to the positioning and stabilising structure 3300, such as via retainers, adhesives or other methods, such as overmoulding.

5.3.4 Vent

In one form, the patient interface 3000 includes a vent or vent assembly 3400 constructed and arranged to allow for the washout of exhaled gases, e.g., carbon dioxide.

In certain forms, the vent or vent assembly 3400 is configured to allow a continuous vent flow from an interior of the plenum chamber 3200 to ambient whilst the pressure within the plenum chamber is positive with respect to ambient. The vent or vent assembly 3400 is configured such that the vent flow rate has a magnitude sufficient to reduce rebreathing of exhaled CO2 by the patient while maintaining the therapeutic pressure in the plenum chamber in use.

One form of vent or vent assembly 3400 in accordance with the present technology comprises a plurality of holes, for example, about 20 to about 80 holes, or about 40 to about 60 holes, or about 45 to about 55 holes.

The vent or vent assembly 3400 may be located in the plenum chamber 3200. Alternatively, the vent or vent assembly 3400 is located in a decoupling structure, e.g., a swivel.

The exemplary RPT system depicted in FIGS. 6A-6C, may not include a vent, e.g., the plenum chamber 3200 may be unvented. Thus, in use the patient may exhale only through the blower 4142 in opposition to the direction of the flow of gas generated by the blower 4142 for therapy, e.g., while the blower 4142 continues to operate, and the patient's exhalate exits the RPT system through the blower inlet 4143. Accordingly, exhalation flow would travel through the blower 4142 to vent to the atmosphere. Moreover, the entire flow of gas traveling through the blower 4142 may reverse direction during the patient's exhalation phase, because the flow of the patient's exhalation exceeds the flow generated by the blower 4142. To facilitate venting exhalate through the blower 4142 and the blower inlet 4143, the blower 4142 may be arranged near the plenum chamber outlet 4131 and the seal-forming structure 3100 so that the blower 4142 is, therefore, near the patient. In such an arrangement, the blower 4142 should be sufficiently close to allow enough the exhalate to exit the RPT system prior to the patient beginning to inhale. Furthermore, the RPT system may be configured to allow breathing out through the blower inlet 4143 with minimal pneumatic resistance.

By arranging the blower 4142 near the patient and allowing venting of exhalate only through the blower 4142 and the blower inlet 4143, the overall flow rate required to be generated by the blower 4142 is reduced because it is not necessary to account for the vent flow. In other words, no vent leak is present during the patient's inhalation that needs to be driven by the flow of gas generated by the blower 4142. This arrangement may also increase the blower's 4142 efficiency by reducing the length of the flow path between the blower 4142 and the patient, i.e., through the plenum chamber, as a result of a reduction in pressure losses and leak.

In another alternative, the RPT system may be vented with an electronically actuated vent or a pneumatically actuated vent to improve efficiency of the RPT system, e.g., the blower 4142, by reducing unnecessary vent leak and reducing the length of the flow path. Suitable examples of electronically actuated vents may be found in PCT Patent Application Publication No. WO 2013040198.

As described above, the upper housing portion 4132 of the examples shown in FIGS. 16A-16C and 17 may include a vent assembly 3400. The vent assembly 3400 may simply comprise a number of holes through one or more sides of the upper housing portion 4132 that are always open regardless of the patient's breath phase and/or the operation of the blower 4142. In other words, the vent assembly 3400 continuously allows gas to exit the plenum chamber 3200. Alternatively, the vent assembly 3400 may facilitate selective venting, e.g., based on the phase of the patient's breathing and/or the operation of the blower 4142.

The vent assembly 3400 shown in FIGS. 18A-18H provides this selective venting. The vent assembly 3400 may include a base 3404. The base 3404 may be attached to the upper housing portion 4132 permanently or removably (e.g., for replacement or cleaning), or the upper housing portion 4132 may form the base 3404.

The base 3404 may include a vent hole extension 3403 extending from the base 3404. In the depicted examples, two vent hole extensions 3403 are included, one on each lateral side of the base 3404. Each vent hole extension 3403 may include an exterior vent hole surface 3401 that faces towards or is adjacent to atmosphere or faces away from the plenum chamber 3200. Each vent hole extension 3403 may also include an interior vent hole surface 3407 that faces or is adjacent to the plenum chamber 3200. Each vent hole extension 3403 may also include an internal surface 3408. In cross-section, the vent hole extension 3403 may have a generally triangular shape with the exterior vent hole surface 3401, the interior vent hole surface 3407, and the internal surface 3408 forming each side of the triangle. However, it should be understood that each of these surfaces may be flat or curved (convex or concave). Each vent hole extension 3403 may include one or more vent holes 3402 passing between the interior vent hole surface 3407 and the exterior vent hole surface 3401. The vent hole(s) 3402 may follow a linear path or a non-linear path through the vent hole extension 3403. The vent hole(s) 3402 permit gas to pass therethrough to atmosphere during venting, as will be described below.

The vent assembly 3400 may also include a divider 3406 that separating the vent assembly 3400 into two halves. Additionally, a flexible membrane or flap 3405 may be attached to each vent hole extension 3403 that may cover the vent hole(s) 3402 during the inhalation phase to prevent pressurized from being discharged to atmosphere, thereby reducing pressure within the plenum chamber 3200. The flexible membrane 3405 may be relatively thin and may be elastically deformable due to air pressure. The flexible membrane 3405 may be formed from an elastically deformable material such as liquid silicone rubber. The flexible membrane 3405 may be permanently attached to the interior vent hole surface 3407 of the vent hole extension 3403 by an adhesive or by overmolding. The flexible membrane 3405 may be cantilevered to the interior vent hole surface 3407 of the vent hole extension 3403 to allow the flexible membrane 3405 to cover the vent hole(s) 3402.

Additionally, the interior vent hole surface 3407 is angled in the direction of the flow of pressurized gas from the blower 4142 such that it is biased into a closed position. However, by virtue of its cantilevered attachment to the interior vent hole surface 3407 of the vent hole extension 3403, a relatively low magnitude of flow from the patient's exhalation can force the flexible membrane 3405 into a position that opens the vent holes 3402 to atmosphere.

The divider 3406 is shown as a rectangular prism in the depicted examples. However, the divider 3406 may have sloped or curved sides facing the corresponding vent hole extensions 3403.

Also, the flexible membranes 3405 are dimensioned in a longitudinal direction of the divider 3406 in the depicted examples such that they cover substantially all of the passages between the divider and the vent hole extensions 3403. It should be understood that in alternative examples that the flexible membranes 3405 may not run substantially the entire width of the passages in a longitudinal direction of the divider.

Furthermore, the flexible membranes 3405 in the depicted examples are shown as a solid, continuous flap. However, the flexible membranes 3405 may include one or more holes to allow tuning of the amount of flow that they permit.

Also, a flexible printed circuit board and/or wires for providing power to and/or controlling the blower 4142 may pass through the divider 3406.

FIGS. 18F-18H depict operation of the vent assembly 3400. Although none of the other RPT system components are shown, it should be understood that the vent assembly 3400 would be provided to the upper housing portion 4132 as described above in use. In each view, it should be understood that the blower 4142 is above the vent assembly 3400, and when producing the flow of pressurized gas, the flow will travel downward through the vent assembly 3400 to the patient that is on the opposite side of the vent assembly 3400.

FIG. 18F shows the vent assembly 3400 in a neutral state in which there is no air flow. Thus, the flexible membranes 3405 are in an undeformed state. The flexible membranes 3405 are shown covering the vent holes 3402 such that air cannot travel from the plenum chamber 3200 to atmosphere or vice versa. However, the flexible membranes 3405 may be attached to the vent hole extensions 3403 such that in an undeformed state there is a slight gap between the flexible membranes 3405 and the interior vent hole surface 3407 such that a small amount of flow is permitted to travel through the vent holes 3402. Also, the flexible membranes 3405 may be dimensioned such that they do not engage the divider 3406 in an undeformed state, as shown in FIG. 18F, to allow air flow to pass between the divider 3406 and the flexible membranes 3405. Alternatively, the flexible membranes 3405 may be dimensioned such that they do engage the divider 3406 in an undeformed state to prevent air flow from passing between the divider 3406 and the flexible membranes 3405.

FIG. 18G shows the vent assembly 3400 during venting, e.g., during patient exhalation. FIG. 18G shows a vent flow 3409 coming from the direction of the patient to displace and/or deform the flexible membranes 3405 such that the interior vent hole surface 3407 is exposed and the vent holes 3402 are opened or not blocked by the flexible membranes 3405. The vent flow 3409 may be generated by the force of the patient's exhalation. By cantilevering the flexible membrane 3405 from the interior vent hole surface 3407 beyond the vent holes 3402 such that the flexible membrane 3405 overlays the vent holes 3402, the force of the vent flow 3409 will displace and/or deform the flexible membrane 3405 thereby opening the vent holes 3402 such that the vent flow 3409 can exit to atmosphere. The thickness and material of the flexible membrane 3405 may be selected such that the flexible membrane is readily deformable enough to be displaced and/or deformed by the patient's exhalation, even when being opposed by the flow from the blower 4142 travelling in the opposite direction. Also, the flexible membranes 3405 may be dimensioned such that they do not engage the divider 3406 during the exhalation phase, as shown in FIG. 18G, to allow air flow to pass between the divider 3406 and the flexible membranes 3405. Alternatively, the flexible membranes 3405 may be dimensioned such that they do engage the divider 3406 when deformed by exhalation to prevent air flow from passing between the divider 3406 and the flexible membranes 3405 and to ensure the full magnitude of the exhalation force is used to discharge gas, e.g., exhaled $CO_2$, to atmosphere.

FIG. 18H shows the vent assembly 3400 during the inhalation phase. In this view, a pressurized flow of gas 3410 from the blower 4142 pushes the flexible membranes 3405 into a position against the interior vent hole surface that closes off the vent holes 3402 such that the pressurized flow of gas 3410 is directed to the patient for inhalation and not lost to atmosphere. It should also be understood that the flexible membranes 3405 may occupy this position not just during inhalation, but also at any point when the blower 4142 is generating the pressurized flow of gas 3410 and the patient is not exhaling. The material and dimensions (e.g., thickness) of the flexible membrane 3405 may be selected such that the pressurized flow of gas 3410 from the blower 4142 is sufficient to displace and/or deform the flexible membrane 3405 into a position that closes the vent holes 3402 opens the passages between the divider 3406 and the vent hole extensions 3403 to allow the pressurized flow of gas 3410 to reach the patient. Also, the interior vent hole surface 3407 may be angled such that it slopes inwardly or downwardly into the interior of the vent assembly 3400 relative to the direction of the pressurized flow of gas 3410.

The vent assembly 3400 shown in FIGS. 18A-18H is advantageous in that it allows the vent holes 3402 to be opened or closed selectively depending on the phase of the patient's breathing and/or the operation of the blower 4142, and the vent assembly does so passively. In other words, there is no need for a separately actuatable component to open and close vent holes, thereby reducing complexity. Also, vent assembly 3400 of the present technology permits cleaning by simply flushing the vent assembly 3400 with water. The flexible membranes 3405 are sufficiently deformable for water to displace them and allow cleaning throughout. Furthermore, the absence of additional, complex actuating components means that water can readily be flushed through the vent assembly 3400 without damaging it.

The vent assembly 3400 may also include a diffuser material at the exterior vent hole surface 3401 to diffuse the flow of gas passing to atmosphere from the vent hole(s) 3402 to reduce noise and jetting.

Other vent arrangements are also envisioned for application to the present technology. For example, the vent arrangements disclosed in FIGS. 33-35 of U.S. Patent Application Publication No. US 2014/0305431 A1 may also be incorporated into the RPT system of the present technology.

5.3.5 Connection Port

In one form the patient interface 3000 comprises a connection port 3600 for connection to the air circuit 4170.

5.3.6 Forehead Support

In one form, the patient interface 3000 includes a forehead support 3700. The example of the present technology depicted in FIGS. 6A-6C does not include a forehead support. Although a forehead support is not shown in the example depicted in FIGS. 6A-6C, a forehead support may be incorporated into the RPT system, e.g., as a part of the plenum chamber 3200 extending therefrom. The forehead support may be added to enhance stability of the RPT system on the patient's head in use by adding another separate point of contact.

5.3.7 Anti-Asphyxia Valve

In one form, the patient interface 3000 includes an anti-asphyxia valve.

5.3.8 Ports

In one form of the present technology, a patient interface 3000 includes one or more ports that allow access to the volume within the plenum chamber 3200. In one form this allows a clinician to supply supplemental oxygen. In one form, this allows for the direct measurement of a property of gases within the plenum chamber 3200, such as the pressure.

The plenum chamber 3200 may also comprise a port 4134 that is configured to be connected to at least one of a pressure transducer and a supplemental gas source. The pressure transducer, as described in greater detail below, may provide data regarding the conditions within the plenum chamber during operation that can be used by the control systems for controlling the blower 4142. The supplemental gas source may provide the patient with supplemental oxygen, for example, as prescribed by a clinician.

5.4 RPT Device

An RPT device 4000 in accordance with one aspect of the present technology comprises mechanical, pneumatic, and/or electrical components and is configured to execute one or more algorithms. The RPT device 4000 may be configured to generate a flow of air for delivery to a patient's airways, such as to treat one or more of the respiratory conditions described elsewhere in the present document.

In one form, the RPT device 4000 is constructed and arranged to be capable of delivering a flow of air in a range of −20 L/min to +150 L/min while maintaining a positive pressure of at least 6 cmH$_2$O, or at least 10cmH$_2$O, or at least 20 cmH$_2$O. In another form, the RPT device 4000 may be constructed and arranged to be capable of delivering a flow of air in a range of −60 L/min to +80 L/min while maintaining a positive pressure of at least 6 cmH$_2$O, or at least 10cmH$_2$O, or at least 20 cmH$_2$O.

The pneumatic path of the RPT device 4000 may comprise one or more air path items, e.g., an inlet air filter 4112, an inlet muffler 4122, a pressure generator 4140 capable of supplying air at positive pressure (e.g., a blower 4142), an outlet muffler 4124 and one or more transducers 4270, such as pressure sensors 4272 and flow rate sensors 4274.

One or more of the air path items may be located within a removable unitary structure which will be referred to as a pneumatic block 4020. The pneumatic block 4020 may be located within the external housing 4010. In one form a pneumatic block 4020 is supported by, or formed as part of the chassis 4016.

The RPT device 4000 may have an electrical power supply 4210, one or more input devices 4220, a central controller 4230, a therapy device controller 4240, a pressure generator 4140, one or more protection circuits 4250, memory 4260, transducers 4270, data communication interface 4280 and one or more output devices 4290. Electrical components 4200 may be mounted on a single Printed Circuit Board Assembly (PCBA) 4202. In an alternative form, the RPT device 4000 may include more than one PCBA 4202.

5.4.1 RPT Device Mechanical & Pneumatic Components

An RPT device may comprise one or more of the following components in an integral unit. In an alternative form, one or more of the following components may be located as respective separate units. The RPT device may include one or more pneumatic components 4100.

An RPT device in accordance with one form of the present technology may include one or more air filters 4110, and/or one or more mufflers 4120.

5.4.1.1 Pressure Generator

In one form of the present technology, a pressure generator 4140 for producing a flow, or a supply, of air at positive pressure is a controllable blower 4142. For example the blower 4142 may include a brushless DC motor 4145 with one or more impellers housed in a volute. In another example, blower 4142 may include a brushless DC motor 4145 with one or more impellers and stator vanes, and housed in a casing. The blower may be capable of delivering a supply of air, for example at a rate of up to about 120 litres/minute, at a positive pressure in a range from about 4 cmH$_2$O to about 20 cmH$_2$O, or in other forms up to about 30 cmH$_2$O. The blower may be as described in any one of the following patents or patent applications the contents of which are incorporated herein by reference in their entirety: U.S. Pat. Nos. 7,866,944; 8,638,014; 8,636,479; and PCT Patent Application Publication No. WO 2013/020167.

The pressure generator 4140 is under the control of the therapy device controller 4240.

In other forms, a pressure generator 4140 may be a piston-driven pump, a pressure regulator connected to a high pressure source (e.g. compressed air reservoir), or a bellows.

5.4.1.1.1 Blower 4142 of the Present Technology

The blower 4142 of the present technology may include multiple sets of stages of small diameter impellers in parallel flow paths. The parallel stage arrangement may allow the blower 4142 to generate sufficient flow rates, while reducing the size of the blower 4142 and reducing its generation of noise. As can be seen in FIGS. 7A-7F, the exemplary blower 4142 includes two sets of a first compression stage 4136 and a second compression stage 4137, wherein each set is arranged in parallel on each side of a motor 4145. In other words, the blower 4142 may include two pairs of stages in a substantially mirrored configuration relative to an axial direction of the motor 4145. While the exemplary blower 4142 is shown with two stages arranged in series on each side, it is envisioned that there could be only one stage on each side of the blower 4142. Alternatively, there could be more than two compression stages provided to each side of the blower. In still further alternatives, there could be asymmetric compression stages, e.g., one stage on one side of the blower 4142 and two stages on the other side of the blower 4142. The stages themselves may also be asymmetric in that the stator and impeller of any given stage may be distinct from those of another stage.

The blower 4142 may be used in a respiratory pressure therapy (RPT) system and may be configured to generate a flow of air at a therapeutic pressure of at least 6 cmH$_2$O above ambient air pressure. The exemplary blower 4142 and RPT systems disclosed in FIGS. 6A to 14 may be used to treat sleep disordered breathing conditions such as sleep apnea and may also be used to treat other respiratory issues not necessarily related to sleep such as COPD. The blower 4142 may comprise a motor 4145 having a first end and a second end (shown in a simplified outline form). The blower 4142 may also have a generally cylindrical shape. Also, a first impeller 4150 and a second impeller 4160 may be arranged in series on the shaft 4146 such that both first impellers 4150 and both second impellers 4160 are driven simultaneously by the motor 4145.

As each set of impellers at either end of the motor 4145 are configured to generate a flow of gas in opposing directions to each other, while being driven by the same shaft, each opposing impeller 4150 and 4160 may comprise a mirrored geometry. Thus, for example, impellers 4150, 4160 located at a first end of the shaft 4146 of the motor 4145 may each comprise forward swept blades and impellers 4150, 4160 located at the second or opposite end of the shaft 4146 of the motor 4145 may have a different (mirrored) geometry. In other words, since both ends of the shaft 4146 will be rotating in the same direction when the motor 4145 is operating, the impellers 4150, 4160 at each respective end of the shaft may be swept forward relative to the shaft's 4146 rotational direction so that both sides of the blower 4142 generate a flow of gas in the same direction.

The blower 4142 may also include a first stator 4180 corresponding to each of the first end of the motor 4145 and the second end of the motor 4145. The first stator 4180 may be positioned downstream of the first impeller 4150 and upstream of the second impeller 4160 along the flow of air generated by the blower in use. The blower 4142 may also include a second stator 4190 corresponding to each of the first end of the motor 4145 and the second end of the motor 4145, the second stator 4190 positioned downstream of the second impeller 4160 along the flow of air generated by the blower 4142 in use.

The blower 4142 may also include an end cap 4144 that is shaped and dimensioned to at least partially enclose each first impeller 4150. Each end cap 4144 may also at least partially define a blower inlet 4143 on each side of the blower 4142. The blower 4142 may also include a blower outlet 4141 positioned downstream of each second stator, such as at or towards a centre of the blower 4142 in the axial direction. A flow path 4138 for the flow of air passing from each blower inlet 4143, past each first impeller 4150, through each first stator 4180, past each second impeller 4160, through each second stator 4190, and out each blower outlet 4141 may be defined through the blower 4142. The blower outlet 4141 may extend annularly around the entirety or a portion of the circumference of the blower 4142.

FIG. 7A depicts an example of the blower 4142 according to the present technology separated from the housing portions 4132, 4133. For example, the mounting rails 4183 on the exterior of the first stator housing 4184 of the first stator 4180 are visible. Also, the blower outlet 4141 is visible, as well as a portion of the second stator 4190 that leads to the blower outlet 4141. FIG. 7A also depicts other components of the blower 4142, including the end cap 4144, which defines the blower inlet 4143 and partially encloses the first impeller 4150. As can be seen in FIG. 7A, the blower's 4142 structure is mirrored or symmetrical such that each half of the blower 4142 may include identical (mirrored) components.

Thus, the blower 4142 may comprise two sets of inlets and outlets. That is, a set of inlets 4143 (e.g. two inlets) located at or toward opposing ends of the blower 4142, and a set of outlets 4141 (e.g. two outlets) located at or towards a centre of the blower 4142, with respect to an axial direction of the blower 4142.

FIG. 7B depicts a similar view of the exemplary blower 4142 to FIG. 7A, but the end caps 4144 are removed to depict the first impellers 4150. Additionally, a portion of the first stator vanes 4186, 4187 of the first stator 4180 are also visible. As will be described in greater detail below, during the first compression stage the flow of gas generated by spinning the first impeller 4150 passes within the volume defined by the end cap 4144 and then through the first stator vanes 4186, 4187 to reach the second impeller 4160 for the second stage of compression.

FIG. 7C depicts another view of the exemplary blower 4142 with the end caps 4144 and the first impellers 4150 such that the first stator upper shroud 4182A of the first stator 4180 is visible. Additionally, a larger portion of the first stator vanes 4186, 4187 are visible as well. During the first stage of compression 4136, the flow of gas generated by spinning the first impeller 4150 passes under the first stator upper shroud 4182A and between the first stator vanes 4186, 4187 before reaching the second impeller 4160 for the second stage of compression 4137.

FIG. 7D depicts another view of the exemplary blower 4142 with the first stator 4180 removed. In this view, the second impeller 4160 and the second stator 4190, including the second stator vanes 4191, are more fully visible. The features of these individual components will be described in greater detail below.

FIG. 7E depicts a cross-sectional view of the exemplary blower 4142, as shown in FIG. 7A, in which the cross-section is cut along a plane containing the axis of rotation of the motor 4145. In this view, it is possible to see portions of the flow path that gas follows from the blower inlet 4143 through both stages of compression and out the blower outlet 4141.

FIG. 7F depicts an exploded view of the exemplary blower 4142.

5.4.1.1.1.1 Compression Stages 4136, 4137

In one exemplary configuration, each pair of compression stages 4136, 4137 corresponding to two impeller-stator pairs, could deliver up to approximately 40 L/min of flow with the motor 4145 operating at, e.g., 65,000 rpm. Thus, combining the pairs of compression stages 4136, 4137 in parallel on each side of the blower 4142 would be capable of delivering approximately 80 L/min at a therapeutic pressure of approximately 10 or 15 cmH$_2$O. In this example, the motor 4145 would have an outer diameter of 13 mm and a length of 37 mm and the blower 4142 would have an outer diameter of 18 mm and a length of 46 mm. It is also envisioned that additional impellers could be added in series to an individual compression stage to generate even higher pressures.

5.4.1.1.1.2 Motor 4145

The blower 4142 may include a motor 4145 in the form of a single brushless DC motor. The motor 4145 may include a shaft 4146 protruding from each end in an axial direction to drive the corresponding impellers on each side. Since the ends of the shaft 4146 would spin in same direction during operation of the blower 4142, it should be understood that the shapes of the impellers and stators may be mirrored but otherwise identical on opposite sides of the blower 4142. The motor 4145 of the present technology may be capable of operating from a minimum of approximately 5,000 rpm or approximately 10,000 rpm to a maximum of approximately 50,000 rpm to approximately 80,000 rpm, generating max torque from approximately 0.5 mN-m to approximately 1 mN-m, and generating max power of approximately 3 W to 6 W. While the depicted example includes one motor to drive both sets of compression stages 4136, 4137 on each side of the blower 4142, it is envisioned that the blower 4142 could include two motors 4145 in which each motor drives a single set of the compression stages 4136, 4137.

5.4.1.1.1.3 Impellers 4150, 4160

An exemplary first impeller 4150 is depicted in FIGS. 8A-8L, but it should be understood that each second impeller 4160 may be identical to the corresponding first impeller 4150. Alternatively, each first impeller 4150 and each second impeller 4160 may be designed distinctively to optimize the flow rate and pressure generated based on their relative positions in the flow path 4138. Regardless of whether they are designed differently or identically, each first impeller 4150 and each second impeller 4160 may include an impeller hub 4153, impeller vanes 4151 extending radially from the impeller hub 4153, and an impeller shroud 4152. The impeller hub 4153 is the portion of the impeller 4150 that joins the impeller 4150 to the corresponding end of the shaft 4146.

The impeller vanes 4151 direct the flow of gas radially outward during rotation of the impeller 4150. The impeller vanes 4151 may each have a first impeller vane portion 4154 that extends only in a radial direction and a second impeller vane portion 4155 that extends in a radial, tangential and axial direction (or in a radial and axial direction only). The first impeller vane portion 4154 may have a constant cross-section and the first impeller vane portion 4154 may be positioned is radially inward relative to the second impeller vane portion 4155. The second impeller vane portion 4155 may have a variable cross-section and may be positioned radially outward relative to the first impeller vane portion 4154. The constant cross-section of the first impeller vane portion 4154 may also be thinner than the variable cross-section of the second impeller vane portion 4155 at any point. The variable cross-section of the second impeller vane portion 4155 may increase in thickness radially outward from the first impeller vane portion 4154 and then decrease in thickness further radially outward.

The impeller vanes 4151 of each first impeller 4150 and each second impeller 4160 may be swept or curved forward relative to the direction of rotation 4139 during operation. Alternatively, the impeller vanes 4151 of each first impeller 4150 and each second impeller 4160 may be swept or curved backward relative to the direction of rotation 4139 during operation.

The impeller shroud 4152 prevents the incoming flow of gas from traveling past the impeller vanes 4151 in an axial direction so that the impeller vanes 4151 redirect the flow of gas radially, while spinning the gas tangentially. Each impeller shroud 4152 may include a first impeller shroud portion 4156 that extends only in a radial direction and a second impeller shroud portion 4157 that extends in a radial and axial direction. The impeller shroud 4152 may also include cutouts to allow moulding of the impellers in the line of draw.

The first impeller vane portion 4154 of the impeller 4150 shown in FIGS. 8A to 8M may be straight to maximise its cross-sectional area, thereby minimising entry loss at the blower inlet 4143. Indeed, as can be seen in FIG. 7A, the first impeller vane portion 4154 is exposed through the blower inlet 4143 to draw in air. Furthermore, the forward curvature of the second impeller vane portion 4155 may create pressure through relatively high tangential velocities. Additionally, axial development of the flow out of the impeller 4150 in the axial direction may encourage the flow to travel in the axial direction, which may beneficially add axial velocity that the stators 4180, 4190 can convert into additional pressure. The concept of additional axial development may be understood to mean that the more time that the airflow spends where work is being done on it by the impeller 4150 (e.g., via centrifugal effects), the more the stators 4180, 4190 can convert the increased velocity of the airflow into pressure. Additional axial development also means more time that the air flow spends where work is being done on it by the impeller 4150 (hence generating pressure via centrifugal effects).

FIGS. 12A and 12B depict another example of the first impeller 4150 according to the present technology. This first impeller 4150 is similar to the first impeller 4150 described above in that it includes the same basic structural components, e.g., first impeller vanes 4151, the first impeller shroud 4152, and the first impeller hub 4153. However, the first impeller vanes 4151 and the first impeller shroud 4152 are shaped differently in the example of FIGS. 12A and 12B. For example, the cross-section of the first impeller vanes 4151 does not change in thickness in a radial direction between the first impeller vane portions 4154 and the second impeller vane portions 4155. Also, the curvature of the second impeller vane portions 4155 is more abrupt in the example of FIGS. 12A and 12B. Furthermore, the second impeller vane portions 4155 do not extend in an axial direction in the example of FIGS. 12A and 12B. Similarly, the first impeller shroud 4152 does not extend from the first impeller hub 4153 in an axial direction in the example of FIGS. 12A and 12B. In other words, the first impeller shroud 4152 is generally flat, at least on the side opposite the first impeller vanes 4151. The impeller vanes 4151 of the impeller 4150 of FIGS. 12A and 12B may be swept or curved forward relative to the direction of rotation 4139 during operation. Alternatively, the impeller vanes 4151 of the impeller 4150 of FIGS. 12A and 12B may be swept or curved backward relative to the direction of rotation 4139 during operation.

The exemplary first impeller 4150 depicted in FIGS. 13A and 13B is similar to the first impeller 4150 depicted in FIGS. 12A and 12B, except for the shape of the first impeller vanes 4151. In the exemplary first impeller 4150 of FIGS. 13A and 13B the first impeller vanes 4151 have a continuous and less abrupt curvature in the radial direction. However, like the first impeller 4150 of FIGS. 12A and 12B, the first impeller 4150 of FIGS. 13A and 13B, the thickness of the cross-section of the first impeller vanes 4151 is consistent in the radial direction. The impeller vanes 4151 of the impeller 4150 of FIGS. 13A and 13B may be swept or curved forward relative to the direction of rotation 4139 during operation. Alternatively, the impeller vanes 4151 of the impeller 4150 of FIGS. 13A and 13B may be swept or curved backward relative to the direction of rotation 4139 during operation. As described above, either of the first impellers 4150 depicted in FIGS. 12A and 12B or FIGS. 13A and 13B could be used in both the first compression stage 4136 and the second compression stage 4137. In other words, both compression stages 4136, 4137 include identical impellers for the first impeller 4150 and the second impeller 4160. Alternatively, different impeller designs may be used in each of the first compression stage 4136 and the second compression stage 4137.

The first impeller vane portion 4154 of the impeller 4150 shown in FIGS. 12A and 12B may be straight to maximise its cross-sectional area, thereby minimising entry loss at the blower inlet 4143. Indeed, as can be seen in FIG. 7A, the first impeller vane portion 4154 is exposed through the blower inlet 4143 to draw in air. Furthermore, the forward curvature of the second impeller vane portion 4155 may create pressure through relatively high tangential velocities.

5.4.1.1.1.4 Impeller 500

Examples of impellers according to the present technology are shown in FIGS. 19A-19EE. The impeller may be suitable for use in a centrifugal blower, such as those described elsewhere in the present specification.

An impeller 500 may comprise one or more of:
a set of impeller blades 510, each impeller blade 510 comprising a leading edge 511 and a trailing edge 512;
a first shroud and/or a second shroud, such as a top shroud 520 and/or a bottom shroud 525, at least partly defining a flow passage 540 through the impeller;
a hub 530 for coupling the impeller to a motor, the hub 530 may be retained by an interference fit to a rotor or motor shaft of the motor for example, however any number of other known retention mechanisms may be suitable.

Where the impeller 500 comprises a first shroud and a second shroud, the first and second shrouds may be arranged such that an axial distance therebetween may generally decrease towards an outer portion of the impeller in the radial direction.

FIGS. 19A to 19N illustrate an impeller 500 according to one example of the present technology. As illustrated, the impeller 500 includes a plurality of impeller blades 510 located between and connected to the first or top shroud 520 and the second or bottom shroud 525. In the illustrated example, the bottom shroud 525 extends to the hub 530 adapted to receive the rotor of the motor.

In the illustrated example, the top shroud 520 is substantially non-planar. For example, the top shroud 520 may taper in the radial direction with respect to the axial direction of the impeller, e.g., the top shroud 520 may comprise a frusto-conical shape. The top shroud 520 includes an outer edge defining a diameter D of the top shroud and an inner edge defining a center opening which provides an impeller inlet 522. An impeller inlet wall 521 extends along the inner edge to define a periphery of the impeller inlet 522. The free end portion of the inlet wall 521 provides a leading edge 523 of the impeller inlet 522. In this arrangement, the top shroud 520 extends to an outer periphery of the impeller, thus the diameter D of the top shroud is the same as the diameter of the impeller. However in other arrangements, the top shroud 520 may not extend to the outer periphery of the impeller, for example only covering a part of the impeller blades.

In the illustrated example, the bottom shroud 525 is substantially planar. As illustrated, the outer edge of the bottom shroud 525 defines a diameter that is substantially similar, e.g., the same, to the diameter D defined by the outer edge of the top shroud 520. In an example, the diameter D of the impeller is less than about 50 mm.

The top and bottom shrouds 520, 525 cooperate to define a flow passage 540 therebetween through the impeller. The flow passage 540 extends from the impeller inlet 522 at an inner portion of the impeller to an impeller outlet 524 at an outer portion of the impeller. The flow passage 540 may include a plurality of channels, each channel defined at least partly by the top and bottom shrouds 520, 525 and impeller blades 510.

In the illustrated example, the flow passage 540 defined between the top and bottom shrouds 520, 525 is structured to narrow (in a normal direction to the direction of the airflow) from the impeller inlet 522 to the impeller outlet 524, i.e., the spacing or distance between the top and bottom shrouds 520, 525 lessens or tapers from the impeller inlet to the impeller outlet.

That is, the top and bottom shrouds 520, 525 are configured such that the flow passage is narrower in the axial direction at the outer portion of the impeller than at the inner portion of the impeller, i.e., an axial distance between the top and bottom shrouds 520, 525 may generally decrease towards the outer portion of the impeller in the radial direction. For example, FIG. 19B shows exemplary axial distances d1 and d2 between the top and bottom shrouds 520, 525, with d1 along an inner portion of the impeller larger than d2 along an outer portion of the impeller and the axial distance gradually decreasing from d1 to d2 in the radial direction. Additionally, the top and bottom shrouds 520, 525 are configured such that the axial distance between them at the outlet of the impeller (i.e., d2) is smaller than the radial dimension of the inlet.

Thus, an impeller according to an aspect of the present technology may comprise a flow passage 540 comprising a plurality of channels, each channel configured with a decreasing height along a direction of the air flow therethrough.

5.4.1.1.1.4.1 Impeller Inlet

An impeller according to the present technology may comprise a relatively large impeller inlet size as a proportion of the impeller diameter D. In one form, the impeller inlet 522 may be defined by a periphery of the top shroud 520, such as in FIG. 19B, where the inlet wall 521 of the top shroud 520 is shown in the cross section.

In general, it may be a disadvantage to increase a size of the impeller inlet in a centrifugal blower while maintaining other dimensions (e.g., impeller diameter), as such an increase may decrease an effective diameter of the impeller in which centrifugal energy may be imparted to the air flowing through the blower. In other words, enlargement of an impeller inlet may result in a configuration wherein insufficient pressure is generated by the blower.

However, for an application such as in RPT devices, where a small size of the device is desirable for aesthetic reasons, convenient bedside placement of the RPT device and portability, a designer may wish to reduce a size of the impeller. However, as an impeller diameter is reduced, a velocity of the air flow through the impeller is increased, adversely affecting noise and efficiency of the impeller, for example caused by changes to an aerodynamic behaviour due to the increase in air velocity.

As described elsewhere, an RPT device may be relatively unique in that it is preferably small and quiet for bedside/nocturnal/sleep-time use, while requiring generation of sufficient pressures and flow rates for respiratory therapy. For use in small, possibly portable, RPT devices, it was found that a decrease in impeller diameter may be accompanied by a relative increase in the impeller inlet diameter.

In one form, the impeller of a diameter D of less than 50 mm may comprise an impeller inlet 522, wherein a diameter ($d_{inlet}$ as shown in FIG. 19A) of the impeller inlet 522 is at least 50% of the diameter D of the impeller. In one example, the impeller may comprise a diameter D of 40 mm with an impeller inlet diameter $d_{inlet}$ of 20 mm, 22 mm or 24 mm According to another aspect of the present technology, the impeller inlet wall 521, or a periphery of the impeller inlet 522, may comprise a relatively large radius to improve overall impeller and/or blower performance. An increased radius at a portion facing the incoming air flow into the impeller may advantageously lead to improved efficiency, as the air flow remains attached to the inlet wall 521.

In one form, a leading edge of the periphery of the impeller inlet 522, e.g., the leading edge 523 at the free end portion of the inlet wall 521 of the top shroud 520 (as best shown in FIG. 19B), comprises a cross sectional shape with a radius of at least 0.5 mm. In another form, a radius of the leading edge of the first or top shroud 520 is greater than 70% of the maximum thickness of the body of the first shroud 520, such as greater than 85%, 100% or 115%. In another form, a radius of the leading edge 523 of the first or top shroud 520 is greater than the maximum thickness of a body of the first shroud 520. In another form, a leading edge of the first or top shroud 520 comprises a cross sectional shape with a radius of at least 1% of the diameter D of the impeller. In use, an air flow entering the impeller at the impeller inlet 522 is discouraged from detachment at or around the radius, e.g., to reduce noise and improve efficiency.

5.4.1.1.1.4.2 Impeller Blades

The impeller 500 may comprise a plurality of impeller blades 510. In the illustrated example, the impeller includes 11 blades 510. However, it should be appreciated that the impeller may include other suitable numbers of blades, e.g., 3 or more blades, e.g., 5-20 blades, e.g., 7 blades, 11 blades, 13 blades.

Each impeller blade 510 extends from the hub 530 towards the outer edge of the impeller. Each impeller blade may be connected to the top and bottom shrouds 520, 525. Each impeller blade comprises a leading edge 511 and a trailing edge 512. It should be noted that the terms 'leading edge' and 'trailing edge' are to be understood akin to its usage in aeronautics, referring to a portions of a wing, rather than a narrow geometric sense of an 'edge'.

For example, a 'leading edge' may refer to a part of the impeller blade that generally first contacts the air coming into the impeller. Similarly, a 'trailing edge' may refer to a part of the impeller blade that generally last contacts the air as it leaves the impeller.

In the illustrated example, the impeller blades 510 are sandwiched between the top and bottom shrouds 520, 525. As illustrated, each blade 510 is overlapped by the top shroud 520 such that a first edge 515 along an outer portion of the blade is in contact with the top shroud 520 and the leading edge 511 along an inner portion of the blade is exposed through the impeller inlet 522, i.e., leading edge 511 extends between the inlet wall 521 and the hub 530 defining the inlet 522 into the impeller. Each blade 510 is overlapped by the bottom shroud 525 such that a second edge 517 is in contact with the bottom shroud 525 and hub 530 along its entire length. The trailing edge 512 is exposed through the impeller outlet 524 between the outer ends of the top and bottom shrouds 520, 525.

In the illustrated example, each blade 510 extends to the outer edges of the top and bottom shrouds 520, 525, e.g., the blades 510 do not extend beyond the top and bottom shrouds 520, 525. In alternative examples, the blades 510 may extend beyond or extend short of the outer edges of the top and bottom shrouds 520, 525.

According to one aspect of the present technology, the leading edge 511 and/or the trailing edge 512 of an impeller blade 510 may be very thin, such that turbulence and noise is reduced at the inlet and outlet of the impeller. In an example, the thickness of the leading edge 511 and/or the trailing edge 512 of an impeller blade 510 may be less than about 0.2 mm, e.g., less than about 0.1 mm, such as measured at its thinnest portion, or measured at its outermost portion (i.e., most downstream portion). Furthermore, uniquely to RPT devices, some impeller designs may be such that a seemingly small reduction in a size of the leading (and/or trailing) edge may have a positive effect on the air flow of the impeller and efficiency of the RPT device.

In an example, the cross-sectional thickness of each blade 510 may be variable or tapered, e.g., along at least a portion of its length in plan view. For example, as shown in FIGS. 19K-19N, an outer portion of each blade 510 may include a cross-sectional thickness that tapers towards the trailing edge 512.

Also, as shown in FIGS. 19K-19N, each blade 510 may be curved and/or provide curved exterior surfaces, e.g., along at least a portion of its length in plan view. For example, as shown in FIGS. 19K-19N, an outer portion of each blade 510 may provide curved surfaces 519 along its length towards the trailing edge 512, e.g., to provide a smooth air flow passage to reduce turbulence and hence noise.

Further, as shown in FIGS. 19K-19N, the flow passage defined between adjacent blades 510 is structured to enlarge, e.g., along at least a portion of its length in plan view. For example, as shown in FIGS. 19K-19N, the flow passage defined between adjacent blades 510 is structured to enlarge towards the trailing edges 512, e.g., to increase pressure.

An impeller blade 510 may be inclined, as shown in FIG. 19C, 19P or the cross sections shown in FIGS. 19K-19N. For example, the leading edge 511 of each blade 510 may be inclined, e.g., by an angle greater than 45 degrees, with respect to an axis of the hub 530 or motor.

In the example of FIGS. 19A-19N, the trailing edge 512 extends substantially parallel to an axis of the hub 530.

In some forms, as shown in FIGS. 19O-19S, the impeller blade 510 may comprise one or more serrations, e.g., the leading edge 511 and/or the trailing edge 512 may comprise one or more serrations arranged along the leading edge 511 and/or the trailing edge 512. Some examples of potentially suitable arrangements of leading edge and/or trailing edge serrations may be found on PCT Patent Application Publication No. WO 2016/201516, the contents of which is incorporated herein by reference in its entirety.

5.4.1.1.1.4.3 Impeller Construction

Many prior art impellers, particularly in the field of respiratory pressure therapy devices, have been manufactured by injection moulding a polymer material. Typical reasons may have included (but not limited to):

- low cost per part, particularly as volume produced increases;
- smooth surface finish from injection moulding, which may minimise any turbulence generated;
- high reproducibility of moulded parts, ensuring consistency and quality control; and
- low density (and relatively high stiffness and strength) of plastic used, helping to minimise mass and rotational inertia, such that rapid acceleration and deceleration may be more easily achievable.

As a consequence of using injection moulding, particular impeller geometries may have been either extremely difficult to achieve, or simply not possible using injection moulding only. For example, an impeller employing curved and swept blades, as well as top and bottom shrouds, may be extremely difficult to manufacture using an injection moulding process.

That is, once the component had been moulded, it could not be extracted from the moulding tool, as the tool and the component would now be intertwined.

In another example, an injection moulded plastic component may require a minimum wall thickness, such that the molten plastic being injected may be able to flow sufficiently within the mould without requiring excessive pressures.

In some examples, an impeller comprising one or more of the aspects described herein may be manufactured by employing alternative manufacturing methods or constructions, while overcoming some of the disadvantages previously associated with such methods.

Additive Manufacturing

In one aspect, an impeller according to the present technology may be produced by an additive technique, sometimes referred to as "three-dimensional (3D) printing", potentially using a metallic material such as titanium, aluminium or stainless steel.

In many applications, even in some instances of RPT devices, a metallic impeller may have a disadvantage over a polymer impeller due to the increased rotational inertia. As alluded to earlier, a higher rotational inertia of an impeller may require an increased capability from a motor driving the impeller, as the requisite torque to accelerate or decelerate the impeller is increased. In turn, the motor may increase in size, and requirements for the power supply and/or a battery may accordingly be increased.

However, for a relatively small impeller, some of these problems may be ameliorated, whereby use of a metallic material becomes more feasible. As a diameter of the impeller decreases, the corresponding rotational inertia decreases as a power of 4 of a decrease of diameter, as: $I \approx mr^2$, where I refers to rotational inertia, m to mass of the impeller and r is the radius of the impeller.

Thus, advantageously, it was found that for the present application and size, additive manufacturing techniques using a metallic material may be particularly suitable such that high-efficiency geometry such as those described herein may be achieved.

In some instances, a material (e.g., metallic material) with the same/similar coefficient of expansion as a rotor (e.g., motor shaft) may be chosen (e.g., the shaft and the impeller may comprise the same metal or metallic material), such that if the impeller is press fit onto the rotor, any thermal expansion would occur uniformly between the two joined, rotating components. This may help to preserve integrity of an interference fit despite variations in temperature, which may vary more within a motor than for example in ambient air.

Multi-Part Construction

According to one aspect of the present technology, such as shown in FIGS. 19T-19EE, an impeller 500 may comprise multiple portions.

In some forms, one portion may comprise a different material to another portion. For instance, a first portion may comprise a deformable, resilient material and a second portion may comprise a rigid material. In an example, the rigid material may be a plastic material, and the resilient material may be an elastomeric material such as a silicone material.

In the example shown in FIGS. 19Y-19EE, a first moulded part or portion, i.e., a first impeller portion 500-1, may be structured and arranged to be coupled to a second moulded part or portion, i.e., second impeller portion 500-2, to produce the impeller 500. The first impeller portion 500-1 may comprise a deformable, resilient material (e.g., an elastomeric material such as silicone) that may be coupled with the second impeller portion 500-2 comprising a rigid material (e.g., rigid plastic). For example, a manufacturing process may first produce (e.g., mould) the second impeller portion 500-2, onto which the first impeller portion 500-1 may be overmoulded. Other forms of coupling, such as chemical bonding or mechanical bonding, may be suitable that are not overmoulded.

As illustrated, the first impeller portion 500-1 comprises the plurality of impeller blades 510, a portion of the top shroud 520 (i.e., an inner or first portion 520-1 of the top shroud which comprises the inlet wall 521 defining the periphery of the impeller inlet 522), and a portion of the bottom shroud 525 (i.e., an outer or first portion 525-1 of the bottom shroud). The second impeller portion 500-2 comprises a portion of the top shroud 520 (i.e., an outer or second portion 520-2 of the top shroud), the hub 530 structured for coupling to the rotor, a portion of the bottom shroud 525 (i.e., an inner or second portion 525-2 of the bottom shroud), and inner blade portions 513. The inner blade portions 513 are adapted to be received in corresponding openings 514 provided within the impeller blades 510, e.g., to add rigidity to the impeller blades 510.

When the first impeller portion 500-1 is overmoulded to the second impeller portion 500-2 to produce the impeller 500, the inner portion 520-1 and the outer portion 520-2 cooperate to form the top shroud 520, the outer portion 525-1 and the inner portion 525-2 cooperate to form the bottom shroud 525, and the inner blade portions 513 add interior rigidity to the impeller blades 510, i.e., inner blade portions 513 add a rigid material to the impeller blades 510. In such arrangement, the impeller blades 510 and the leading and trailing edges 511, 512 thereof comprise an elastomer material (e.g., silicone), and the hub 530 comprises a rigid material for coupling to the rotor.

By such a construction, an impeller may be produced with the desired, advantageous aerodynamic features described herein, which can be injection moulded. That is, using such a construction, the manufacturer may be able to withdraw a 'core' of the injecting moulding tool, as the first impeller portion 500-1 (e.g., comprising silicone) would be able to resiliently deform to allow removal of the injection moulding tool. Further advantageously, such a material (e.g., silicone) of the first impeller portion 500-1 may allow manufacture of thinner wall sections than plastic, thus enabling manufacture for example of the thin impeller blade leading edge 511 and/or trailing edge 512 described above.

Also, a strategic use of such a deformable, resilient material, rather than construction of an impeller entirely from a deformable, resilient material, may help to manufacture an impeller wherein an overall structural integrity is sufficient for durability as well as limiting deformation in operation.

In other forms, an impeller may comprise multiple portions, each not necessarily comprising different materials to each other.

In the example shown in FIGS. 19T-19X, the first impeller portion 500-1 and the second impeller portion 500-2 may be separately moulded and assembled or fastened together. In an example, the first and second portions may each comprise a rigid material (e.g., rigid plastic, such as PEEK, also known as polyetheretherketone). In another example, the first portion may comprise a deformable, resilient material (e.g., an elastomeric material such as silicone) and the second portion may comprise a rigid material (e.g., rigid plastic). For example, the first portion 500-1 (i.e., the first moulded part or portion) may comprise the top shroud 520, the impeller blades 510, and a first fastening portion 550.

The second portion 500-2 (i.e., the second moulded part or portion) may comprise the hub 530, the bottom shroud 525, and a second fastening portion 555. The first impeller portion 500-1 and the second impeller portion 500-2 are fastened together by assembling the first fastening portion 550 to the second fastening portion 555.

In the illustrated example, the first fastening portion 550 includes a hub portion 550-1 and radially extending projections 550-2 spaced about the perimeter of the hub portion 550-1 (e.g., see FIG. 19W). The second fastening portion 555 includes an annular slot 555-1 about the hub 530 adapted to receive the hub portion 550-1 of the first fastening portion 550 when assembled, and the second fastening portion 555 includes radially extending slots 555-2 adapted to receive respective projections 550-2 of the first fastening portion 550 when assembled, e.g., to prevent relative rotation. However, it should be appreciated that the first and second fastening portions 550, 555 may comprise other fastening configurations to fasten, interlock, or otherwise interface the first and second impeller portions.

The two portions 500-1 and 500-2 may be fastened or secured together to produce the impeller 500, such as by snap fit, gluing, welding or any number of other suitable methods. Still further, in some forms, the two portions 500-1 and 500-2 may be arranged such that coupling the assembled impeller 500 onto the motor (e.g., via motor shaft) further strengthens the bonding between the portions of the impeller 500. For example, when the hub 530 of impeller 500 is coupled to the rotor or motor shaft (e.g., by a press fit), the fastening (e.g., snap-fit) between the two portions 500-1 and 500-2 may be assisted and tightened by such hub coupling, e.g., the snap-fit fastening may be tightened by the press-fit coupling of the hub to the rotor.

It will of course be understood that this would not be limited to impellers consisting of two portions, however any number of portions may be assembled together to produce an impeller.

5.4.1.1.1.4.4 Exemplary Blower

FIG. 19FF shows a blower 600 for an RPT device including impellers 500 according to one aspect of the present technology. In the illustrated example, the blower 600 includes a two-stage design structured and configured for producing a flow, or a supply, of air at positive pressure, e.g., in the range of 4-30 cmH$_2$O. In an example, the RPT device is configured to deliver the flow of air from the outlet for delivery to the patient at a pressure between 4-30 cmH$_2$O at an overall sound power level of less than 50 dB(A) thereby reducing any disturbance to a quality of sleep for the patient. However, in alternative examples, the blower may include a single stage design, a three stage design, or four or more stage designs.

As shown, the blower 600 includes a housing 610 including an axial air inlet (blower inlet) 612 and axial air outlet (blower outlet) 614 between which are located two stages with corresponding impellers 500, i.e., a first impeller 500 positioned on one side of the motor 620 and a second impeller 500 positioned on the other side of the motor 620. The motor 620 includes a rotor 625 to which the impellers 500 are coupled. The impellers 500 are configured to be rotated by the rotor 625 to deliver a flow of air from the inlet 612 toward the outlet 614. However, other suitable impeller arrangements are possible. Each impeller 500 may be followed by a set of stator vanes structured and configured to direct the air flow to the next stage or outlet.

In an example, the housing 610 may comprise a plurality of housing portions (e.g., first housing part including inlet 612, second housing part including outlet 614, and intermediate housing parts (e.g., stationary components providing stator vanes to direct air flow) that are connected to one another (e.g., welded) to a form a substantially sealed structure.

Further examples and details of the blower are described in PCT Patent Application Publication No. WO 2013/020167, which is incorporated herein by reference in its entirety.

According to one aspect of the present technology, a portion of the housing 610 adjacent each impeller 500 may include a radius that substantially corresponds to the radius at the leading edge 523 of the impeller inlet wall 521 of the impeller 500. For example, as best shown on FIG. 19GG, a portion of the housing 610 adjacent the perimeter of the blower inlet 612 includes a generally curved surface, e.g., concave surface 615, spaced from and adjacent the generally curved surface, e.g., convex surface 527, provided at the leading edge 523 of the impeller inlet wall 521. In an example, such generally concave surface 615 of the housing 610 includes a radius that substantially corresponds to a radius of the generally convex surface 527 provided at the leading edge 523 of the impeller inlet wall 521.

The substantially corresponding radiuses, the configuration of the curved channel 650 formed between the surfaces 615, 527 of the housing 610 and the impeller 500, and such curved channel 650 terminating at a point where the tangent would point generally downwards (i.e., towards the impeller as approximated by the short arrow A1 in FIG. 19GG) helps re-circulated flow (indicated by the long arrow A2 in FIG. 19GG) smoothly enter the impeller inlet 522. That is, the curved channel 650 formed by corresponding curved surfaces 615, 527 of the housing 610 and the impeller 500 smoothly directs re-circulated flow into the impeller inlet 522.

5.4.1.1.1.5 Stators 4180, 4190

Like the impellers 4150, 4160, the blower 4142 may include multiple stators that correspond to each impeller. FIGS. 9A-9F and FIGS. 10A-10E depict features of an example first stator 4180 that corresponds to the first impeller 4150, which together form the first compression stage 4136. The first stator 4180 may include a plurality of first stator vanes 4187, 4188 to direct the flow of air from the first impeller 4150 to a first stator opening 4186 in a radial direction, reduce the velocity of the flow of air from the first impeller 4150, and increase the pressure of the flow of air from the first impeller 4150.

The first stator vanes 4187, 4188 may be distinguished as extended first stator vanes 4187 and short first stator vanes 4188. The extended first stator vanes 4187 extend further radially inward than the short first stator vanes 4188, as can be seen in FIGS. 9D, 10C, and 10E. The extended first stator vanes 4187 and the short first stator vanes 4188 can also be seen alternating circumferentially around the first stator 4180. The extended first stator vanes 4187 and the short first stator vanes 4188 may each include a curved portion 4181 that may be swept or curved backwards relative to the direction of rotation 4139 of the corresponding first impeller 4150. Alternatively, the curved portion 4181 that may be swept or curved forwards relative to the direction of rotation 4139 of the corresponding first impeller 4150. The curved portion 4181 of each extended first stator vane 4187 and the curved portion of each short first stator vane 4188 may shaped identically or the curved portions 4181 may be shaped differently such that the differently shaped curved portions 4181 alternate circumferentially around the first stator 4180. The extended first stator vanes 4187 and the short first stator vanes 4188 may each comprise a straight portion 4185 that extends radially inward from the curved portion 4181. The straight portion 4185 of each of the extended first stator vanes 4187 may extend radially inward further than the straight portion 4185 of each of the short first stator vanes 4188, as can be seen in FIGS. 9D, 10C, and 10E. The radially inward end of the extended first stator vanes 4187 may be approximately 1.8 mm from the axis of rotation of the shaft 4146. The radially inward end of the short first stator vanes 4188 may be approximately 4.5 mm from the axis of rotation of the shaft 4146. The radius of first stator vanes 4187, 4188, i.e., at the outermost point of the curved portion, may be 9.5 mm. The first stator 4180 may also include a shaft opening 4189 through which the shaft 4146 passes to reach the first impeller 4150.

Each first stator 4180 may also include a first stator opening 4186 that is located downstream of the first stator vanes 4187, 4188 to direct the flow of air to the second impeller 4160. The first stator opening 4186 may also be defined, at least in part, by a first stator lower shroud 4182B. The first stator lower shroud 4182B may prevent the flow of gas from the first impeller 4150 from passing straight on to the second impeller 4160 in an axial direction by directing the flow of gas radially through the first stator vanes 4187 and then through the first stator opening 4186. Each first stator 4180 may also include a first stator upper shroud 4182A to direct the flow of air from the first impeller 4150 to the first stator opening 4186 in an axial direction by preventing the flow of gas from flowing axially back to the underside of the first impeller shroud 4152. The corresponding first impeller 4150 may also be positioned adjacent to the first stator upper shroud 4182A.

Each first stator 4180 may also include a first stator housing 4184 that, at least in part, defines the flow path 4138. Each second impeller 4160 and each second stator 4190 may be at least partially contained within the corresponding first stator housing 4184 such that the flow of air travelling along the flow path 4138 past the second impeller 4160 and through the second stator 4190 also passes through the first stator housing 4184. In other words, the second compression stage 4137 may be located within the first stator housing 4184. Accordingly, each first stator housing 4184 may at least partially define the corresponding blower outlet 4141.

Furthermore, each first stator housing 4184 may include a mounting structure 4183 to connect the blower 4142 to the RPT system. In the depicted examples, each mounting structure 4183 is in the form of a pair of mounting rails extending around the outer circumference of each first stator housing 4184. As described above, the lower housing portion 4133 may be in the form of a clamshell that encloses the blower 4142 such that the mounting rails 4183 facilitate attachment to the plenum chamber 3200, as shown in FIG. 6B.

As explained above, each second compression stage 4137 may be contained within the corresponding first stator housing 4184 and each such second compression stage 4137 may be comprised of a second impeller 4160 (described above) and a second stator 4190. The second stator 4190 may include a top ring 4192, a base ring 4194, and a plurality of second stator vanes 4191 between the top ring 4192 and the base ring 4194. The second stator vanes 4191 may direct the flow of air from the second impeller 4160 to the blower outlet 4141 in a radial and axial direction, reduce the velocity of the flow of air from the second impeller 4160, and increase the pressure of the flow of air from the second impeller 4160. Each of the second stator vanes may have a constant depth D in a radial direction and an increasing width W in a circumferential direction from the top ring 4192 to the base ring 4194, as shown in FIGS. 11A and 11B.

The top ring 4192 may also include a top ring recess 4195 and the base ring 4194 includes a base ring recess 4196. The top ring recess 4195 and the base ring recess 4196 allow a flexible printed circuit board assembly (PCBA) to pass therethrough to provide power and control signals to the motor 4145. As can be seen in FIGS. 6B, 7E, and 10A the motor 4145 is also contained, at least partially, within the second stator 4190. Thus, the motor 4145 may partially define an internal boundary of the flow path 4138.

The second stator 4190 may also at least partially define the blower outlet 4141. Second stator outlet ribs 4193 can be seen in FIGS. 11A-11C joining corresponding second stator vanes 4191 to the base ring 4194. Thus, once the flow of gas has passed through the second stator vanes 4191, the flow of air is then directed out of the blower 4142 and into the plenum chamber 3200 through the blower outlet 4141 and between the second stator outlet ribs 4193. As can be seen in FIG. 6B, for example, the blower outlet 4141 may be located near the center of the blower 4142 in the axial direction.

5.4.1.1.1.6 End Caps 4144

At each axial end of the blower 4142, an end cap 4144 may also be provided to enclose the first compression stage 4136, including the first impeller 4150 and at least a portion of the first stator 4180. The end cap 4144 may at least partially define the blower inlet 4143 for each axial end of the blower 4142. In other words, the flow of air for the first compression stage 4136 may be drawn in through the blower inlet 4143 defined by the end cap 4144. Each end cap 4144 may be constructed to reduce noise and/or vibration. Each end cap 4144 may be formed from a rigid material to provide structural integrity and a less rigid, elastically deformable material overmolded to the rigid material to reduce noise and/or vibration. Other housing structures of the blower 4142, e.g., the first stator housing 4184, may also be formed from a similar construction to mitigate noise and vibration, since these are the most external components of the blower 4142. The end cap 4144 may also be integrated with the blower's 4142 housing structures, e.g., the first stator housing 4184, in one piece of homogeneous material or with the plenum chamber's 3200 housing structures, e.g., the lower housing portion 4133. Alternatively, the end cap 4144 may be mounted to the lower housing portion 4133 such that it is isolated from the blower 4142. Membranes or other flexible structures may be provided between the end cap 4144 and the other blower components to absorb noise and vibration.

Alternatively, to the passive noise mitigation measures described above, incorporating active noise cancelation features into the blower 4142 or elsewhere in the plenum chamber 3200 is also possible, such incorporating microphones in the RPT device.

5.4.1.1.1.7 Single Stage Pressure Generator

FIG. 14 depicts another example of the blower 4142 according to the present technology that includes a single stage of compression on each side of the motor 4145. The motor 4145 may have a single shaft 4146 protruding from each end thereof to drive corresponding impellers 4160. The impellers 4160 may each be associated with a stator 4190 on each side of the motor 4145. The blower 4142 may also have a housing 4148 on each side with a blower inlet 4143 and a mounting structure 4183 to secure the blower 4142 to the plenum chamber 3200. Each housing 4148 may enclose the corresponding impeller 4160 and the corresponding stator 4190. The impellers 4160 and the stators 4190 of this example may include any of the features described with respect to the examples above. While it may be necessary for the motor 4145 of this example to operate at a higher speed to generate flow rates and pressures comparable to the dual-stage examples described above, this single stage variation may provide a lighter and more compact design that is less obtrusive and lighter for the patient.

5.4.1.2 Transducer(s)

Transducers may be internal of the RPT device, or external of the RPT device. External transducers may be located for example on or form part of the air circuit, e.g., the patient interface. External transducers may be in the form of non-contact sensors such as a Doppler radar movement sensor that transmit or transfer data to the RPT device.

In one form of the present technology, one or more transducers 4270 are located upstream and/or downstream of the pressure generator 4140, such as one or more of those listed above. The one or more transducers 4270 may be constructed and arranged to generate signals representing properties of the flow of air such as a flow rate, a pressure, or a temperature at that point in the pneumatic path.

5.4.1.2.1 Flow Rate Sensor

A flow rate sensor 4274 in accordance with the present technology may be based on a differential pressure transducer, for example, an SDP600 Series differential pressure transducer from SENSIRION.

5.4.1.2.2 Pressure Sensor

A pressure sensor 4272 in accordance with the present technology is located in fluid communication with the pneumatic path. An example of a suitable pressure sensor is a transducer from the HONEYWELL ASDX series. An alternative suitable pressure sensor is a transducer from the NPA Series from GENERAL ELECTRIC.

5.4.1.2.3 Motor Speed Transducer

In one form of the present technology a motor speed transducer 4276 is used to determine a rotational velocity of the motor 4145 and/or the blower 4142.

5.4.2 RPT Device Electrical Components

5.4.2.1 Power Supply

A power supply 4210 may be located internally or externally of the external housing 4010 of the RPT device 4000.

In the exemplary RPT system of FIGS. 6A-6C, the power supply 4210 may be in the form of a battery that has at least one electrochemical cell. The power supply 4210 in the form of a battery may be supported by the positioning and stabilising structure 3300 on a region of the patient's head adjacent to the parietal bone. The power supply 4210 in the form of a battery may also be contained within the positioning and stabilising structure 3300. In other words, the power supply 4210 in the form of a battery may be at least partially enclosed by the materials of the positioning and stabilising structure 3300. If the power supply 4210 in the form of a battery is completely enclosed by the positioning and stabilising structure 3300, then the positioning and stabilising structure 3300 may include an opening to provide access to the power supply 4210 and the opening may be closed with hook-and-loop fastener(s), button(s), snap(s), etc.

In the example of the power supply 4210 in the form of a battery, the battery may be shaped to generally conform to the shape of the corresponding portion of the patient's head. By shaping the battery this, the power supply 4210 may maintain a relatively low profile that is minimally obtrusive to the patient. The positioning and stabilising structure 3300 may also include mounting point(s) for add-on features for the power supply 4210, e.g., a supplemental battery.

5.4.2.2 Input Devices

In one form of the present technology, an RPT device 4000 includes one or more input devices 4220 in the form of buttons, switches or dials to allow a person to interact with the device. The buttons, switches or dials may be physical devices, or software devices accessible via a touch screen. The buttons, switches or dials may, in one form, be physically connected to the external housing 4010, or may, in another form, be in wireless communication with a receiver that is in electrical connection to the central controller 4230.

In the example of the present technology depicted in FIGS. 6A-6C, one or more input devices 4220, such as those described above, may be provided to the upper housing portion 4132 or the lower housing portion 4133 of the plenum chamber or to the positioning and stabilising structure 3300.

5.4.2.3 Central Controller

In one form of the present technology, the central controller 4230 is one or a plurality of processors suitable to control an RPT device 4000.

In some forms of the present technology, the central controller 4230 is configured to implement the one or more methodologies described herein, such as the one or more algorithms expressed as computer programs stored in a non-transitory computer readable storage medium, such as memory 4260. In some forms of the present technology, the central controller 4230 may be integrated with an RPT device 4000. However, in some forms of the present technology, some methodologies may be performed by a remotely located device. For example, the remotely located device may determine control settings for a ventilator or detect respiratory related events by analysis of stored data such as from any of the sensors described herein.

In the example depicted in FIGS. 6A-6C, the RPT system may include a control system to control the blower 4142 and the control system may include one or more of the features described in the preceding paragraphs of this section. The control system may include a flexible printed circuit board assembly (PCBA) that comprises a microprocessor, such as those described above. The microprocessor is may be programmed to perform at least one of closed-loop pressure control based on sensed pressure data, flow rate estimation, and automatically adjusting expiration pressure relief. The control system may also a drive circuit to control the power supply 4210 separately from the blower 4142.

5.4.2.4 Memory

In accordance with one form of the present technology the RPT device 4000 includes memory 4260, e.g., non-volatile memory. In some forms, memory 4260 may include battery powered static RAM. In some forms, memory 4260 may include volatile RAM.

Memory 4260 may be located on the PCBA 4202. Memory 4260 may be in the form of EEPROM, or NAND flash.

Additionally or alternatively, RPT device 4000 includes a removable form of memory 4260, for example a memory card made in accordance with the Secure Digital (SD) standard.

In one form of the present technology, the memory 4260 acts as a non-transitory computer readable storage medium on which is stored computer program instructions expressing the one or more methodologies described herein, such as the one or more algorithms 5.4.2.5 Data Communication Systems In one form of the present technology, a data communication interface 4280 is provided, and is connected to the central controller 4230. Data communication interface 4280 may be connectable to a remote external communication network 4282 and/or a local external communication network 4284. The remote external communication network 4282 may be connectable to a remote external device 4286. The local external communication network 4284 may be connectable to a local external device 4288.

In one form, data communication interface 4280 is part of the central controller 4230. In another form, data communication interface 4280 is separate from the central controller 4230, and may comprise an integrated circuit or a processor.

In one form, the remote external communication network 4282 is the Internet. The data communication interface 4280 may use wired communication (e.g. via Ethernet, or optical fibre) or a wireless protocol (e.g. CDMA, GSM, LTE) to connect to the Internet.

In one form, the local external communication network 4284 utilises one or more communication standards, such as Bluetooth, or a consumer infrared protocol.

In one form, the remote external device 4286 is one or more computers, for example a cluster of networked computers. In one form, remote the external device 4286 may be virtual computers, rather than physical computers. In either case, such a remote external device 4286 may be accessible to an appropriately authorised person such as a clinician.

The local external device 4288 may be a personal computer, mobile phone, tablet or remote control.

5.4.3 RPT Device Algorithms

As mentioned above, in some forms of the present technology, the central controller 4230 may be configured to implement one or more algorithms expressed as computer programs stored in a non-transitory computer readable storage medium, such as memory 4260. The algorithms are generally grouped into groups referred to as modules.

5.4.4 Oxygen Delivery

In one form of the present technology, supplemental oxygen 4001 is delivered to one or more points in the pneumatic path, such as upstream of the pneumatic block 4020, to the air circuit 4170 and/or to the patient interface 3000.

5.5 Glossary

For the purposes of the present technology disclosure, in certain forms of the present technology, one or more of the following definitions may apply. In other forms of the present technology, alternative definitions may apply.

5.5.1 General

Air: In certain forms of the present technology, air may be taken to mean atmospheric air, and in other forms of the present technology air may be taken to mean some other combination of breathable gases, e.g. atmospheric air enriched with oxygen.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g., acoustic) noise may be considered to be the background noise level in the room where a patient is located, other than for example noise generated by an RPT device or emanating from a mask or patient interface. Ambient noise may be generated by sources outside the room.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Flow rate: The volume (or mass) of air delivered per unit time. Flow rate may refer to an instantaneous quantity. In some cases, a reference to flow rate will be a reference to a scalar quantity, namely a quantity having magnitude only. In other cases, a reference to flow rate will be a reference to a vector quantity, namely a quantity having both magnitude and direction. Flow rate may be given the symbol Q. 'Flow rate' is sometimes shortened to simply 'flow' or 'airflow'.

Humidifier: The word humidifier will be taken to mean a humidifying apparatus constructed and arranged, or configured with a physical structure to be capable of providing a therapeutically beneficial amount of water ($H_2O$) vapour to a flow of air to ameliorate a medical respiratory condition of a patient.

Leak: The word leak will be taken to be an unintended flow of air. In one example, leak may occur as the result of an incomplete seal between a mask and a patient's face. In another example leak may occur in a swivel elbow to the ambient.

Patient: A person, whether or not they are suffering from a respiratory condition.

Pressure: Force per unit area. Pressure may be expressed in a range of units, including $cmH_2O$, $g\text{-}f/cm^2$ and hectopascal. 1 $cmH_2O$ is equal to 1 $g\text{-}f/cm^2$ and is approximately 0.98 hectopascal. In this specification, unless otherwise stated, pressure is given in units of $cmH_2O$.

Respiratory Pressure Therapy (RPT): The application of a supply of air to an entrance to the airways at a treatment pressure that is typically positive with respect to atmosphere.

5.5.1.1 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, an exemplary form of LSR has a Shore A (or Type A) indentation hardness in the range of about 35 to about 45 as measured using ASTM D2240.

Polycarbonate: a thermoplastic polymer of Bisphenol-A Carbonate.

5.5.1.2 Mechanical Properties

Resilience: Ability of a material to absorb energy when deformed elastically and to release the energy upon unloading.

Resilient: Will release substantially all of the energy when unloaded. Includes e.g. certain silicones, and thermoplastic elastomers.

Hardness: The ability of a material per se to resist deformation (e.g. described by a Young's Modulus, or an indentation hardness scale measured on a standardised sample size).

- 'Soft' materials may include silicone or thermo-plastic elastomer (TPE), and may, e.g. readily deform under finger pressure.
- 'Hard' materials may include polycarbonate, polypropylene, steel or aluminium, and may not e.g. readily deform under finger pressure.

Stiffness (or rigidity) of a structure or component: The ability of the structure or component to resist deformation in response to an applied load. The load may be a force or a moment, e.g. compression, tension, bending or torsion. The structure or component may offer different resistances in different directions.

Floppy structure or component: A structure or component that will change shape, e.g. bend, when caused to support its own weight, within a relatively short period of time such as 1 second.

Rigid structure or component: A structure or component that will not substantially change shape when subject to the loads typically encountered in use. An example of such a use may be setting up and maintaining a patient interface in sealing relationship with an entrance to a patient's airways, e.g. at a load of approximately 20 to 30 cmH$_2$O pressure.

As an example, an I-beam may comprise a different bending stiffness (resistance to a bending load) in a first direction in comparison to a second, orthogonal direction. In another example, a structure or component may be floppy in a first direction and rigid in a second direction.

5.5.2 Respiratory Cycle

Apnea: According to some definitions, an apnea is said to have occurred when flow falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort, despite the airway being patent. A mixed apnea occurs when a reduction or absence of breathing effort coincides with an obstructed airway.

Expiratory portion of a breathing cycle: The period from the start of expiratory flow to the start of inspiratory flow.

Inspiratory portion of a breathing cycle: The period from the start of inspiratory flow to the start of expiratory flow will be taken to be the inspiratory portion of a breathing cycle.

5.5.3 Anatomy 5.5.3.1 Anatomy of the Face

Nares (Nostrils): Approximately ellipsoidal apertures forming the entrance to the nasal cavity. The singular form of nares is naris (nostril). The nares are separated by the nasal septum.

Otobasion inferior: The lowest point of attachment of the auricle to the skin of the face.

Otobasion superior: The highest point of attachment of the auricle to the skin of the face.

Sagittal plane: A vertical plane that passes from anterior (front) to posterior (rear) dividing the body into right and left halves.

5.5.3.2 Anatomy of the Skull

Occipital bone: The occipital bone is situated at the back and lower part of the cranium. It includes an oval aperture, the foramen magnum, through which the cranial cavity communicates with the vertebral canal. The curved plate behind the foramen magnum is the squama occipitalis.

Parietal bones: The parietal bones are the bones that, when joined together, form the roof and sides of the cranium.

5.5.3.3 Anatomy of the Respiratory System

Nasal cavity: The nasal cavity (or nasal fossa) is a large air filled space above and behind the nose in the middle of the face. The nasal cavity is divided in two by a vertical fin called the nasal septum. On the sides of the nasal cavity are three horizontal outgrowths called nasal conchae (singular "concha") or turbinates. To the front of the nasal cavity is the nose, while the back blends, via the choanae, into the nasopharynx.

5.5.4 Patient Interface

Anti-asphyxia valve (AAV): The component or sub-assembly of a mask system that, by opening to atmosphere in a failsafe manner, reduces the risk of excessive $CO_2$ rebreathing by a patient.

Headgear: Headgear will be taken to mean a form of positioning and stabilizing structure designed for use on a head. For example the headgear may comprise a collection of one or more struts, ties and stiffeners configured to locate and retain a patient interface in position on a patient's face for delivery of respiratory therapy. Some ties are formed of a soft, flexible, elastic material such as a laminated composite of foam and fabric.

Membrane: Membrane will be taken to mean a typically thin element that has, preferably, substantially no resistance to bending, but has resistance to being stretched.

Plenum chamber: a mask plenum chamber will be taken to mean a portion of a patient interface having walls at least partially enclosing a volume of space, the volume having air therein pressurised above atmospheric pressure in use. A shell may form part of the walls of a mask plenum chamber.

Seal: May be a noun form ("a seal") which refers to a structure, or a verb form ("to seal") which refers to the effect. Two elements may be constructed and/or arranged to 'seal' or to effect 'sealing' therebetween without requiring a separate 'seal' element per se.

Stiffener: A stiffener will be taken to mean a structural component designed to increase the bending resistance of another component in at least one direction.

Strut: A strut will be taken to be a structural component designed to increase the compression resistance of another component in at least one direction.

Tie (noun): A structure designed to resist tension.

Vent: (noun): A structure that allows a flow of air from an interior of the mask, or conduit, to ambient air for clinically effective washout of exhaled gases. For example, a clinically effective washout may involve a flow rate of about 10 litres per minute to about 100 litres per minute, depending on the mask design and treatment pressure.

5.6 Other Remarks

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

5.7 Reference Signs List

| | |
|---|---|
| plane curve | 301D |
| surface | 302D |
| impeller | 500 |
| first impeller portion | 500-1 |
| second impeller portion | 500-2 |
| impeller blade | 510 |
| impeller blade leading edge | 511 |
| impeller blade trailing edge | 512 |
| inner blade portion | 513 |
| opening | 514 |
| first edge | 515 |
| second edge | 517 |
| curved surface | 519 |
| top shroud | 520 |
| top shroud first portion | 520-1 |
| top shroud second portion | 520-2 |
| inlet wall | 521 |
| impeller inlet | 522 |
| leading edge | 523 |
| impeller outlet | 524 |
| bottom shroud | 525 |
| bottom shroud first portion | 525-1 |
| bottom shroud second portion | 525-2 |
| curved surface | 527 |
| hub | 530 |
| flow passage | 540 |
| first fastening portion | 550 |
| hub portion | 550-1 |
| projection | 550-2 |
| second fastening portion | 555 |
| annular slot | 555-1 |
| slot | 555-2 |
| blower | 600 |
| housing | 610 |
| blower inlet | 612 |
| blower outlet | 614 |
| curved surface | 615 |
| motor | 620 |
| rotor | 625 |
| channel | 650 |
| patient | 1000 |
| sleeping patient | 1000 |
| bed partner | 1100 |
| headbox | 2000 |
| ground electrode ISOG | 2010 |
| respiratory inductance plethysmogram | 2040 |
| respiratory inductance plethysmogram | 2045 |
| oro-nasal cannula | 2050 |
| body position sensor | 2060 |
| patient interface | 3000 |
| seal-forming structure | 3100 |
| plenum chamber | 3200 |
| perimeter | 3210 |
| marginal edge | 3220 |
| positioning and stabilising structure | 3300 |
| wire | 3301 |
| tube | 3302 |
| lateral portion of the tie | 3303 |
| superior portion of the tie | 3304 |
| posterior portion of the tie | 3305 |
| tab | 3306 |
| wire retainer | 3307 |
| adjustment mechanism | 3308 |
| vent assembly | 3400 |
| exterior vent hole surface | 3401 |
| vent hole | 3402 |
| vent hole extension | 3403 |
| base | 3404 |
| flexible membrane | 3405 |
| divider | 3406 |
| interior vent hole surface | 3407 |

-continued

| | |
|---|---|
| internal surface | 3408 |
| vent flow | 3409 |
| pressurized flow | 3410 |
| connection port | 3600 |
| forehead support | 3700 |
| RPT Device | 4000 |
| supplementary oxygen | 4001 |
| external housing | 4010 |
| upper portion | 4012 |
| lower portion | 4014 |
| panel | 4015 |
| chassis | 4016 |
| handle | 4018 |
| pneumatic block | 4020 |
| pneumatic component | 4100 |
| air filter | 4110 |
| inlet air filter | 4112 |
| outlet air filter | 4114 |
| muffler | 4120 |
| inlet muffler | 4122 |
| outlet muffler | 4124 |
| attachment structure | 4130 |
| plenum chamber outlet | 4131 |
| upper housing portion | 4132 |
| lower housing portion | 4133 |
| pressure port | 4134 |
| heat and moisture exchanger (HME) retention structure | 4135 |
| first compression stage | 4136 |
| second compression stage | 4137 |
| flow path | 4138 |
| direction of rotation | 4139 |
| pressure generator | 4140 |
| blower outlet | 4141 |
| blower | 4142 |
| blower inlet | 4143 |
| end cap | 4144 |
| motor | 4145 |
| shaft | 4146 |
| housing | 4148 |
| first impeller | 4150 |
| first impeller vanes | 4151 |
| first impeller shroud | 4152 |
| first impeller hub | 4153 |
| first impeller vane portion | 4154 |
| second impeller vane portion | 4155 |
| first impeller shroud portion | 4156 |
| second impeller shroud portion | 4157 |
| second impeller | 4160 |
| air circuit | 4170 |
| heated air circuit | 4171 |
| first stator | 4180 |
| curved portion | 4181 |
| first stator upper shroud | 4182A |
| first stator lower shroud | 4182B |
| mounting rails | 4183 |
| first stator housing | 4184 |
| straight portion | 4185 |
| first stator opening | 4186 |
| extended first stator vanes | 4187 |
| short first stator vanes | 4188 |
| shaft opening | 4189 |
| second stator | 4190 |
| second stator vanes | 4191 |
| top ring | 4192 |
| second stator outlet rib | 4193 |
| base ring | 4194 |
| top ring recess | 4195 |
| base ring recess | 4196 |
| electrical component | 4200 |
| printed circuit board assembly | 4202 |
| power supply | 4210 |
| input device | 4220 |
| central controller | 4230 |
| retainer | 4231 |
| clock | 4232 |
| therapy device controller | 4240 |
| protection circuit | 4250 |
| memory | 4260 |
| transducer | 4270 |
| pressure sensor | 4272 |
| flow rate sensor | 4274 |
| motor speed transducer | 4276 |
| data communication interface | 4280 |
| remote external communication network | 4282 |
| local external communication network | 4284 |
| remote external device | 4286 |
| local external device | 4288 |
| output device | 4290 |
| display driver | 4292 |
| display | 4294 |
| method | 4500 |
| step | 4520 |
| step | 4530 |
| step | 4540 |
| step | 4550 |
| step | 4560 |
| humidifier | 5000 |
| humidifier inlet | 5002 |
| humidifier outlet | 5004 |
| humidifier base | 5006 |
| water reservoir | 5110 |
| humidifier reservoir | 5110 |
| conductive portion | 5120 |
| humidifier reservoir dock | 5130 |
| locking lever | 5135 |
| water level indicator | 5150 |
| humidifier transducer | 5210 |
| pressure transducer | 5212 |
| flow rate transducer | 5214 |
| temperature transducer | 5216 |
| humidity sensor | 5218 |
| heating element | 5240 |
| humidifier controller | 5250 |
| central humidifier controller | 5251 |
| heating element controller | 5252 |
| air circuit controller | 5254 |
| monitoring apparatus | 7100 |

The invention claimed is:

1. A respiratory pressure therapy (RPT) system comprising:
a plenum chamber pressurisable to a therapeutic pressure of at least 6 cmH$_2$O above ambient air pressure;
a seal-forming structure constructed and arranged to form a seal with a region of the patient's face at or surrounding an entrance to the patient's airways such that a flow of air at said therapeutic pressure is delivered to at least the entrance to the patient's nares, the seal-forming structure constructed and arranged to maintain said therapeutic pressure in the plenum chamber throughout the patient's respiratory cycle in use;
a positioning and stabilising structure constructed and arranged to provide an elastic force to hold the seal-forming structure in a therapeutically effective position on the patient's head, the positioning and stabilising structure comprising a tie, a lateral portion of the tie being constructed and arranged to overlie a region of the patient's head superior to the otobasion superior in use, and a superior portion of the tie being constructed and arranged to overlie a region of the patient's head in a region of the parietal bone in use, wherein the positioning and stabilising structure has a non-rigid decoupling portion;
a blower connected to the plenum chamber such that in use the blower is suspended from the patient's head and configured to generate the flow of air and pressurise the plenum chamber to the therapeutic pressure, the blower comprising:
a first side and a second side opposite the first side;
a motor having a first end on the first side of the blower and a second end on the second side of the blower;

a shaft having a first shaft end extending from the first end of the motor and a second shaft end extending from the second end of the motor;

a pair of first impellers and a pair of second impellers, one of the first impellers and one of the second impellers arranged in series on the shaft proximal to the first shaft end and the other of the first impellers and the other of the second impellers arranged in series on the shaft proximal to the second shaft end such that both first impellers and both second impellers are driveable simultaneously by the motor;

a pair of first stators, each of the first stators being positioned on a corresponding one of the first side of the blower and the second side of the blower, each of the first stators being positioned downstream of the first impeller on the corresponding one of the first side of the blower and the second side of the blower along the flow of air generated by the blower in use, and each of the first stators being positioned upstream of the second impeller on the corresponding one of the first side of the blower and the second side of the blower along the flow of air generated by the blower in use;

a pair of second stators, each of the second stators being positioned on a corresponding one of the first side of the blower and the second side of the blower, and each of the second stators being positioned downstream of a corresponding one of the second impellers along the flow of air generated by the blower in use;

a pair of end caps, each of the end caps at least partially enclosing a corresponding one of the first impellers, and each of the end caps at least partially defining a blower inlet;

a pair of blower outlets, each of the blower outlets being positioned downstream of a corresponding one of the second stators; and a pair of flow paths, each of the flow paths being at least partly formed by the blower inlet at least partially defined by the end cap on a corresponding one of the first side of the blower and the second side of the blower, the first impeller on the corresponding one of the first side of the blower and the second side of the blower, the first stator on the corresponding one of the first side of the blower and the second side of the blower, the second impeller on the corresponding one of the first side of the blower and the second side of the blower, the second stator on the corresponding one of the first side of the blower and the second side of the blower, and the blower outlet on the corresponding one of the first side of the blower and the second side of the blower; and a power supply configured to provide electrical power to the blower.

2. The RPT system of claim 1, wherein the blower is suspended from the patient's head such that an axis of rotation of the motor is generally perpendicular to the patient's sagittal plane.

3. The RPT system of claim 1, wherein each of the first stators comprises a plurality of first stator vanes to direct the flow of air in a radial direction from a corresponding one of the first impellers to an opening of a corresponding one of the first stators, reduce the velocity of the flow of air from the corresponding one of the first impellers, and increase the pressure of the flow of air from the corresponding one of the first impellers.

4. The RPT system of claim 3, wherein the plurality of first stator vanes comprise extended first stator vanes and short first stator vanes, the extended first stator vanes extending further radially inward than the short first stator vanes, and
wherein the extended first stator vanes and the short first stator vanes alternate circumferentially around the first stator.

5. The RPT system of claim 4, wherein the extended first stator vanes and the short first stator vanes each comprise a curved portion that is swept backwards relative to the direction of rotation of the corresponding first impeller, and
wherein the extended first stator vanes and the short first stator vanes each comprise a straight portion that extends radially inward from the curved portion, the straight portion of each of the extended first stator vanes extending radially inward further than the straight portion of each of the short first stator vanes.

6. The RPT system of claim 3, wherein each of the first stators comprises a first stator opening downstream of the plurality of first stator vanes to direct the flow of air to a corresponding one of the second impellers.

7. The RPT system of claim 6, wherein each of the first stators further comprises a first stator upper shroud to direct the flow of air from a corresponding one of the first impellers to the first stator opening of the corresponding first stator in an axial direction, the corresponding one of the first impellers being positioned adjacent to the first stator upper shroud of the corresponding first stator.

8. The RPT system of claim 1, wherein each of the first stators further comprises a first stator housing, and
wherein each of the second impellers and a corresponding one of the second stators are at least partially contained within the corresponding first stator housing such that the flow of air travelling along each of the flow paths past a corresponding one of the second impellers and through the corresponding one of the second stators also passes through the corresponding first stator housing.

9. The RPT system of claim 8, wherein each of the first stator housings at least partially defines a corresponding one of the blower outlets.

10. The RPT system of claim 9, wherein each of the first stator housings comprises a mounting structure to connect the blower to the RPT system.

11. The RPT system of claim 10, wherein each of the mounting structures further comprises a pair of mounting rails extending around an outer circumference of the corresponding first stator housing.

12. The RPT system of claim 1, wherein each of the end caps is constructed to dampen sound and vibration.

13. The RPT system of claim 12, wherein each of the end caps is constructed from a rigid material to provide structural integrity and a less rigid, elastically deformable material overmolded to the rigid material to dampen sound and vibration.

14. The RPT system of claim 1, wherein each of the first impellers and each of the second impellers comprises an impeller hub, impeller vanes extending radially from the impeller hub, and an impeller shroud.

15. The RPT system of claim 14, wherein each of the impeller vanes comprises a first impeller vane portion that extends only in a radial direction and a second impeller vane portion that extends in a radial and axial direction.

16. The RPT system of claim 15, wherein the first impeller vane portion of each of the impeller vanes of each of the first impellers and each of the second impellers has a constant cross-section and is radially inward relative to the second impeller vane portion,
wherein the second impeller vane portion has a variable cross-section and is radially outward relative to the first impeller vane portion, and
wherein the constant cross-section of the first impeller vane portion is thinner than the variable cross-section of the second impeller vane portion.

17. The RPT system of claim 14, wherein the impeller shroud of each of the first impellers and each of the second impellers comprises a first impeller shroud portion that extends only in a radial direction and a second impeller shroud portion that extends in a radial and axial direction.

18. The RPT system of claim 14, wherein the impeller vanes of each of the first impellers and each of the second impellers are swept forward relative to the direction of rotation during operation.

19. The RPT system of claim 1, wherein each of the second stators further comprises a top ring, a base ring, and a plurality of second stator vanes that join the top ring and the base ring, and
wherein the plurality of second stator vanes direct the flow of air from the second impeller to a corresponding one of the blower outlets in a radial and axial direction, reduce the velocity of the flow of air from the second impeller, and increase the pressure of the flow of air from the second impeller.

20. The RPT system of claim 19, wherein each of the plurality of second stator vanes has a constant depth in a radial direction and an increasing width in a circumferential direction from the top ring to the base ring.

21. The RPT system of claim 19, wherein the top ring includes a top ring recess and the base ring includes a base ring recess, the top ring recess and the base ring recess allowing a flexible printed circuit board assembly (PCBA) to pass therethrough.

22. A blower for a respiratory pressure therapy (RPT) system, the blower being configured to generate a flow of air at a therapeutic pressure of at least 6 cmH$_2$O above ambient air pressure, the blower comprising:
a first side and a second side opposite the first side;
a motor having a first end on the first side of the blower and a second end on the second side of the blower;
a shaft having a first shaft end extending from the first end of the motor and a second shaft end extending from the second end of the motor;
a pair of first impellers and a pair of second impellers, one of the first impellers and one of the second impellers arranged in series on the shaft proximal to the first shaft end and the other of the first impellers and the other of the second impellers arranged in series on the shaft proximal to the second shaft end such that both first impellers and both second impellers are driveable simultaneously by the motor;
a pair of first stators, each of the first stators being positioned on a corresponding one of the first side of the blower and the second side of the blower, each of the first stators being positioned downstream of the first impeller on the corresponding one of the first side of the blower and the second side of the blower along the flow of air generated by the blower in use, and each of the first stators being positioned upstream of the second impeller on the corresponding one of the first side of the blower and the second side of the blower along the flow of air generated by the blower in use;
a pair of second stators, each of the second stators being positioned on a corresponding one of the first side of the blower and the second side of the blower, and each of the second stators being positioned downstream of a corresponding one of the second impellers along the flow of air generated by the blower in use;
a pair of end caps, each of the end caps at least partially enclosing a corresponding one of the first impellers, and each of the end caps at least partially defining a blower inlet;
a pair of blower outlets, each of the blower outlets being positioned downstream of a corresponding one of the second stators; and
a pair of flow paths, each of the flow paths being at least partly formed by the blower inlet at least partially defined by the end cap on a corresponding one of the first side of the blower and the second side of the blower, the first impeller on the corresponding one of the first side of the blower and the second side of the blower, the first stator on the corresponding one of the first side of the blower and the second side of the blower, the second impeller on the corresponding one of the first side of the blower and the second side of the blower, the second stator on the corresponding one of the first side of the blower and the second side of the blower, and the blower outlet on the corresponding one of the first side of the blower and the second side of the blower.

23. The blower of claim 22, wherein the blower is suspended from the patient's head such that an axis of rotation of the motor is generally perpendicular to the patient's sagittal plane.

24. The blower of claim 22, wherein each of the first stators comprises a plurality of first stator vanes to direct the flow of air in a radial direction from a corresponding one of the first impellers to an opening of a corresponding one of the first stators, reduce the velocity of the flow of air from the corresponding one of the first impellers, and increase the pressure of the flow of air from the corresponding one of the first impellers.

25. The blower of claim 24, wherein the plurality of first stator vanes comprise extended first stator vanes and short first stator vanes, the extended first stator vanes extending further radially inward than the short first stator vanes, and
wherein the extended first stator vanes and the short first stator vanes alternate circumferentially around the first stator.

26. The blower of claim 25, wherein the extended first stator vanes and the short first stator vanes each comprise a curved portion that is swept backwards relative to the direction of rotation of the corresponding first impeller, and
wherein the extended first stator vanes and the short first stator vanes each comprise a straight portion that extends radially inward from the curved portion, the straight portion of each of the extended first stator vanes extending radially inward further than the straight portion of each of the short first stator vanes.

27. The blower of claim 24, wherein each of the first stators comprises a first stator opening downstream of the plurality of first stator vanes to direct the flow of air to a corresponding one of the second impellers.

28. The blower of claim 27, wherein each of the first stators further comprises a first stator upper shroud to direct the flow of air from a corresponding one of the first impellers to the first stator opening of the corresponding first stator in an axial direction, the corresponding one of the first impellers being positioned adjacent to the first stator upper shroud of the corresponding first stator.

29. The blower of claim 22, wherein each of the first stators further comprises a first stator housing, and
wherein each of the second impellers and a corresponding one of the second stators are at least partially contained within the corresponding first stator housing such that the flow of air travelling along each of the flow paths past a corresponding one of the second impellers and through the corresponding one of the second stators also passes through the corresponding first stator housing.

30. The blower of claim 29, wherein each of the first stator housings at least partially defines a corresponding one of the blower outlets.

31. The blower of claim 30, wherein each of the first stator housings comprises a mounting structure to connect the blower to the RPT system.

32. The blower of claim 31, wherein each of the mounting structures further comprises a pair of mounting rails extending around an outer circumference of the corresponding first stator housing.

33. The blower of claim 22, wherein each of the end caps is constructed to dampen sound and vibration.

34. The blower of claim 33, wherein each of the end caps is constructed from a rigid material to provide structural integrity and a less rigid, elastically deformable material overmolded to the rigid material to dampen sound and vibration.

35. The blower of claim 22, wherein each of the first impellers and each of the second impellers comprises an impeller hub, impeller vanes extending radially from the impeller hub, and an impeller shroud.

36. The blower of claim 35, wherein each of the impeller vanes comprises a first impeller vane portion that extends only in a radial direction and a second impeller vane portion that extends in a radial and axial direction.

37. The blower of claim 36, wherein the first impeller vane portion of each of the impeller vanes of each of the first impellers and each of the second impellers has a constant cross-section and is radially inward relative to the second impeller vane portion,
wherein the second impeller vane portion has a variable cross-section and is radially outward relative to the first impeller vane portion, and
wherein the constant cross-section of the first impeller vane portion is thinner than the variable cross-section of the second impeller vane portion.

38. The blower of claim 35, wherein the impeller shroud of each of the first impellers and each of the second impellers comprises a first impeller shroud portion that extends only in a radial direction and a second impeller shroud portion that extends in a radial and axial direction.

39. The blower of claim 35, wherein the impeller vanes of each of the first impellers and each of the second impellers are swept forward relative to the direction of rotation during operation.

40. The blower of claim 22, wherein each of the second stators further comprises a top ring, a base ring, and a plurality of second stator vanes that join the top ring and the base ring, and
wherein the plurality of second stator vanes direct the flow of air from the second impeller to a corresponding one of the blower outlets in a radial and axial direction, reduce the velocity of the flow of air from the second impeller, and increase the pressure of the flow of air from the second impeller.

41. The blower of claim 40, wherein each of the plurality of second stator vanes has a constant depth in a radial direction and an increasing width in a circumferential direction from the top ring to the base ring.

42. The blower of claim 40, wherein the top ring includes a top ring recess and the base ring includes a base ring recess, the top ring recess and the base ring recess allowing a flexible printed circuit board assembly (PCBA) to pass therethrough.

* * * * *